(12) United States Patent
Lutolf et al.

(10) Patent No.: US 10,934,529 B2
(45) Date of Patent: Mar. 2, 2021

(54) THREE DIMENSIONAL HYDROGELS FOR CULTURING ORGANOIDS

(71) Applicant: Ecole Polytechnique Fèdèrale de Lausanne, Lausanne (CH)

(72) Inventors: Matthias Lutolf, St-Sulpice (CH); Nikolce Gjorevski, Renens (CH)

(73) Assignee: Ecole Polytechnique Fèdèrale de Lausanne

( * ) Notice: Subject to any disclaimer, the term of this patent is extended or adjusted under 35 U.S.C. 154(b) by 0 days.

(21) Appl. No.: 15/757,149

(22) PCT Filed: Sep. 5, 2016

(86) PCT No.: PCT/EP2016/070880
§ 371 (c)(1),
(2) Date: Mar. 2, 2018

(87) PCT Pub. No.: WO2017/037295
PCT Pub. Date: Mar. 9, 2017

(65) Prior Publication Data
US 2018/0258403 A1 Sep. 13, 2018

(30) Foreign Application Priority Data
Sep. 3, 2015 (WO) ............... PCT/EP2015/070143

(51) Int. Cl.
| | | |
|---|---|---|
| *C12N 5/071* | (2010.01) | |
| *C12N 5/00* | (2006.01) | |
| *A61L 27/52* | (2006.01) | |
| *A61L 27/54* | (2006.01) | |
| *A61L 27/38* | (2006.01) | |
| *A61L 27/50* | (2006.01) | |
| *G01N 33/50* | (2006.01) | |

(52) U.S. Cl.
CPC ........ *C12N 5/0679* (2013.01); *A61L 27/3834* (2013.01); *A61L 27/50* (2013.01); *A61L 27/52* (2013.01); *A61L 27/54* (2013.01); *C12N 5/0068* (2013.01); *C12N 5/0625* (2013.01); *C12N 5/0632* (2013.01); *G01N 33/5008* (2013.01); *A61L 2300/252* (2013.01); *C12N 2513/00* (2013.01); *C12N 2533/30* (2013.01); *C12N 2533/50* (2013.01); *C12N 2533/52* (2013.01); *C12N 2537/10* (2013.01)

(58) Field of Classification Search
CPC .................................................. C12N 2513/00
See application file for complete search history.

(56) References Cited

FOREIGN PATENT DOCUMENTS

| WO | 2003040235 A1 | 5/2003 |
|---|---|---|
| WO | 2009099555 A2 | 9/2009 |
| WO | 2014117146 A1 | 7/2014 |
| WO | 2014180970 A1 | 11/2014 |
| WO | 2015157732 | 10/2015 |
| WO | 20150157732 A2 | 10/2015 |

OTHER PUBLICATIONS

Jing et al. Global Spine Journal, 2014, pp. 1-2.*
Jongpaiboonkit et al. Tissue Engineering, Part A, 2009, 15(2):343-353.*
Nakanishi et al. Science and Technology of Advance Materials, 2011, 12, pp. 1-9 as printed.*
Xiao et al. Biomacromolecules, 2009, 10:1939-1946.*
Francisco, et al. Biomaterials, 2013, 34(30): 7381-7388 or pp. 1-19 as printed.*
Yui et al. Nature Medicine, 2012, 18(4):618-624.*
Yang et al., PLOS ONE, 2013m 8(3), e59147, pp. 1-15.*
Asad Raza et al.; "The influence of matrix properties on growth and morphogenesis of human pancreatic ductal epithelial cells in 3D", Biomaterials, vol. 34, No. 21, Jul. 1, 2013.
"Bioartificial Matrices to Modulate Epithelial Morphogenesis", Dec. 1, 2013, XP055237935, retrieved form the internet: URL: https://smartech.gatech.edu/bitstream/handle/1853/52938/ENEMCHUKWU-DISSERTATION-2013.pdf.
Edward A. Phelps et al.: "Maleimide Cross-Linked Bioactive PEG Hydrogel Exhibits Improved Reaction Kinetics and Cross-Linking for Cell Encapsulation and in Situ Delivery", Advanced Materials, vol. 24, No. 1, Dec. 16, 2011, pp. 64-70.
Jha Amit K et al.: "Enhanced survival and engraftment of transplanted stem cells using growth factor sequestering hydrogels", Biomaterials, vol. 47, Jan. 22, 2015, pp. 1-12.
Toshiro Sato et al.: "Long-term Expansion of Epithelial Organoids From Human Colon, Adenoma, Adenocarcinoma, and Barrett's Epithelium", Gastroenterology, Elsevier, Amsterdam, NL, vol. 141, No. 5, Jul. 27, 2011, pp. 1762-1772.
Sato Toshiro et al.: "Single Lgr5 Stem Cells Build Crypt-Villus Structures In Vitro Without a Mesenchymal Niche", Nature, Nature Publishing Group, United Kingdom, vol. 459, No. 7244, May 14, 2009, pp. 262-265.
Yamada Yuji et al.: "Laminin-111-derived peptide-hyaluronate hydrogels as a synthetic basement membrane", Biomaterials, Elsevier science publishers BV., Barking, GB, vol. 34, No. 28, Jun. 10, 2013, pp. 6539-6547.
Samir P. Singh et al.: "A peptide functionalized poly(ethylene glycol) (PEG) hydrogel for investigating the influence of biochemical and biophysical matrix properties on tumor cell migration", biomaterials science., vol. 2, No. 7, Jan. 1, 2014, p. 1024.
Chung I-Ming et al: "Bioadhesive hydrogel microenvironments to modulate epithelial morphogenesis", Biomaterials, Elsevier Science Publishers BV., Barking, GB, vol. 29, No. 17, Jun. 1, 20018, pp. 2637-2645.
Search Report for corresponding International Application No. PCT/EP2016/070880, dated Nov. 25, 2016.
International Preliminary Report on Patentability for corresponding International application No. PCT/EP2016/070880, dated Mar. 6, 2018.

(Continued)

*Primary Examiner* — Bin Shen
(74) *Attorney, Agent, or Firm* — Tarolli, Sundheim, Covell & Tummino, LLP

(57) ABSTRACT

The invention provides hydrogels and methods for three-dimensional (3D) culture of adult epithelial stem cells and uses thereof.

24 Claims, 16 Drawing Sheets
Specification includes a Sequence Listing.

(56) References Cited

OTHER PUBLICATIONS

International Preliminary Report on Patentability for priority international application No. PCT/EP2015/070143, dated Mar. 6, 2018.
Ueno,T. et al.: 'Current status of intestinal transplantation', Surg. Today,vol. 40, No. 12, pp. 1112-1122, Dec. 2010.
Hynds,R.E. et al.:'The relevance of human stem cell-derived organoid models for epithelial translational medicine', Stem Cells Dayt. Ohio, vol. 31, No. 3, pp. 417-422, Mar. 2013.
Sato, T. et al.:'Long-term expansion of epithelial organoids from human colon, adenoma,adenocarcinoma, and Barrett's epithelium', Gastroenterology, vol. 141, No. 5, pp. 1762-1772, Nov. 2011.
Fukuda, M. et al.: 'Small intestinal stem cell identity is maintained with functional Paneth cells in heterotopically grafted epithelium onto the colon', Genes Dev., vol. 28, No. 16, pp. 1752-1757, Aug. 2014.
Hughes, C.S. et al.: Matrigel: a complex protein mixture required for optimal growth of cell culture, Proteomics 10, No. 9, pp. 1886-1890, May 2010.
Pierzchalaska, M. et al.: 'Prostaglandin E2 supports growth of chicken embryo intestinal organoids in Matrigel matrix',BioTechniques, vol. 52, No. 5, pp. 307-315, May 2012.
Eiraku, M. et al.:'Self-organizing optic-cup morphogenesis in three-dimensional culture', Nature, vol. 472, No. 7341, pp. 51-56, Apr. 2011.
Lowe, A. et al.: 'Intercellular Adhesion-Dependent Cell Survival and ROCK-Regulated Actomyosin-Driven Forces Mediate Self-Formation of a Retinal Organoid', Stem Cell Rep., vol. 6, No. 5, pp. 743-756, May 2016.
Velagapudi, R. P. et al.: 'Reciprocal induction of simple organogenesis by mouse kidney progenitor cells in three-dimensional co-culture', Am. J. Pathol., vol. 180, No. 2, pp. 819-830, Feb. 2012.
Ramachandran, S. D. et al.: 'In Vitro Generation of Functional Liver Organoid-Like Structures Using Adult Human Cells', PLoS ONE, vol. 10, No. 10, Oct. 2015.
Schumacher, M.A. et al.: The use of murine-derived fundic organoids in studies of gastric physiology, J. Physiol., vol. 593, No. Pt 8, pp. 1809-1827, Apr. 2015.
Calderon-Gierszal, E. L. et al.: 'Directed Differentiation of Human Embryonic Stem Cells into Prostate Organoids In Vitro and its Perturbation by Low-Dose Bisphenol A Exposure', PloS One, vol. 10, No. 7, p. e0133238, 2015.
Ewald, A. J. et al.: 'Isolation of mouse mammary organoids for long-term time-lapse imaging,'Cold Spring Harb. Protoc., vol. 2013, No. 2, pp. 130-133, Feb. 2013.
Nguyen-Ngoc, K. V. et al.: '3D Culture Assays of Murine Mammary Branching Morphogenesis and Epithelial Invasion', Methods Mol. Biol. Clifton NJ, vol. 1189, pp. 135-162, 2015.
Chang, C. C. et al.: 'A human breast epithelial cell type with stem cell characteristics as target cells for carcinogenesis', Radiat. Res., vol. 155, No. 1 Pt 2, pp. 201-207, Jan. 2001.
Longworth-Mills, E. et al.: 'Generating Inner Ear Organoids from Mouse Embryonic Stem Cells', Methods Mol. Biol. Clifton NJ, vol. 1341, pp. 391-406, 2016.
Chiu, L. L. Y. et al.: 'Biphasic electrical field stimulation aids in tissue engineering of multicell-type cardiac organoids', Tissue Eng. Part A, vol. 17, No. 11-12, pp. 1465-1477, Jun. 2011.
Soto-Gutierrez, A. N. et al.: 'Engineering of an hepatic organoid to develop liver assist devices', Cell Transplant., vol. 19, No. 6, pp. 815-822, 2010.
Boj, S. F. et al.: 'Organoid Models of Human and Mouse Ductal Pancreatic Cancer', Cell, vol. 160, No. 0, pp. 324-338, Jan. 2015.
Kessler M. K. et al.: 'The Notch and Wnt pathways regulate stemness and differentiation in human fallopian tube organoids', Nat. Commun., vol. 6, Dec. 2015.
Lancaster, M. A. et al.: 'Cerebral organoids model human brain development and microcephaly', Nature, vol. 501, No. 7467, Sep. 2013.

Kim, N. D. et al.: 'Inhibitory effects of retinoids on development of squamous metaplasia in rat mammary epithelial organoids cultured in Matrigel', Cancer Lett., vol. 110, No. 1-2, pp. 217-223, Dec. 1996.
Gjorevski, N. et al.: 'Biomaterials approaches in stem cell mechanobiology', Prog. Mol. Biol. Transl. Sci., vol. 126, pp. 257-278, 2014.
Lutolf, M. P. et al.: 'Synthetic matrix metalloproteinase-sensitive hydrogels for the conduction of tissue regeneration: Engineering cell-invasion characteristics', Proc. Natl. Acad. Sci., vol. 100, No. 9, pp. 5413-5418, Apr. 2003.
Lutolf, M. P. et al.: 'Designing materials to direct stem-cell fate', Nature, vol. 462, No. 7272, pp. 433-441, Nov. 2009.
Hasltendberg, S. et al.: 'Biologically engineered protein-graft-poly(ethylene glycol) hydrogels: a cell adhesive and plasmin-degradable biosynthetic material for tissue repair', Biomacromolecules, vol. 3, No. 4, pp. 710-723, Aug. 2002.
Luetolf, M. et al.: 'Synthetic Matrix for Controlled Cell Ingrowth and Tissue Regeneration', WO03040235 (A1), May 15, 2003.
Rizzi, S. C. et al.: 'Recombinant protein-co-PEG networks as cell-adhesive and proteolytically degradable hydrogel matrixes. Part II: biofunctional characteristics', Biomacromolecules, vol. 7, No. 11, pp. 3019-3029, Nov. 2006.
Bott, K. et al.: 'The effect of matrix characteristics on fibroblast proliferation in 3D gels', Biomaterials, vol. 31, No. 32, pp. 8454-8464, Nov. 2010.
Loessner, D. et al.: 'Bioengineered 3D platform to explore cell-ECM interactions and drug resistance of epithelial ovarian cancer cells', Biomaterials, vol. 31, No. 32, pp. 8494-8506, Nov. 2010.
Murphy, W. et al.: 'Hydrogel Compositions for Use in Promoting Tubulogenesis', WO2015157732 (A1), Oct. 15, 2015,
Raza, A. et al.: 'The influence of matrix properties on growth and morphogenesis of human pancreatic ductal epithelial cells in 3D', Biomaterials, vol. 34, No. 21, pp. 5117-5127, Jul. 2013,
Enemchukwu, N. O. et al.: 'Bioartifical matricies to modulate epithelial morphogenesis', Georgia Institute of Technology, 2013.
Levison, S. et al.:'Growth Matrices for Stem Cell Propagation in Vitro and in Tissue Regeneration', WO2014117146 (A1), Jul. 31, 2014.
Fadeev, A. et al.: 'Synthetic Surfaces for Culturing Cells in Chemically Defined Media', WO2009099555 (A2), Aug. 13, 2009.
Yin, X. et al.: 'Engineering Stem Cell Organoids', Cell Stem Cell, vol. 18, No. 1, pp. 25-38, Jan. 2016.
Mather, B.D. et al.: 'Michael addition reactions in macromolecular design for emerging technologies', Prog. Polym. Sci., vol. 31, No. 5, pp. 487-531, May 2006.
Van De Wetering, P. et al.: 'Poly(ethylene glycol) hydrogels formed by conjugate addition with controllable swelling, degradation, and release of pharmaceutically active proteins', J. Control. Release Off. J. Control. Release Soc., vol. 102, No. 3, pp. 619-627, Feb. 2005.
Elbert, D. L. et al.: 'Conjugate addition reactions combined with free-radicalcross-linking for the design of materials for tissue engineering', Biomacromolecules,vol. 2, No. 2, pp. 430-441, 2001.
Rizzi, S. C. et al.: 'Recombinant protein-co-PEG networks as cell-adhesive and proteolytically degradable hydrogel matrixes. Part I: Development and physicochemical characteristics', Biomacromolecules, vol. 6, No. 3, pp. 1226-1238, Jun. 2005.
Pritchard, C. D. et al.: 'An injectable thiol-acrylate poly(ethylene glycol) hydrogel for sustained release of methylprednisolone sodium succinate', Biomaterials, vol. 32, No. 2, pp. 587-597, Jan. 2011.
Metters, A. et al.: 'Network formation and degradation behavior of hydrogels formed by Michael-type addition reactions', Biomacromolecules, vol. 6, No. 1, pp. 290-301, Feb. 2005.
Lutolf, M. P. et al.: 'Cell-Responsive Synthetic Hydrogels', Adv. Mater., vol. 15, No. 11, pp. 888-892, Jun. 2003.
Pratt, A. B. et al.: 'Synthetic extracellular matrices for in situ tissue engineering', Biotechnol. Bioeng., vol. 86, No. 1, pp. 27-36, Apr. 2004.
Phelps, E. A. et al.: 'Maleimide cross-linked bioactive PEG hydrogel exhibits improved reaction kinetics and cross-linking for cell encapsulation and in situ delivery', Adv. Mater. Deerfield Beach Fla, vol. 24, No. 1, pp. 64-70, Jan. 2, 2012.

(56) References Cited

OTHER PUBLICATIONS

Garcia, A. J. et al.: 'PEG-Maleimide Hydrogels for Protein and Cell Delivery in Regenerative Medicine', Ann. Biomed. Eng., vol. 42, No. 2, pp. 312-322, Feb. 2014.
Fu, Y. et al.: 'In situ forming poly(ethylene glycol)-based hydrogels via thiolmaleimide Michael-type addition', J. Biomed. Mater. Res. A, vol. 98, No. 2, pp. 201-211, Aug. 2011.
Zhou, H. et al.: 'Counting primary loops in polymer gels', Proc. Natl. Acad. Sci., vol. 109, No. 47, pp. 19119-19124, Nov. 2012.
Shikanov, A. et al.: 'Hydrogel network design using multifunctional macromers to coordinate tissue maturation in ovarian follicle culture', Biomaterials, vol. 32, No. 10, pp. 2524-2531, Apr. 2011.
Kim, J. et al.: 'Characterization of the crosslinking kinetics of multi-arm poly(ethylene glycol) hydrogels formed via Michael-type addition', Soft Matter, vol. 12, No. 7, pp. 2076-2085, Feb. 2016.
Hersel, U. et al.: 'RGD modified polymers: biomaterials for stimulated cell adhesion and beyond', Biomaterials, vol. 24, No. 24, pp. 4385-4415, Nov. 2003.
Raeber, G. P. et al.: 'Molecularly Engineered PEG Hydrogels: A Novel Model System for Proteolytically Mediated Cell Migration', Biophys. J., vol. 89, No. 2, pp. 1374-1368, Aug. 2005.
Fittkau, M. H. et al.: 'The selective modulation of endothelial cell mobility on RGD peptide containing surfaces by YIGSR peptides', Biomaterials, vol. 26, No. 2, pp. 167-174, Jan. 2005.
Lutolf, M. P. et al.:'Synthesis and physicochemical characterization of endlinked poly(ethylene glycol)-co-peptide hydrogels formed by Michael-type addition', Biomacromolecules, vol. 4, No. 3, pp. 713-722, Jun. 2003.
Kim, W. H. et al: 'Laminin-alpha1-chain sequence Leu-Gln-Val-Gln-Leu-Ser-Ile-Arg (LQVQLSIR) enhances murine melanoma cell metastases', Int. J. Cancer, vol. 77, No. 4, pp. 632-639, Aug. 1998.
Woods, A. et al.: 'A synthetic peptide from the COOH-terminal heparin-binding domain of fibronectin promotes focal adhesion formation', Mol. Biol. Cell, vol. 4, No. 6, pp. 605-613, Jun. 1993.
Drake, S. L. et al.: 'Structural features of fibronectin synthetic peptide FN-C/H II, responsible for cell adhesion, neurite extension, and heparan sulfate binding', J. Biol. Chem., vol. 268, No. 21, pp. 15859-15867, Jul. 1993.
Massia, S. P. et al.: 'Vascular endothelial cell adhesion and spreading promoted by the peptide REDV of the IIICS region of plasma fibronectin is mediated by integrin alpha 4 beta 1', J. Biol. Chem., vol. 267, No. 20, pp. 14019-14026, Jul. 1992.
Herten, M. et al.:'Biodegradation of different synthetic hydrogels made of polyethylene glycol hydrogel/RGD-peptide modifications: an immunohistochemical study in rats', Clin. Oral Implants Res., vol. 20, No. 2, pp. 116-125, Feb. 2009.
Klim, J. R. et al.: 'A defined glycosaminoglycan-binding substratum for human pluripotent stem cells', Nat. Methods, vol. 7, No. 12, pp. 989-994, Dec. 2010.
Santiago, L. Y. et al.: 'Peptide-surface modification of poly(caprolactone) with laminin-derived sequences for adipose-derived stem cell applications', Biomaterials, vol. 27, No. 15, pp. 2962-2969, May 2006.
Nomizu, M. et al.: 'Structure-activity study of a laminin alpha 1 chain active peptide segment Ile-Lys-Val-Ala-Val (IKVAV)', FEBS Lett., vol. 365, No. 2-3, pp. 227-231, May 1995.
Renner, C. et al.: 'Synthetic heterotrimeric collagen peptides as mimics of cell adhesion sites of the basement membrane', Biopolymers, vol. 76, No. 1, pp. 34-47, 2004.
Zhu, J. et al.: 'Design properties of hydrogel tissue-engineering scaffolds', Expert Rev. Med. Devices, vol. 8, No. 5, pp. 607-626, Sep. 2011.
Randell, S. et al.: 'Methods in Molecular Biology: Epithelial cell culture protocols,' vol. 945. 2013.
Lancaster, M. A. et al.: 'Organogenesis in a dish: modeling development and disease using organoid technologies', Science, vol. 345, No. 6194, p. 1247125, Jul. 2014.
Kovbasnjuk, O. et al.: 'Human enteroids: preclinical models of non-inflammatory diarrhea', Stem Cell Res. Ther., vol, 4, No. Suppl 1, p. S3, Dec. 2013.
Wang, Y. et al.: 'Capture and 3D culture of colonic crypts and colonoids in a microarray platform', Lab. Chip, vol. 13, No. 23, pp. 4625-4634, Dec. 2013.
Sato, T. et al.: 'Single Lgr5 stem cells build crypt-villus structures in vitro without a mesenchymal niche', Nature, vol. 459, No. 7244, pp. 262-265, May 2009.
Yin, X. et al. 'Nicheindependent high-purity cultures of Lgr5+ intestinal stem cells and their progeny', Nat. Methods, vol. 11, No. 1, pp. 106-112, Jan. 2014.
Durst, et al. "Flexural characterization of cell encapsulated PEGDA hydrogels with applications for tissue engineered heart valves" Acta Biomater. Jun. 2011 ; 7(6): 2467-2478. doi:10.1016/j.actbio.2011.02.018.

* cited by examiner

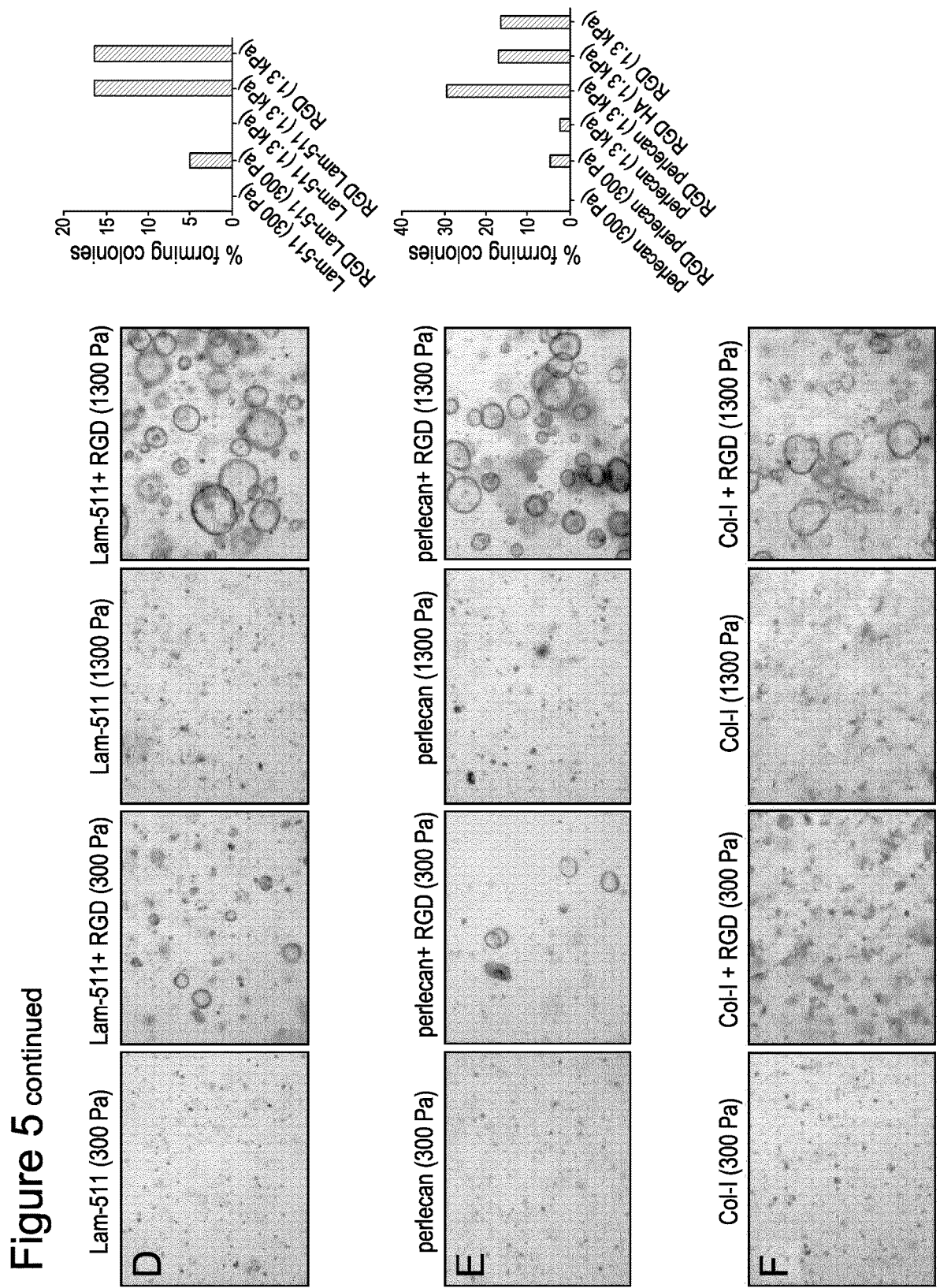

A

B

C

D

A

B

THREE DIMENSIONAL HYDROGELS FOR CULTURING ORGANOIDS

RELATED APPLICATIONS

The present invention is a U.S. National Stage under 35 USC 371 patent application, claiming priority to Serial No. PCT/EP2016/070880, filed on 5 Sep. 2016; which claims priority of PCT/EP2015/070143, filed on 3 Sep. 2015, the entirety of both of which are incorporated herein by reference.

FIELD OF THE INVENTION

The invention provides hydrogels for three-dimensional (3D) culture of adult epithelial cells and uses thereof. Aspects of the invention provide methods for growing epithelial cells on hydrogels and obtaining epithelial cell organoids from stem cells and tumor cells.

BACKGROUND OF THE INVENTION

The worldwide prevalence of intestinal diseases, including inflammatory bowel disease and cancers of the gastrointestinal (GI) tract, traumatic injuries and congenital malformations in newborns presents a critical need for both new therapies and organ transplants. Owing to donor shortage and technical limitations, only approximately 200 allogeneic intestinal transplants occur each year [1]. Likewise, 90% of compounds identified by high-throughput screening fail to progress beyond phase I clinical trials, and a further 90% fail to become new drugs [2]. This high attrition rate has been attributed to the heavy reliance of preclinical translational research on immortalized cell lines and animal models that do not accurately mimic human physiology [2].

Organoids

The recently introduced stem cell-derived GI organoids hold promise as basic experimental models, as sources of transplantable tissue and as physiologically relevant platforms for drug screening. Unlike cultures of immortalized cells, intestinal organoids, for example, contain viable stem cells that reside in crypt-like protrusions and undergo continuous cycles of self-renewal and differentiation to produce multiple functional cell types, thus recapitulating key aspects of intestinal development and homeostasis.

Importantly, epithelial organoids have also been established from human colon, adenoma and adenocarcinoma tissues [3], opening up exciting possibilities for personalized medicine and autologous transplants using patient-derived crypts or stem cells cultured and expanded ex vivo. The feasibility of such endeavours was recently demonstrated in mice: colonic epithelium expanded from a single stem cell was successfully reintroduced into a superficially damaged colon, where it underwent full engraftment, reconstituting tissue structure and function [4]. Despite their previously unmatched histological fidelity to native organs, stem cell-derived organoids of the GI tract suffer several limitations, primary of which is the reliance on Matrigel [5] as a 3D scaffold.

Matrigel is a commercial product widely used to provide the 3D scaffold for the growth of organoids of all cell types [5]. It is used to grow intestinal [6], retinal [7], [8], kidney [9], liver [10], gastric [11], prostate [12], mammary [13]-[15], inner ear [16], cardiac myofiber [17], liver endothelial [18], pancreatic [19], fallopian tube [20] and cerebral [21] organoids. It is also used to grow organoids from a range of species, including chicken [6], rat [22] and human [15], [19], [21].

However, the reliance on Matrigel, or similar naturally derived biopolymer matrices, as the scaffold for organoid growth introduces a number of significant limitations into the study and use of the resultant organoids. Matrigel is derived from a basement membrane ECM-rich mouse sarcoma [5] and therefore introduces a significant risks of immunogen or pathogen transfer if given to a patient, especially problematic in a field in which significant patient mortality and morbidity is associated with infections following immunosuppression. Additionally, the batch-to-batch variability of Matrigel may lead to inconsistent cell behaviours, introducing unknown and potentially confounding variables that complicate the interpretation of both basic and translational research. Furthermore, although Matrigel is a crucial component of current organoid culture models, its role in organoid formation has not yet been ascertained [4]. Reports have implicated the microenvironment in general, and the extracellular matrix (ECM) in particular, in the regulation of intestinal development and function. However, the specific roles of micro-environmental factors are difficult to ascertain using Matrigel given that its molecular components cannot be readily manipulated. Furthermore, although embryonic and adult stem cells alike are known to be profoundly influenced by their mechanical environment [23], performing controlled mechanical modulations within mouse models or Matrigel-based culture is currently not possible. It is therefore unclear whether Matrigel serves merely as a passive 3D scaffold providing physical support to the growing organoid, or actively influences organoid formation by providing essential biological cues. Therefore, whilst Matrigel has facilitated significant advances and developments in the organoid field, current reliance on this 3D scaffold for organoid growth severely limits further development of the field.

Using Synthetic Hydrogels to Grow and Differentiate Cells

Owing to their chemically defined and versatile composition, synthetic ECM analogues (synthetic hydrogels, hereafter "hydrogels") are considered attractive cell culture alternatives to natural, animal-derived matrices such as Matrigel [24]. Indeed, hydrogels have been widely used for supporting cell proliferation, maintenance and differentiation [25]. It is known in the art that RGD functionalised PEG hydrogels with a low or high shear modulus are capable of supporting cell proliferation of cell lines:

Halstenberg et al. [26] describes the use of RGD and heparin functionalised 10-15% PEG-Acr hydrogels with high elastic moduli (1.2 kPa) for supporting proliferation of a human foetal foreskin fibroblast (HFFF) cell line.

WO03/040235, Lütolf et al. [27] describes the use of RGD functionalised 8-10% PEG-VS hydrogels with high elastic moduli (7.5-12.5 kPa) for supporting proliferation of a HFFF cell line.

Rizzi et al. [28] describes the use of RGD functionalised PEG-VS hydrogels with low elastic moduli (0.1-0.5 kPa) for supporting proliferation of a HFFF cell line.

Hydrogels with low shear moduli have been used for the proliferation and maintenance of primary cells and stem cells:

Bott et al. [29] describes the use of RGD functionalised 1.5-2.5% PEG hydrogels with low sheer moduli (0.25-0.7 kPa) to support the proliferation and maintenance of primary human dermal fibroblasts (HDF).

Loessner et al. [30] describes the use of RGD functionalised 1.5-2.5% PEG hydrogels with low elastic moduli (0.2-1.2 kPa) to support the proliferation and maintenance of human epithelial stem cells (hESCs) and induced pluripotent stem cells (IPSCs).

WO2015/157732, Murphy et al. [31] discloses the use of RGD functionalised PEG-VS hydrogels with low elastic moduli (0.26-3.2 kPa) to support the proliferation and maintenance of embryonic stem cell derived retinal pigmented epithelial (RPE) cells and HuVECs.

Raza et al. 2013 [32] describes the proliferation and morphogenesis of a pancreatic ductal immortalised epithelial cell line (PANC-1), on 5% wt 4-arm 5-norbornene-2-carboxylic acid functionalised (NB)PEG hydrogels in which the NB-PEG is crosslinked with MMP target sequence containing peptides. The hydrogels have high elastic moduli (3-6 kPa) and are produced by exposure to UV light.

Enemchukwu 2013 [33] describes the use of 3.5% RGD functionalised PEG hydrogels to support growth MDCK epithelial cell line into cell clusters.

The physical characteristics of hydrogels used for this purpose are not always determined by the investigators:

WO2014/117146, Levison et al. [34] describes RGD functionalised chitosan matrix hydrogels for supporting the growth of hESCs and iPSCs.

WO2009/099555, Fadeev et al. [35] discloses the use of poly(acrylate) hydrogels functionalised with RGD and laminin-derived peptides for supporting the proliferation and maintenance of cardiomyocytes derived from hESCs. Fadeev does not describe the predicted physical characteristics of these hydrogels.

Although synthetic hydrogels have been used extensively for culturing, expanding, proliferating and differentiation of various cell types, recreating epithelial stem cell morphogenesis and growing epithelial cell organoids from stem cells within these matrices has not been accomplished. Indeed, it is believed that although synthetic hydrogels provide sufficient support for cell proliferation and differentiation of cell lines, the microenvironment provided by the currently available hydrogels lacks the mechanical requirements and biochemical complexity required for organoid formation from stem cells [36].

Methods of Producing Hydrogels

Hydrogels can be formed by free-radical polymerization of ester-containing polymer precursors or via 'bio-click' reactions such as Michael-type addition of nucleophile precursors onto unsaturated groups. Unlike free-radical polymerization, Michael-type addition crosslinking does not require cytotoxic free-radicals or UV light [37]. Moreover, hydrogel networks can be formed under physiological conditions that allow for their biofunctional modification, for example through incorporation of integrin-binding (RGD) or protease-sensitive peptides. PEG-co-peptide hydrogels formed by thiol Michael-type addition reactions between multi-functional peptides and acrylate [8], [15]-[19], vinylsulfone [20]-[22], and maleimide [45]-[47] determinate multi-arm PEG macromers have been described.

SUMMARY OF THE INVENTION

The present invention relates to a method for obtaining an epithelial cell organoid, comprising culturing cells in a biofunctional 3D hydrogel, wherein:
a) the cells comprise isolated tissue or organoid fragments and wherein the cells are cultured in conditions suitable for organoid formation; or
b) the cells comprise single or clusters of stem cells, and wherein the cells are first cultured in conditions suitable for cell expansion and subsequently cultured in conditions suitable for organoid formation, wherein the hydrogel comprises a crosslinked hydrophilic polymer and a bioactive molecule, wherein the functional molecule is laminin-111 or a functional variant thereof, and wherein the hydrogel has a shear modulus between 0.05-0.5 kPa, preferably between 0.05-0.3 kPa, more preferably 0.08-0.3 kPa, or most preferably 0.2-0.3 kPa or most preferably 0.08-0.15 kPa.

The growth of epithelial organoids using synthetic hydrogels has not previously been described (Yin et al., page 32, column 1 [36]). The present invention provides the first demonstration of epithelial cell morphogenesis and organoid formation from stem cells on synthetic hydrogels. Certain of the Examples described herein demonstrate that organoids may be grown on hydrogels with relatively low elastic moduli. Certain examples further demonstrate that epithelial organoids can be grown from single or small clusters of stem cells in dynamic hydrogels which degrade over time.

Prior to the present invention, it was believed that RGD containing peptides were necessary components of biofunctional hydrogels for epithelial organoid culture. However, the present invention relates in part to the surprising discovery that laminin-111 and functional variants thereof can support epithelial cell growth in hydrogels even in the absence of an RGD containing peptide.

In a further aspect, the invention provides a three-dimensional hydrogel for culturing adult epithelial stem cells comprising a cross-linked hydrophilic polymer functionalized with an RGD-containing peptide, wherein the concentration of the RGD-containing peptide is of at least 0.05% w/v, and wherein the hydrogel has a shear modulus of 0.5 to 5 kPa.

In a further aspect, the invention provides a method for expanding adult epithelial stem cells, the method comprising encapsulating single cells or multicellular clusters in the three-dimensional hydrogel of the invention and culturing the cells under suitable stem cell expansion conditions.

In a further aspect, the invention provides a method for culturing and expanding normal epithelial organoids, the method comprising: i) encapsulating fragments of epithelial organoids in the three-dimensional hydrogel of the invention, and culturing the organoids under suitable organoid formation conditions, or ii) encapsulating single or clusters of epithelial stem cells in the three-dimensional hydrogel of the invention, expanding the cells under suitable stem cell expansion conditions and subsequently switching to suitable organoid formation conditions.

In a further aspect, the invention provides a method for culturing and expanding epithelial tumor-derived organoids, the method comprising encapsulating tumor-derived single cells or multicellular clusters in the three-dimensional hydrogel of the invention, expanding the cells under suitable cell expansion conditions and subsequently switching to suitable organoid formation conditions.

In a further aspect, the invention provides a method for epithelial tissue regeneration comprising a) encapsulating and expanding of patient-derived epithelial stem cells or organoids in the three-dimensional hydrogel of the invention under suitable stem cell expansion conditions or suitable organoid formation conditions, and b) transplanting the expanded stem cells or organoids back into the patient.

In a further aspect, the invention provides a method for studying intestinal stem cell self-renewal and colony formation, the method comprising encapsulating intestinal stem cells in the three-dimensional hydrogel of the invention and culturing the cells under suitable stem cell expansion conditions.

In a further aspect, the invention provides a method for studying intestinal stem cell differentiation, intestinal tissue polarization and morphogenesis, the method comprising: i) encapsulating fragments of intestinal organoids in the three-dimensional hydrogel of the invention, and culturing the organoids under suitable organoid formation conditions, or ii) encapsulating single or clusters of intestinal stem cells in the three-dimensional hydrogel of the invention, expanding the cells under suitable self-renewal conditions and subsequently switching to suitable organoid formation conditions.

In a further aspect, the invention provides a method for screening of libraries of pharmacologic compounds, biomolecules or evaluating cell-based therapies for efficacy in inducing tumor cell death or growth arrest, the method comprising i) encapsulating tumor cells or organoids in the three-dimensional hydrogel of the invention and culturing the cells or organoids under suitable conditions in the presence of the pharmacologic compounds, biomolecules or cells to be tested, and ii) monitoring cell death and/or growth arrest.

In a further aspect, the invention provides a method for screening of libraries of pharmacologic compounds or biomolecules for efficacy in treating intestinal diseases, the method comprising i) providing intestinal biopsy sample from a patient, ii) encapsulating and growing the intestinal biopsy sample in the three-dimensional hydrogel of the invention and culturing the biopsy sample under suitable conditions in the presence of the pharmacologic compounds or biomolecules to be tested, and iii) in the case of cystic fibrosis, assessing the successful function restoration of the cystic fibrosis transmembrane conductance regulator (CFTR) by means of monitoring Forskolin-induced organoid swelling; iv) in the case of inflammatory bowel disease, monitoring the successful reduction in inflammation, cell damage or death, or restoration of epithelial junction integrity.

In a further aspect, the invention provides a kit of parts for making discrete volumes of the three-dimensional hydrogel according to the invention, comprising the following components a) one or more hydrophilic precursor polymers; b) fibronectin, a fibronectin analogue or a fibronectin-derived fragment; c) a crosslinking agent for the precursor polymers a); and d) laminin-111, laminin-111 analogue or laminin-111 fragment.

DETAILED DESCRIPTION OF THE INVENTION

Brief Description of the Figures

FIG. 1A shows the stage-specific microenvironmental requirements that need to be met to build intestinal organoids within synthetic hydrogels, starting from a single stem cell. FIG. 1B-C show intestinal crypts 48 hours after extraction and encapsulation into Matrigel (FIG. 1B) or plain PEG (FIG. 1C). Asterisks indicate dead crypts, arrows indicate crypts that have survived and are reorganizing into round colonies.

FIG. 2A shows the key ECM components that constitute the mouse small intestinal basement membrane. Laminin-111 and fibronectin are enriched near the crypt base, whereas the hyaluronic acid receptor CD44 is expressed specifically by ISCs. FIG. 2B-E show the effect of laminin-based adhesion on organoid culture within synthetic matrices. FIG. 2B: The effect of different laminin-111-derived sequences on organoid viability. FIG. 2C: Morphology of organoids grown in Matrigel, plain PEG or PEG-AG73. FIG. 2D: AG73-conjugated PEG matrices significantly enhance the growth of organoids. FIG. 2E: The effect of AG73 on organoid viability and growth is concentration-dependent.

FIG. 3A shows ISC colony formation and Lgr5-EGFP expression in modified hydrogels. Modified PEG hydrogels were prepared at different precursor concentrations. FIG. 3B shows the morphology and Lgr5-EGFP expression in intestinal organoids grown in Matrigel and MT PEG-AG73 gels. FIG. 3C shows quantification of Lgr5-EGFP expression in intestinal organoids expanded in Matrigel, TG PEG-AG73 and MT PEG-AG73. FIG. 3D shows quantification of intestinal organoid viability in Matrigel, TG PEG-AG73 and MT PEG-AG73. FIG. 3E shows the establishment of apicobasal polarity. FIG. 3F shows the presence of Paneth (lysozyme) and goblet (mucin) cells within organoids grown in MT PEG-AG73. FIG. 3G-I shows intestinal crypt morphology 24 h after embedding in PEG-RGD alone (FIG. 3G), or in the presence of AG73 (FIG. 3H) or hyaluronic acid (HA) (FIG. 3I). Asterisks indicate dead crypts, arrows indicate crypts that have survived and are reorganizing into round colonies. FIG. 3J shows the Matrigel-free culture of ISCs. Freshly isolated intestinal crypts survive in PEG-RGD and form expanding ISC colonies, which can be passaged and expanded further. FIGS. 3K and L show ISC expansion in Wnt3a-containing medium. Recombinant Wnt3a can successfully replace CHIR99021 and VPA for the expansion of ISCs. FIG. 3M shows rheological characterisation of MT PEG-AG73 gels of varying PEG content.

FIGS. 4E and 4F show the morphology and Lgr5-EGFP expression of intestinal organoids formed by ISCs expanded in Matrigel (FIG. 4F) or PEG-RGD (FIG. 4E). Asterisks indicate autofluorescence, white arrows indicate Lgr5-EGFP signal. FIG. 4G shows polarization and presence of Paneth (lysozyme) and goblet (mucin) cells in organoids formed by ISCs expanded in Matrigel or PEG-RGD. Fig H shows intestinal marker expression in PEG- and Matrigel-based ISC and organoid culture. Plots show mRNA levels of key intestinal genes: Lgr5 (ISCs), ALPI (enterocytes), Chr-A (enteroendocrine cells), Muc-2 (goblet cells) and Lyz (Paneth cells). FIG. 4I-L show the effect of integrin-based adhesion and gel stiffness on ISC colony formation. FIG. 4I shows ISC colonies in 700 Pa PEG matrices presenting varying concentrations of RGD ligand. FIG. 4K shows ISC colonies in PEG-RGD matrices of a constant (1 mM) RGD concentration and varying stiffness. FIG. 4J shows quantification of ISC colony formation efficiency as a function of RGD concentration. FIG. 4L shows quantification of ISC colony formation efficiency as a function of matrix stiffness.

FIG. 6A: Laminin-111 supports ISC colony formation within soft matrices. Colonies formed in soft, laminin-containing matrices are able to form organoids (FIG. 6B) which contain the four differentiated cell types of the intestinal epithelium: L-FABP (enterocytes), Chr-A (enteroendocrine cells), Muc-2 (goblet cells) and Lyz (Paneth cells) (FIG. 6C). FIG. 6D shows intestinal organoids formed from single ISCs grown in soft, laminin-containing PEG gels.

FIG. 7A: Colony formation efficiency of ISCs embedded in degradable (DG) or non-degradable (N-DG) PEG gels of varying stiffness. FIG. 7B-C: The effect of matrix degradability on ISC colony shape was quantified by morphometric analysis of circularity. FIG. 7D: Fluorescent image showing the expression and distribution of E-cadherin and F-actin within colonies grown in degradable and non-degradable matrices. FIG. 7E: Quantification of the percent of columnar and polarized colonies as a function of matrix degradability. FIG. 7F-G: Lgr5-EGFP expression within colonies cultured in degradable and non-degradable matrices and quantification. FIG. 7H: ISO colonies expanded in degradable or non-degradable PEG gels and transferred to Matrigel for further culture under organoid formation conditions. FIG. 7I: Quantification of the organoid formation capacity of ISO colonies grown in degradable or non-degradable matrices.

FIG. 8A: Bright field images showing morphology and Lgr5-EGFP expression in ISO colonies 2 days after switching to differentiation conditions. FIG. 8B: Intestinal organoid morphology in PEG-Matrigel composites of constant biochemical composition, but varying mechanical properties. FIG. 8C: Quantification of intestinal organoid viability in PEG-Matrigel composites of varying mechanical properties. FIG. 8D shows that laminin-111 is required for organoid formation, alongside a soft (<200 Pa) matrix. AG73, fibronectin/RGD, hyaluronic acid and perlecan failed to support ISC colony differentiation and organoid formation. FIG. 8E: Mechanical characterization of hybrid PEG-Acr/PEG-VS matrices at the day of formation and four days later. The first number indicates the percentage of PEG-Acr polymer in the gels (relative to PEG-VS), whereas the second number indicates the overall PEG polymer content of the gels (w/v). FIG. 8F: ISC colonies expanded in PEG-Acr/PEG-VS hybrid matrices for 4 days. Insets depict Lgr5-EGFP. FIG. 8G: ISC colonies expanded in PEG-Acr/PEG-VS hybrid matrices for 4 days and subsequently cultured under differentiation/organoid formation conditions for additional 2 days. FIG. 8H: Immunofluorescence analysis of organoids expanded in 75% PEG-Acr/PEG-VS for lysozyme (Paneth cells) and mucin-2 (goblet cells).

FIG. 9A: Mouse pancreatic ducts embedded in PEG-RGD and cultured for 2 days. FIG. 9B: Mouse pancreatic organoids obtained from the dissociation and re-embedding of the ducts shown in FIG. 9A. FIG. 9C: Mouse pancreatic organoids in PEG-RGD matrices of varying stiffness. FIG. 9D: Quantification of pancreatic organoid formation efficiency as a function of matrix stiffness.

FIG. 10A: Mouse colon adenoma organoids in PEG-RGD matrices of varying stiffness, and quantification of colon adenoma organoid formation efficiency as a function of matrix stiffness. FIG. 10B: Human patient-derived colorectal cancer organoids grow efficiently in soft and stiff matrices, with or without RGD.

DEFINITIONS

Figure 1:
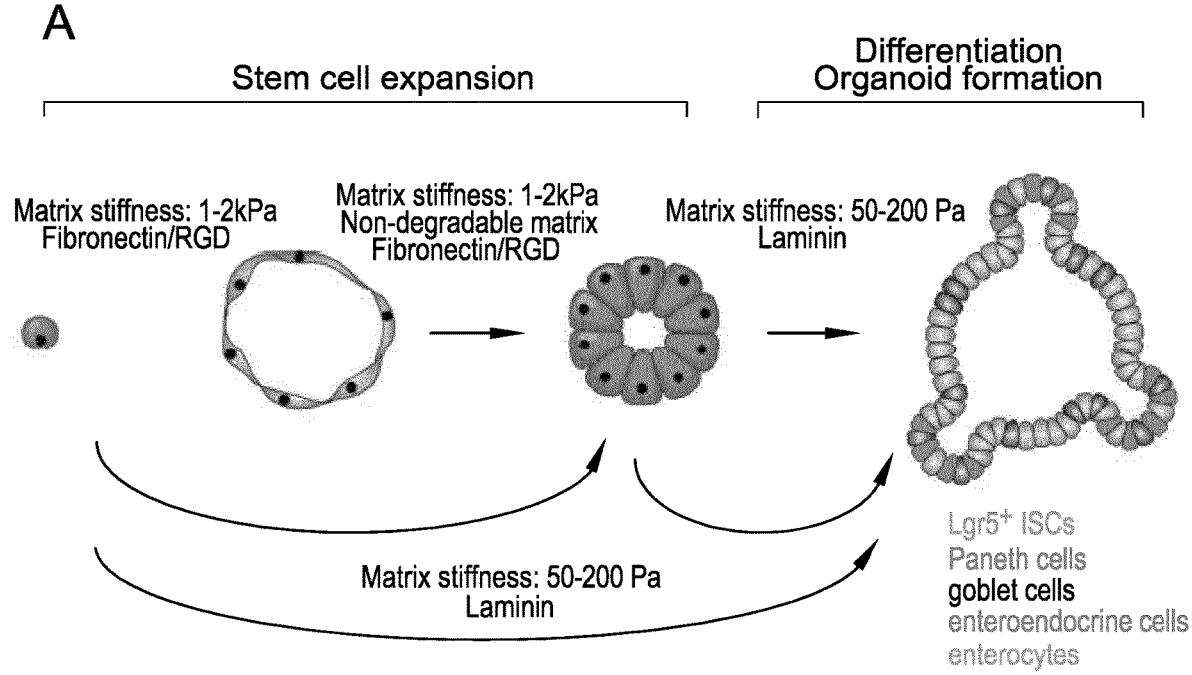
FIG. 1.
Figure 1:
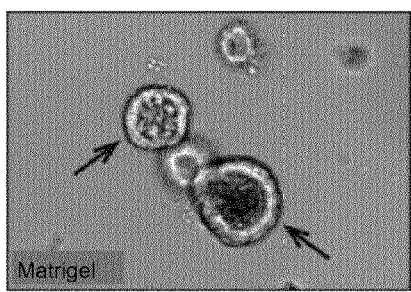
Figure 1:
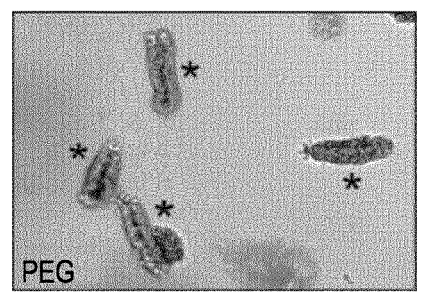

AG73 (RKRLQVQLSIRT, SEQ ID NO: 1) is a synthetic peptide derived from the globular domain of the laminin α1 chain [55].

As used in the specification and claims, the term "and/or" used in a phrase such as "A and/or B" herein is intended to include "A and B", "A or B", "A", and "B".

A hydrogel (gel) is a matrix comprising a network of hydrophilic polymer chains.

A biofunctional hydrogel is a hydrogel that contains bio-adhesive (or bioactive) molecules, and/or cell signalling molecules that interact with living cells to promote cell viability and a desired cellular phenotype. Biofunctional hydrogels may also be referred to as bioactive. Examples of bio-adhesive molecules include, but are not limited to, fibronectin [56]-[59], vitronectin [60], bone sialoprotein [60], laminin [61], [62], collagen [63] and elastin. These molecules contain cell adhesive peptides that govern their interaction with cells. Examples of cell adhesion peptide sequences include, but are not limited to fibronectin-derived RGD, KQAGDV (SEQ ID NO: 15), REDV (SEQ ID NO: 16) and PHSRN (SEQ ID NO: 17), laminin-derived YIGSR (SEQ ID NO: 18), LGTIPG (SEQ ID NO: 19), IKVAV (SEQ ID NO: 20), PDGSR (SEQ ID NO: 21), LRE, LRGDN (SEQ ID NO: 22) and IKLLI (SEQ ID NO: 23), collagen-derived DGEA (SEQ ID NO: 24) and GFOGER (SEQ ID NO: 25), and elastin-derived VAPG (SEQ ID NO: 26) [64].

Bio-adhesive (or biofunctional, or bioactive) molecules that interact with epithelial cells to promote epithelial cell viability, have been previously described [30], [31]. Bio-adhesive molecules that render a hydrogel biofunctional include, but are not limited to, fibronectin or functional variants thereof, for example FF $III_1$-C fragment, FNIII9-10 fragment, and FNIII12-14, or RGD containing peptides, for example RGD, RGDS (SEQ ID NO: 11), RGDSP (SEQ ID NO: 2), RGDSPK (SEQ ID NO: 3), RGDTP (SEQ ID NO: 4) and RGDSPASSKP (SEQ ID NO: 5). Functional variants of bioactive molecules are molecules having the same or similar biological or biochemical function and a similar sequence or composition—for example, truncated molecules, or fragments of such molecules.

A biocompatible hydrogel is a polymer network that is not significantly toxic to living tissue and/or cells, and does not elicit an immunopathogenic response in healthy individuals. A biocompatible active mechanism is a process that is not toxic to particular cells or tissues, for example a temperature increase within the physiological temperature range of tissues, or that is applied briefly enough so as not to cause significant toxicity.

"Crosslinkable by cell-compatible reaction(s)" means that molecules are cross-linkable by reactions which are not significantly toxic to living tissue and/or cells. Such reactions may include (i) permanent covalent bond formation, chosen from the group consisting of a) enzymatically catalyzed reactions, preferably depending on activated transglutaminase such as factor XIIIa; and b) not-enzymatically catalyzed and/or uncatalyzed reactions, preferably a Michael addition reaction; and/or ii) reversible covalent bond formation, chosen from the group consisting of Schiff base (imine) bonds, reversible hydrazone bonds, oxime bonds, disulfide bonds and bonds formed by reversible Diels-Alder reactions; and/or iii) non-covalent (i.e. physical) bond formation (e.g. on the basis of hydrophobic interactions, H-bonds, van-der-Waals, electrostatic interactions, host-guest interactions, biorecognition (domain/protein-ligand interactions); spontaneous or induced by temperature changes or changes in ionic strength of a buffer).

As used herein, "a cross-linked hydrophilic polymer functionalized with RGD-containing peptide" refers to the incorporation of a peptide containing the amino acid sequence "RGD" into a hydrogel by crosslinking between the hydrophilic polymer of the hydrogel and the RGD-containing peptide.

Culturing cells refers to the process of keeping cells in conditions appropriate for maintenance and/or growth, where conditions refers to, for example, the temperature, nutrient availability, atmospheric $CO_2$ content and cell density in which the cells are kept. Cells can be cultured in vivo or in vitro. The appropriate culturing conditions for maintaining, proliferating, expanding and differentiating different types of epithelial cells are well-known and documented [65]. The conditions suitable for organoid formation are those that facilitate or permit cell differentiation and the formation of multicellular structures. See Materials and Methods for details of culturing conditions suitable for epithelial cell expansion and organoid formation.

Hydrolysis refers to breaking a bond through an interaction with water. A hydrolytically non-degradable component of a hydrogel is unsusceptible to breakdown by a reaction with water.

Laminins are a family of extracellular matrix glycoproteins that have a heterotrimeric structure consisting of an α, β and γ chain. Laminin-111 is synonymous with Laminin-1. Laiminin-111 is encoded by the LAMA1 gene.

Matrigel is a commercial product widely used in both 2D and 3D models of cell culture. It comprises a solubilized basement membrane preparation extracted from a ECM rich mouse tumour.

Organoids are three-dimensional culture systems of organ-specific cell types that develop from stem cells and self-organize (or self-pattern) through cell sorting and spatially restricted lineage commitment in a manner similar to the situation in vivo. An organoid therefore represents the native physiology of the cells [66] and is has a cellular composition (including both remaining stem cells, a near-physiological niche, as well as specialized cell types) and anatomy that emulate the native situation. Stem cells may be isolated from tissue or organoid fragments. The cells from which an organoid is generated differentiate to form an organ-like tissue exhibiting multiple cell types that self-organize to form a structure very similar to the organ in vivo. Organoids are therefore excellent models for studying human organs and human organ development in a system very similar to development in vivo. Epithelial cell organoids are organoids containing epithelial cells. Organoids grown from isolated intestinal crypts or stem cells may also be referred to in the field as "enteroids" or "colonoids" [67], [68].

The term RGD or RGD sequence refers to a minimal bioactive RGD sequence, which is Arginine-Glycine-Aspartic Acid (RGD) sequence, and which is the smallest (minimal) fibronectin-derived amino acid sequence that is sufficient to mimic cell binding to fibronectin and/or to promote adhesion of the anchorage-dependent cells.

The shear modulus of a hydrogel is equivalent to the modulus of rigidity, G, elastic modulus or elasticity of a hydrogel. The shear modulus is defined as the ratio of shear stress to the shear strain. The shear modulus of a hydrogel can be measured using a rheometer (see Materials and Methods)

The present invention provides hydrogels suitable for supporting epithelial cell expansion, morphogenesis and organoid formation. These hydrogels are based on the micro-environmental properties and components governing the distinct stages of epithelial stem cell-driven organoid formation and maintenance that form part of the present disclosure.

The present invention also provides methods for producing hydrogels suitable for supporting epithelial cell expansion and morphogenesis. By using these methods the technical properties of 3D hydrogels can be adjusted (according to the culturing method for which the hydrogel is required) by varying the hydrophilic polymer content in the hydrogel, as well as the molecular weight and/or functionality (number of sites available for crosslinking) of the polymeric hydrogel precursors as described in the Examples.

These systems offer a fully defined, reproducible environment that can be subjected to controlled biophysical and biochemical modifications, thus opening up new and previously inaccessible directions in basic and clinical research, while also offering the possibility for the large-scale production of clinical-grade intestinal cells and tissues. The materials described here can also be used for the expansion of other normal and transformed epithelial organoids, from both mouse and human origin.

The invention provides the key microenvironmental components that govern distinct stages of epithelial stem cell-driven organoid formation, including intestinal stem cell (ISC) self-renewal, differentiation and morphogenesis (summarized in FIG. 1). This insight was used to create fully defined three-dimensional culture systems for the expansion of intestinal stem cells and organoids, comprising poly (ethylene glycol)-based hydrogels of precise mechanical properties and short synthetic peptide sequences that mimic adhesion to the extracellular matrix. These systems offer a fully defined, reproducible environment that can be subjected to controlled biophysical and biochemical modifications, thus opening up new and previously inaccessible directions in basic and clinical research, while also offering the possibility for the large-scale production of clinical-grade intestinal cells and tissues. The materials described here can also be used for the expansion of other normal and transformed epithelial organoids, from both mouse and human origin.

In some embodiments, the invention provides two fully defined three-dimensional hydrogel systems for intestinal cell culture-one supporting the high-purity expansion of intestinal stem cells (ISCs), and the other supporting both the expansion of ISC colonies and their subsequent differentiation and organoid formation. In designing these hydrogel systems, comprising synthetic PEG-based hydrogels of modular physicochemical properties, the key biophysical and biochemical parameters have been identified, including types and abundance of adhesion ligands and a precisely defined range of mechanical properties, which govern the distinct stages of organoid formation (FIG. 1). The three-dimensional hydrogel system of the invention can be adapted for the culture of other types of adult epithelial stem cells and organoids, normal or tumor-derived. The culture of mouse pancreatic and colon adenoma-derived organoids is exemplified herein. The three-dimensional hydrogel system of the invention can find wide applications as basic research tools for studying epithelial tissue development, physiology and disease, but also as platforms for pharmacologic screens in a chemically defined and reproducible environment. Further, owing to their compatibility with good manufacturing practice (GMP) cell and tissue production, these materials hold clinical promise for cell-based treatment of intestinal disease or injury in humans.

An aspect of the invention provides a three-dimensional hydrogel for culturing adult epithelial stem cells comprising a cross-linked hydrophilic polymer functionalized with an RGD containing peptide, wherein the concentration of the RGD-containing peptide is of at least 0.05% w/v (0.5 mM), and wherein the hydrogel has a shear modulus (stiffness) of 0.5-5 kPa.

The three-dimensional hydrogels of the invention are specifically optimized for the expansion of adult epithelial multipotent stem cells (primarily intestinal, but also colonic, gastric, hepatic, pancreatic, rectal, mammary or lung stem cells). Further, the three-dimensional hydrogels of the invention are also optimized for the expansion of adult epithelial multipotent stem cells (primarily intestinal, but also colonic, gastric, hepatic, pancreatic, rectal, mammary or lung stem cells) and subsequent differentiation and organoid formation.

In some embodiments of the invention, the hydrophilic polymer is selected from the group comprising poly(ethylene glycol), polyoxazoline, polyaliphatic polyurethanes, polyether polyurethanes, polyester polyurethanes, polyethylene copolymers, polyamides, polyvinyl alcohols, poly(ethylene oxide), polypropylene oxide, polypropylene glycol, polytetramethylene oxide, polyvinyl pyrrolidone, polyacrylamide, poly(hydroxy ethyl acrylate), poly(hydroxyethyl methacrylate), or mixtures or co-polymers thereof.

In an embodiment, the hydrogels used, which are obtained by cross-linking hydrogel precursor molecules, are preferably composed of hydrophilic polymers such as poly(ethylene glycol) (PEG)-based polymers, most preferably multiarm (i.e. branched) PEG-based polymers that are crosslinked by cell-compatible crosslinking reactions.

Hydrogel precursors can be selected from a group comprising linear PEG molecules, or multiarm PEG hydrogel precursor molecules, preferably those bearing 4-arms or 8-arms. Hydrogel precursors can be further selected from a group comprising PEG hydrogel precursor molecules with molecular weight of 10-40 kDa.

The hydrophilic polymer content of the hydrogels, swollen to equilibrium in a buffer, can range between 1 and 10% w/v, with a preferred ranges of 2.0 to 4.0%% w/v and 2.5 to 3.5% w/v, optimized for the expansion of ISCs.

In preferred embodiments, PEG-based precursor molecules are chosen such as to be cross-linkable using either thrombin-activated Factor XIIIa under physiological conditions or by another enzymatic crosslinking mechanism known in the art, or via Michael addition or by another mild chemical crosslinking mechanism known in the art. To achieve the preferred FXIIIa-mediated crosslinking, one of at least two hydrogel precursor molecules is functionalized with a lysine-bearing peptide sequence, whereas the other is functionalized with a glutamine-bearing peptide sequence. To achieve the preferred Michael addition-mediated cross-linking, one of the two hydrogel precursor molecules is a multiarm PEG end functionalized with a nucleophilic group, most preferably a thiol, whereas the other is a multiarm PEG end-functionalized with an electrophilic group, most preferably a vinylsulf one or a maleimide.

Cross-linking of the hydrogel precursor molecules is usually done in the presence of cell types to be cultured within the hydrogel, in such a way that the cells or cell aggregates are encapsulated by the forming hydrogel matrix, i.e. are residing in a distinct cell culture microenvironment.

In preferred embodiments of the invention, the RGD-containing peptide is a peptide containing RGD binding motif selected from the group comprising fibronectin, fibronectin analogue or a fibronectin-derived fragment.

In other preferred embodiments, the concentration of the RGD-containing peptide is within the range of 0.05%-1% w/v (0.5-10 mM). In a more preferred embodiment, the concentration of the RGD-containing peptide is 0.1% w/v (1 mM).

In other embodiments of the invention, the fibronectin-derived fragment or fibronectin analogue is a peptide selected from the group comprising RGD, RGDS (SEQ ID NO:11), RGDSP (SEQ ID NO:2), RGDSPK (SEQ ID NO:3), RGDTP (SEQ ID NO:4), RGDSPASSKP (SEQ ID NO:5), Cyclo(RGDSP) (SEQ ID NO:2), Cyclo(RGDFK) (SEQ ID NO:6), Cyclo(RGDYK) (SEQ ID NO:7), Cyclo(RGDFC) (SEQ ID NO:8), or a fragment selected from the group comprising III1-C fragment (Morla et al., 1994), FNIII9-10 fragment, and FNIII12-14 fragment (Martino et al., 2011).

In three-dimensional hydrogels of the invention, the presence of fibronectin, fibronectin analogue or a fibronectin-derived fragment in a quantity sufficient to provide a concentration of RGD sequence of at least 0.05% (0.5 mM), preferably within the range of 0.05%-1% w/v (0.5-10 mM) is indispensable for the survival and proliferation of adult epithelial stem cells. In addition, the range of concentration (0.5-10 mM) is atypically high in the PEG hydrogel field.

Mechanical properties, i.e. stiffness, of the three-dimensional hydrogels according to the invention can be changed by varying the hydrophilic polymer content in hydrogel, as well as the molecular weight and/or functionality (number of sites available for crosslinking) of the polymeric hydrogel precursors.

According to the present invention, colony formation, proliferation and self-renewal of adult epithelial stem cells optimally occurs at shear modulus (stiffness) of 0.5-2.5 kPa, preferably 1.0-1.5 kPa.

In an embodiment of the invention, the three-dimensional hydrogel of the invention has a shear modulus (stiffness) of 0.5-2.5 kPa, preferably 1.0-1.5 kPa. The desired initial stiffness range of 0.5-2.5 kPa, preferably 1.0-1.5 kPa, is achieved by fixing the polymer (PEG) content within the hydrogel to 2.0-4.0% w/v.

In one preferred embodiment, the three-dimensional hydrogel of the invention has hydrophilic polymer content within a range of 2.0-4.0% w/v, the concentration of RGD within a range of 0.05%-1.0% w/v, and the hydrogel has a shear modulus of 0.5 to 2.5 kPa.

In a further preferred embodiment, the three-dimensional hydrogel of the invention with shear modulus (stiffness) of 1.3 kPa and containing RGD at a concentration of 1 mM (0.1% w/v) is an optimal minimal matrix for ISO self-renewal and large-scale expansion.

In any of the embodiments of the invention, the hydrogels may comprise up to 10% Matrigel, or similar naturally derived biopolymer matrices, in addition to the other components described herein. From 1-10%, from 3-10%, from 5-10%, and preferably 10% Matrigel may be used.

In another aspect, the invention provides a three-dimensional hydrogel, which initially provides the stiffness optimal for ISO self-renewal and colony formation (thus allowing ISO expansion), but softens over time to afford ISO colony differentiation and epithelial/intestinal organoid formation and which further contains laminin-111, laminin-111 analogue or laminin-111 fragment. This dynamic three-dimensional hydrogel, slightly modified, can be used to culture other types of mouse and human epithelial stem cells and organoids.

In an embodiment, the three-dimensional hydrogels of the invention have an initial shear modulus (stiffness) of 0.5-5 kPa, preferably 0.5-2.5 kPa and a final shear modulus (stiffness) of 50-200 Pa. The kinetics (time) of the softening is cell type-dependent, but said softening should occur within the time window during which stem cell expansion takes place and before differentiation, epithelial budding and organoid formation begins. For forming budding epithelial organoids starting from epithelial stem cells, it is necessary that the three-dimensional hydrogels of the invention soften, i.e. that an initial shear modulus (stiffness) of 0.5-5 kPa, preferably 0.5-2.5 kPa, decreases to a final shear modulus (stiffness) of 50-200 Pa at the beginning of the differentiation and organoid formation process. According to the invention, a drop in stiffness to below 200 Pa is crucial for the successful initiation of organoid formation.

In a particular embodiment, the three-dimensional hydrogels of the invention have an initial shear modulus (stiffness) of 1-2 kPa and a final shear modulus (stiffness) of 80-150 Pa after 4 days of cell culture.

The softening, i.e. stiffness decrease, of the three-dimensional hydrogel of the invention can be achieved by various strategies known to persons skilled in the art, either by cell-compatible passive strategies, preferably by the incorporation of water-soluble polymers or domains in the polymer backbone that contain hydrolytically labile chemical bonds, preferably poly(ethylene glycol) functionalized with an acrylate group that forms a labile ester bond upon Michael addition with a thiol group, or else by cell-compatible active strategies, preferably by the application of light, the incorporation of artificial cleavage sites, or biodegradable materials such as proteins or sugars that are relatively rare in the extracellular matrix of tissues.

The hydrolytically labile chemical bonds from polymers or domains in the polymer can be selected from a group of polymers comprising poly(a-esters) (e.g. polyglycolide, polylactide, poly(lactide-co-glycolide), polycaprolactone, or poly(propylene fumarate), polyanhydrides, polyacetals, poly(ortho esters), polycarbonates, polyurethanes, polyphosphazenes, polyphosphoesters, polyhydroxyalkanoates, or combinations thereof.

The artificial (i.e. recognized by non-mammalian proteases) cleavage site is preferably the Q/G or Q/S site contained within the sequences ENLYFQG (SEQ ID NO:9) and ENLYFQS (SEQ ID NO:10), and recognized by the Tobacco Etch Virus (TEV) protease.

Hydrogel networks wherein the softening i.e. the stiffness drop is achieved via active light-mediated strategies incorporate photolabile moieties that undergo degradation in response to UV, visible or two-photon light exposure. The photolabile moieties are preferably selected from the o-nitrobenzyl or p-hydroxyphenacyl families, the most preferable ones being onitrobenzyl, dimethoxy nitrobenzyl and hydroxyphenacetyl iodide.

In a particular embodiment, optimized for the formation of small intestinal organoids, the decrease of stiffness can be achieved by a specific formulation of poly(ethylene glycol) (PEG) that consists of PEG-vinyl sulfone (PEG-VS)/PEG-acrylate (PEG-Acr) hybrid at ratio 1:3.

In a further particular embodiment, laminin-111, laminin-111 analogue or laminin-111 fragment is present at a concentration of 5 g/ml-250 g/ml.

In another particular embodiment, the three-dimensional hydrogel of invention further comprising laminin-111, laminin-111 analogue or laminin-111 fragment at concentration of 5 µg/ml to 250 µg/ml, and wherein the hydrophilic polymer is poly(ethylene glycol) (PEG) that consists of PEG-vinyl sulfone (PEG-VS)/PEG-acrylate (PEG-Acr) hybrid at ratio 1:3, and wherein the hydrogel has an initial shear modulus of 0.5 to 2.5 kPa and a final shear modulus of 80-150 Pa after 4 days of cell culture.

However, the necessary decrease in mechanical properties, i.e. stiffness, cannot be achieved by conferring degradation characteristics to the hydrogel via incorporation into the hydrogel of peptides sensitive to cell-secreted proteases such as matrix-metalloproteinases (MMPs) because the proteolytic degradation impairs multiple aspects of epithelial stem cell expansion, differentiation and morphogenesis.

Another aspect of the invention relates to a method of preparing three-dimensional hydrogels of the invention. In particular, this method comprises the steps of a) providing one or more different hydrogel precursor molecules; b) combining and dispensing different combinations of hydrogel precursor molecules according to step a) onto or into discrete volumes of a substrate, preferably a multi-well plate; c) adding to said discrete volumes one or more RGD sequence containing peptide, such as fibronectin, fibronectin analogue or a fibronectin-derived fragment, and either attaching said molecules to at least one of the hydrogel precursor molecules present or the hydrogel formed in step e) or allowing them to diffuse freely; d) optionally adding laminin-111, laminin-111 analogue or laminin-111 fragment e) adding cells onto/into said discrete volumes of the substrate; and f) crosslinking said hydrogel precursor molecules to form a hydrogel.

In step a) of the above described method the hydrogel precursor molecules used are preferably chemically or enzymatically reactive polymeric PEG-based precursor to which biomolecules can be tethered and that can be cross-linked by mechanisms that do not compromise cell viability. If the PEG-based precursors comprise (glutamine-and lysine-bearing) peptidic substrates for a transglutaminase such as e.g. factor XIIIa, crosslinking can be carried out by means of a this enzyme. When mechanical softening over time is necessary, the hydrogel precursor molecules can for example also comprise polymers that contain a labile ester bond in order to facilitate hydrolytic degradation, i.e. localized changes in structural and mechanical properties of the hydrogel over time.

In step e) the cross-linking of the hydrogel precursor molecules to form a three-dimensional hydrogel can be achieved by using at least one cross-linking agent. When PEG-based precursor molecules are used, thrombin-activated Factor XIIIa is the chosen cross-linking agent. However, it is also conceivable that the crosslinking may occur immediately upon combination of two different precursor molecules which are readily reactive towards each other (such as e.g. by highly selective so-called click chemistry or other chemical, not enzymatically catalyzed reaction such as e.g. of the Michael addition reaction).

Another aspect of the invention provides a method for expanding adult epithelial stem cells, the method comprising encapsulating single cells or multicellular clusters in the three-dimensional hydrogel of the invention and culturing the cells under suitable stem cell expansion conditions.

In some preferred embodiments, the cells are intestinal, colonic, gastric, hepatic, pancreatic, rectal, mammary or lung stem cells.

Another aspect of the invention provides a method for culturing and expanding normal (healthy) epithelial organoids, the method comprising: i) encapsulating fragments of epithelial organoids in the three-dimensional hydrogel of the invention, and culturing the organoids under suitable organoid formation conditions, or ii) encapsulating single or clusters of epithelial stem cells in the three-dimensional hydrogel of the invention, expanding the cells under suitable stem cell expansion conditions and subsequently switching to suitable organoid formation conditions.

In some embodiments, the epithelial organoids are intestinal, colonic, gastric, hepatic, pancreatic, rectal, mammary or lung-derived.

Another aspect of the invention provides a method for culturing and expanding epithelial tumor-derived organoids, the method comprising encapsulating tumor-derived single cells or multicellular clusters in the three-dimensional hydrogel of the invention, expanding the cells under suitable cell expansion conditions and subsequently switching to suitable organoid formation conditions.

In some embodiments, the tumor-derived single cells are derived from colorectal, gastric, hepatic, pancreatic, mammary or lung tumors.

Another aspect of the invention provides a method for epithelial tissue regeneration comprising a) encapsulating and expanding of patient-derived epithelial stem cells or organoids in the three-dimensional hydrogel of the invention under suitable stem cell expansion conditions or suitable organoid formation conditions, and b) transplanting the expanded stem cells or organoids back into the patient.

Another aspect of the invention provides a method for studying intestinal stem cell self-renewal and colony formation, the method comprising encapsulating intestinal stem cells in the three-dimensional hydrogel of the invention and culturing the cells under suitable stem cell expansion conditions.

Another aspect of the invention provides a method for studying intestinal stem cell differentiation, intestinal tissue polarization and morphogenesis, the method comprising i) encapsulating fragments of intestinal organoids in the three-dimensional hydrogel of the invention, and culturing the organoids under suitable organoid formation conditions, or ii) encapsulating single or clusters of intestinal stem cells in the three-dimensional hydrogel of the invention, expanding the cells under suitable self-renewal conditions and subsequently switching to suitable organoid formation conditions.

Another aspect of the invention provides a method for screening of libraries of pharmacologic compounds, biomolecules or cells for efficacy in inducing tumor cell death or growth arrest, the method comprising i) encapsulating tumor cells or organoids in the three-dimensional hydrogel of the invention and culturing the cells or the organoids under suitable conditions in the presence of the compound or compounds to be tested, and ii) monitoring cell death and/or growth arrest.

The monitoring of cell death and/or growth arrest is carried out by methods known to the person skilled in the art.

In a further aspect, the invention provides a scalable and reproducible method for adapting the synthetic 3D hydrogel-based culture system for modeling human intestinal diseases such as cystic fibrosis (CF) and inflammatory bowel disease (IBD) in a manner that is amenable for personalized therapy. To this end, organoid systems based on the invention can be employed as screening tools to investigate the effect of pharmacologic compounds or biomolecules on in vitro grown intestinal biopsy samples from individual patients. Such a method for screening of libraries of pharmacologic compounds or biomolecules for efficacy in treating intestinal diseases, the method comprising i) providing intestinal biopsy sample from a patient, ii) encapsulating and growing the intestinal biopsy sample in the three-dimensional hydrogel of the invention and culturing the biopsy sample under suitable conditions in the presence of the pharmacologic compounds or biomolecules to be tested, and iii) in the case of cystic fibrosis, assessing the successful function restoration of the cystic fibrosis transmembrane conductance regulator (CFTR) by means of monitoring Forskolin-induced organoid swelling. iv) in the case of inflammatory bowel disease, monitoring the successful reduction in inflammation, cell damage or death, or restoration of epithelial junction integrity.

In a preferred embodiment, intestinal diseases are selected from the group comprising cystic fibrosis and inflammatory bowel disease.

The three-dimensional hydrogels of the invention are impactful as both basic and translational research tools. Intestine-specific processes, including ISC self-renewal, differentiation, crypt-villus patterning, inflammation and malignant transformation, as well as general epithelial phenomena, including establishment of apicobasal polarity and lumen formation, can be studied in a fully chemically defined and reproducible environment. Keeping in mind the modularity of the PEG hydrogels which serve as the basis for the matrices introduced here, the effects of microenvironmental parameters, including ECM proteins, cell-cell interaction proteins, matrix degradability and mechanical properties, on various aspects of intestinal biology can be elucidated. Furthermore, the chemically defined environment provided by the three-dimensional hydrogels of the invention will be particularly valuable in the context of pharmacologic compound or biomolecules screens, costly large-scale endeavors where reproducibility and reliability are of utmost importance. Monolayers of the colorectal adenocarcinoma-derived Caco-2 cell line are the current norm as intestinal absorption models in pharmacokinetic studies of orally administered drugs. Primary intestinal organoids can serve as a histologically realistic complement or alternative to the Caco-2 model, also offering the potential for personalized studies using patient-derived organoids. Interfacing the hydrogel systems introduced here with robotic and liquid-handling technologies to afford high-throughput drug screening is readily conceivable. Finally, despite proof-of-concept studies demonstrating that colon organoids expanded in vitro can effectively repair damaged colonic epithelium upon transplantation, using Matrigel-expanded organoids to treat intestinal injury and disease in humans is unimaginable. The hydrogels described herein are composed of a PEG backbone conjugated with synthetic and chemically defined peptide sequences, and are hence GMP-compatible. The three-dimensional hydrogels of the invention can be readily adapted for expanding and transplanting not only ISCs and intestinal organoids but also other types of epithelial stem cells and organoids, including those derived from the stomach, colon, rectum, pancreas, liver, lung and mammary gland.

The three-dimensional hydrogels of the invention provide a synthetic, chemically defined animal product-free environment for culturing epithelial stem cells and organoids. Namely the hydrogel matrices traditionally used to culture epithelial stem cells and organoids (e.g. Matrigel) are animal-derived (i.e. natural) products and have a poorly defined composition, whereas the three-dimensional hydrogels of the invention comprise a small number of well-defined components that can be produced synthetically in a laboratory. Hence, they are synthetic and fully defined. The advantages of such properties are important and evident to the persons skilled in the art. However, it will be appreciated that for certain applications, the addition of small amounts of naturally derived matrix components or mixtures thereof (eg, Matrigel, eg, up to 10% Matrigel), is not excluded from the invention.

In a further aspect, the invention provides a kit of parts for making discrete volumes of the three-dimensional hydrogels of the invention, comprising the following components a)

one or more hydrophilic precursor polymers; b) fibronectin, a fibronectin analogue or a fibronectin-derived fragment; c) a crosslinking agent for the precursor polymers a); and d) laminin-111, laminin-111 analogue or laminin-111 fragment In an embodiment of the kit of parts of the invention, the hydrophilic polymers comprise multiarm poly(ethylene glycol) molecules, and the fibronectin-derived fragment is RGDSPG peptide.

In a further embodiment of the kit of parts of the invention, the multiarm poly(ethylene glycol) molecules are crosslinkable by an enzyme preferably included as component c); preferably, one of the at least two hydrogel precursor molecules is functionalized by a glutamine-bearing peptide substrate and the other one by a lysine-bearing peptide substrate for a crosslinking enzyme, and the transglutaminase factor Xllla is included as component c).

In an embodiment, the components of kit of parts of the invention are provided pre-supplied in a container, preferably in wells of a multi-well plate or in a tube, in substantially unreacted form, preferably in dried form. Indeed, the components of the three-dimensional hydrogels of the invention can be pre-formulized in a dry form (lyophilized) in plates or other reservoirs. The kit can further comprise an instruction sheet including instructions for how to perform the method of the present invention.

Methods for Growing Epithelial Cell Organoids

In another aspect, the invention relates to a method for obtaining an epithelial cell organoid, comprising culturing cells in a biofunctional 3D hydrogel, wherein:
  a) the cells comprise isolated tissue or organoid fragments, and wherein the cells are cultured in conditions suitable for organoid formation; or
  b) the cells comprise culturing single or clusters of stem cells, and wherein the cells are first cultured in conditions suitable for cell expansion and subsequently cultured in conditions suitable for organoid formation,
wherein the hydrogel has a shear modulus between 0.05-3 kPa.

Growing cells within a hydrogel requires encapsulation of the cells within the gel. The cells may be seeded at a cell density of 500-1000 cells $\mu l^{-1}$, preferably 500 cells $\mu l^{-1}$.

In one embodiment of the method, the shear modulus of the hydrogel decreases over time (Example 9), preferably wherein the shear modulus of the hydrogel at the start of the method is 0.5 to 2.5 kPa, preferably 1 to 2 kPa, and most preferably 1.3 kPa or 2 kPa, and the shear modulus of the hydrogel at the end of the method is 50 to 500 Pa, preferably 100 to 300 Pa, more preferably 80-150 Pa and most preferably 120 Pa. The start of the method refers to when the stem cells or tissue fragments are first encapsulated within the hydrogel. The end of the method is when an epithelial organoid has been formed.

The dynamic character of the hydrogel used in this embodiment of the invention may be caused by hydrolysis of ester bonds in the hydrogel, preferably wherein the ester bonds are derived from multiarm poly(ethylene glycol) (PEG) molecules, more preferably wherein the multiarm PEG molecules comprise an average of 3 to 12 arms, most preferably wherein the arms terminate with an acrylate group. These PEG molecules preferably comprise 70-80% of the dynamic hydrogel network, preferably wherein the remaining percentage of the hydrogel network is hydrolytically non-degradable.

In an alternative embodiment of the invention the decrease in the shear modulus of the hydrogel is achieved through a biocompatible active mechanism, preferably comprising exposure to: light, a biomolecule, a small molecule, changes temperature or other physical parameters, more preferably wherein the active mechanism is selective for only one component of the hydrogel. The active mechanism may comprise cleavage of specific target sites in the hydrogel by a proteolytic enzyme. An example of such an enzyme is the Tobacco Etch Virus (TEV) endopeptidase, used extensively as a biochemical tool (e.g. protein engineering) or another non-mammalian protease.

The hydrogel used in any method of the present invention preferably comprises laminin-111 or a functional variant thereof (Example 10), preferably wherein the laminin-111 or a functional variant thereof is at a concentration of at least 5 µg/ml.

It will be appreciated that hydrogels for use in the methods of the present invention may be rendered biofunctional by incorporation of one or more biofunctional molecules that constitute the intestinal extracellular matrix, including but not limited to, Vitronectin, RGD containing peptides, including Fibrillin and Fibrinogen, Plasminogen, Plasmin, Aggrecan, Brevican, Tenascin, Collagen, Elastin, Hyaluronic acid proteoglycan, Keratan sulphate proteoglycan, Heparan sulphate proteoglycan, Chondroitin sulphate proteoglycan, Syndecan-I (proteoglycan), and IGF Binding Protein, or peptides containing the adhesion sequences within these molecules.

Another aspect of the invention relates to a method for quantifying epithelial stem cell organoid formation, the method comprising:
  a) obtaining an organoid using a method of the invention, and
  b) monitoring, by quantitative high-content imaging approaches, the self-organization of the cells into organoids.

Methods for Growing Epithelial Cells

In another aspect, the present invention relates to a method for growing adult stem epithelial cells, comprising culturing adult stem epithelial cells in a biofunctional hydrogel in conditions suitable for cell expansion, wherein the hydrogel comprises laminin-111 or a fragment thereof, and wherein the hydrogel has a shear modulus of 0.2 to 2 kPa.

In one embodiment of the invention, the hydrogel has a shear modulus of 0.2, 0.3, 0.7, 1.3 or 1.7 kPa (Example 7). In a further embodiment the stem epithelial cells are derived from a multicellular culture or isolated tissue fragment.

The hydrogels used in any method of the present invention preferably comprises a hydrophilic polymer crosslinked with and a functional molecule, and preferably a functional molecule comprises an oligopeptide, a small molecule, a protein, an oligo- or polysaccharides, or an oligo- or polynucleotides. The functional molecule may be an RGD-containing ligand such as fibronectin or a functional variant thereof, preferably wherein the functional variant of fibronectin is a linear, branched or cyclic peptide, more preferably wherein the functional variant thereof is selected from the group comprising: FF III$_1$-C fragment, FNIII9-10 fragment, and FNIII12-14 fragment. In an alternative embodiment the RGD containing ligand may be selected from the group comprising: RGD, RGDS (SEQ ID NO: 11), RGDSP (SEQ ID NO: 2,) RGDSPK (SEQ ID NO: 3), RGDTP (SEQ ID NO: 4) and RGDSPASSKP (SEQ ID NO: 5).

The hydrogels used in any method of the present invention preferably comprises a polymer selected from the group comprising: polyethylene glycol, polyethylene oxide, polyoxazoline, polyaliphatic polyurethanes, polyether polyurethanes, polyester polyurethanes, polyethylene copolymers, polyamides, polyvinyl alcohols, polypropylene oxide, polypropylene glycol, polytetramethylene oxide, polyvinyl pyrrolidone, polyacrylamide, polyhydroxy ethyl acrylate, polyhydroxyethyl methacrylate, or mixtures or co-polymers thereof.

The methods of the present invention may be used to grow cells comprising intestinal, colonic, gastric, hepatic, pancreatic, rectal, mammary, kidney, corneal, epidermal, hair follicle, prostate, eye or lung epithelial cells.

The methods of the present invention may be used to grow tumor-derived cells, for example cells derived from intestinal, colonic, gastric, hepatic, pancreatic, rectal, mammary, kidney, corneal, epidermal, hair follicle, prostate or lung tumors.

The hydrogels used in the methods of the invention are preferably insensitive to degradation by cell-secreted proteases such as matrix metalloproteases (MMP). The hydrogels used in the methods of the invention are preferably biocompatible.

The method for of the invention has been optimized to produce hydrogels for growing epithelial organoids. However, it will be appreciated that method of the present invention may be optimized for production of hydrogels for use in the growth of other types of stem cells and organoids.

Hydrogels

The hydrogel of the invention comprises a polymer that is preferably less than 5% w/v, more preferably less than 3% w/v and most preferably less than 2% w/v. The hydrogel also exhibits a swelling ratio (defined here as the ratio of gel volume after swelling to the volume of the gel right after crosslinking) in deionized water of less that is preferably less than 200%, preferably of less than 150%, when exposed to a fluid.

The functional molecule in the hydrogel of the invention is preferably at a concentration of 0.1-4.5 mM, most preferably 1 mM. The functional molecule may be an RGD-containing ligand, which may be is fibronectin or a functional variant thereof, preferably wherein the functional variant of fibronectin is a branched or cyclic peptide. The functional variant thereof may be selected from the group comprising: III1-C fragment, FNIII9-10 fragment, and FNIII12-14 fragment. Alternatively, the RGD containing ligand may be selected from the group comprising: RGD, RGDS (SEQ ID NO: 11), RGDSP (SEQ ID NO: 2), RGDSPK (SEQ ID NO: 3), RGDTP (SEQ ID NO: 4), RGDSPASSKP (SEQ ID NO: 5).

The hydrogel may have a shear modulus of 1.3 kPa. Alternatively, the shear modulus of the hydrogel may be 0.2-0.7 kPa, preferably 0.2 kPa, preferably wherein the functional molecule of the hydrogel comprises laminin-111 or a functional variant thereof, preferably wherein the laminin-111 is at a concentration of at least 5 µg/ml. The hydrogel also preferably comprises an RGD-containing ligand.

The polymer of the hydrogel may be PEG that is crosslinked via a covalent or a non-covalent crosslinking reaction. The covalent crosslinking reaction may be an enzymatic reaction, preferably a transglutaminase-mediated crosslinking reaction, most preferably a transglutaminase Factor XIII-mediated crosslinking reaction. The covalent crosslinking reaction may also be a mild, chemoselective reaction, preferably being a member of the family of bioclick' reactions, most preferably a Michael-type addition reaction between nucleophiles and ethylenically unsaturated bonds such as maleimides or vinyl sulfones.

Alternatively, the polymer may comprise functional groups that upon crosslinking render the hydrogel network unstable in aqueous solution, preferably by undergoing spontaneous hydrolysis. The unstable hydrogel component may derive from PEG-acrylate containing a hydrolytically degradable ester bond. The hydrogel may additionally have been crosslinked from a polymer that is stable in aqueous solution, such as PEG-vinyl sulfone, preferably wherein the unstable polymer when crosslinked comprises 70-80% of the hydrogel polymer network.

The hydrogel may be dynamic, such that the shear modulus of the hydrogel before incubation in an aqueous solution is 0.5 to 2.5 kPa, preferably 1 to 2 kPa, and most preferably 1.3 kPa, and the shear modulus of the hydrogel after incubation in an aqueous solution for 4 days is 50 to 500 Pa, preferably 100 to 300 Pa, more preferably 80-150 Pa and most preferably 120 Pa.

EXAMPLES

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing descriptions will be more fully understood with reference to the following Examples. Such Examples, are, however, exemplary of methods of practising the present invention and are not intended to limit the scope of the invention.

Example 1: Bioactive Hydrogels Can Support Growth of Epithelial Cells

Matrigel is currently used to grow epithelial organoids. To address the question of whether Matrigel serves as merely a passive 3D scaffold, providing physical support, or actively influences organoid formation by presenting essential cues, freshly-isolated intestinal crypts were embedded into enzymatically crosslinked PEG hydrogels, which are soft and hydrated and thus mimic the basic physical properties of Matrigel without providing any biochemical signals. Crypts cultured in Matrigel reorganized within 24 hours to form lumen-containing epithelial colonies, whereas those embedded in PEG failed to reorganize and underwent cell death within the same period (FIG. 1B and FIG. 1C), suggesting that not only the physical support, but also active biochemical signals provided by the matrix are required for crypt viability and morphogenesis.

Figure 2:
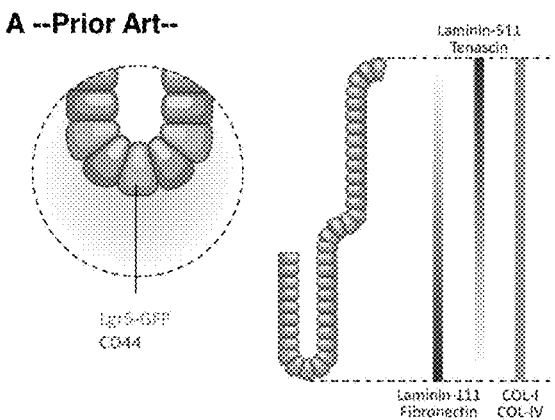
FIG. 2.
Figure 2:
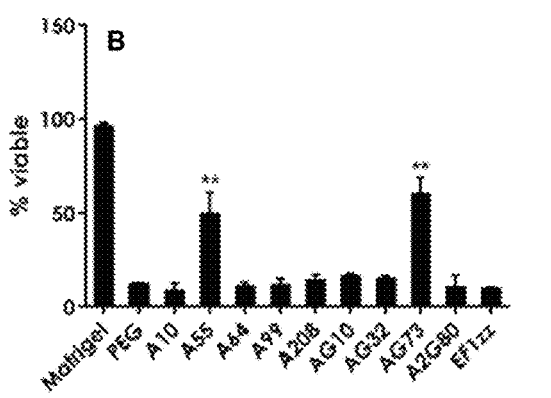
Figure 2:
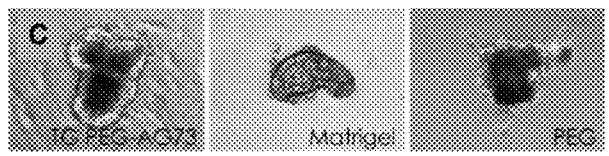
Figure 2:
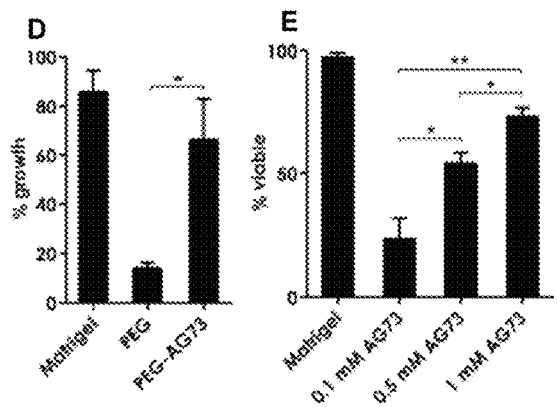

The intestinal epithelium in vivo is in direct contact with a basement membrane, which is composed of a number of proteins expressed in distinct spatiotemporal patterns (FIG. 2A). Notably, the expression of specific protein components, including fibronectin and the α1 laminin subunit, is confined to the regions surrounding the ISC-housing crypt bases. Likewise, CD44 (the cell surface receptor that recognizes and binds to hyaluronic acid) is expressed specifically by ISCs. Given their physical proximity, it was reasoned that these proteins and sugars may constitute the ISC niche, and that incorporating them into the PEG hydrogels may help increase crypt survival and morphogenesis. Providing adhesion cues by incorporating an animal-derived full length fibronectin introduces the set of limitations that come with Matrigel-based culture, whereas including recombinant versions of the protein is cost-prohibitive, especially for the purpose of large-scale cell and tissue production. Hence, it was sought to mimic fibronectin- and laminin-based adhesion by covalently attaching short peptide sequences. Whereas the RGD sequence known to mimic cell binding to fibronectin is well known, recapitulating laminin-based adhesion is not straightforward, as cell interaction with the full length protein has not been successfully mimicked by a short amino acid sequence.

To identify a short sequence that supports intestinal cell survival, a library of soft (G'=200 Pa) hydrogels was created, in which specific binding sequences from the laminin α1 subunit (Table 1) were tethered to the PEG backbone. Screening the library for intestinal tissue survival and morphogenesis revealed that two laminin-derived peptides, AG73 and A55, significantly enhanced organoid viability and supported further growth (FIG. 2B). Presenting these two sequences alongside in the same gel did not appear to have an additive effect, likely owing to redundant syndecan-based adhesion signalling. Hence, the sequence with a stronger individual effect, i.e. AG73, and the corresponding PEG gels (referred to as TG PEG-AG73) were selected for further characterization. Varying the amount of AG73 peptide tethered to the PEG gel backbone revealed a dose-dependent effect on intestinal organoid viability and growth (FIG. 2C-E).

Despite the improved rate of survival and morphogenesis in TG PEG-AG73 matrices compared with plain PEG or PEG RGD, the process was significantly less efficient compared with Matrigel, and morphological differences were apparent (FIG. 2C). Keeping in mind that the effect of AG73 was concentration-dependent (FIG. 2E), these differences could be attributed to a potentially sub-optimal AG73 ligand density within the synthetic system. There is an upper limit to the concentration of tethered factors that can be incorporated into the PEG system used in this Example: exceeding this limit disrupts the structural integrity of the gels. To side-step this limitation and enhance the biofunctionality of the synthetic matrix by increasing the concentration of AG73 ligands, chemically crosslinked functionalised PEG gels were considered.

Example 2: Biomolecule Incorporation into Functionalised Hydrogels

Modifying the structure of the PEG macromolecules in a first crosslinking reaction facilitated production in the second crosslinking reaction of low solid content hydrogels that could be rendered biofunctional without affecting their mechanical properties.

To incorporate the AG73 ligand at a high density, a functional molecule was designed wherein the AG73 sequence was flanked by two short cysteine-containing sequences. VS-conjugated 4-arm liquid PEG macromolecules were covalently linked into solid hydrogels through Michael-type addition between VS groups and the thiols of a short crosslinker containing two cysteine residues. The resulting 3, 3.5 and 4% PEG gels (hereafter referred to as MT-PEG-AG73) presented the AG73 ligand at concentrations of 3.1, 3.7 and 4.2 mM, respectively, thus far surpassing the highest concentration achieved in the enzymatically crosslinked matrices. These matrices were considerably softer than TG PEG-AG73 gels (FIG. 3M), thus meeting another microenvironmental requirement for intestinal organoid formation.

Example 3: Functionalised Hydrogels Support Organoid Maintenance

The functionalised hydrogels were able to support epithelial organoid maintenance within intestinal tissue fragments. Embedding intestinal tissue fragments into MT PEG-AG73 revealed that the percentage of tissues that remained viable and continued to undergo morphogenesis approached that observed in Matrigel (FIG. 3B and FIG. 3C).

Figure 3:
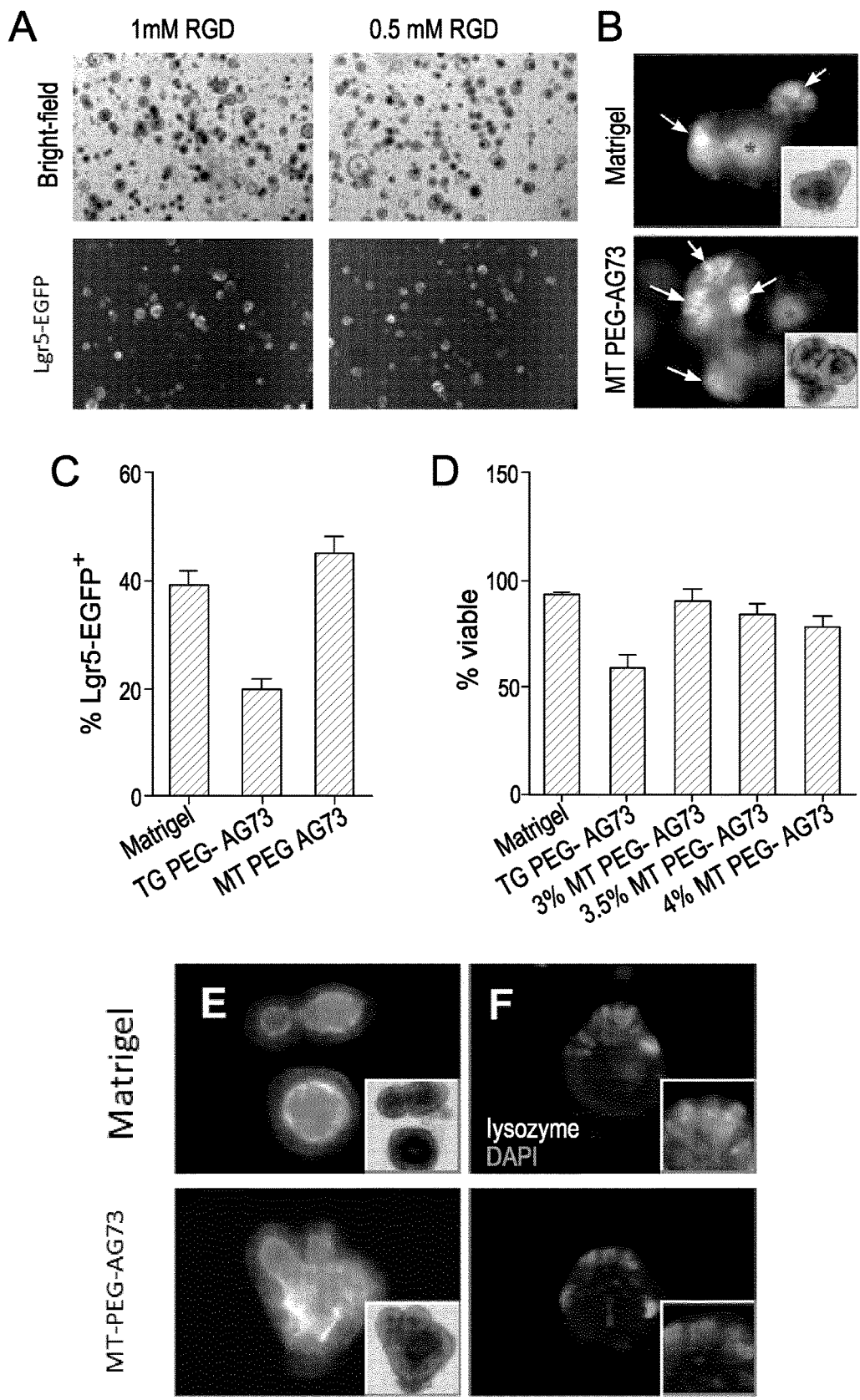
FIG. 3.
Figure 3:
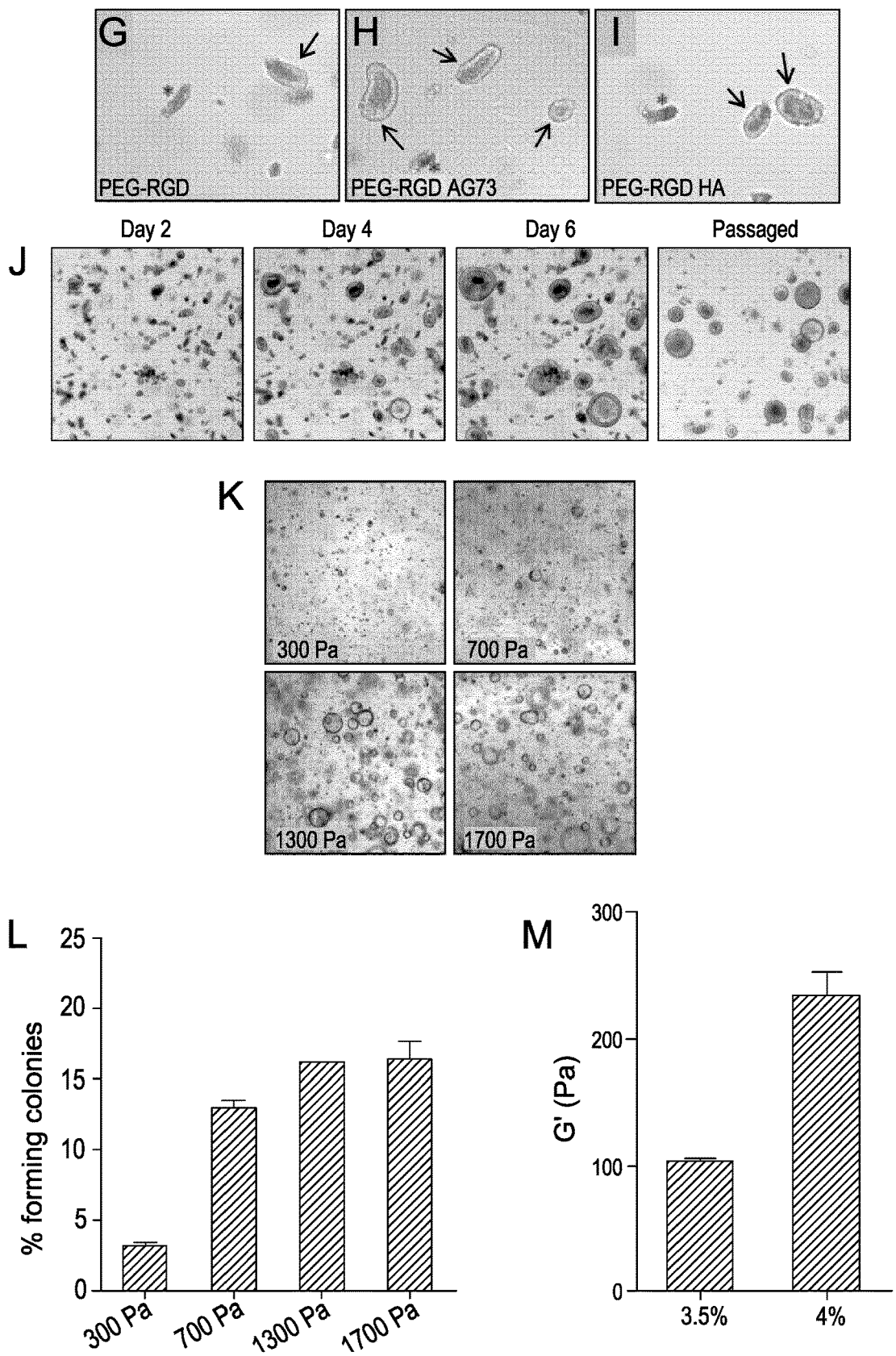

ISCs encapsulated into functionalised bioactive hydrogels (4- and 8-arm MT PEG-RGD) containing either 0.5 of 1 mM RGD at different stiffness were also able to support ISC proliferation (FIG. 3A).

To verify the maintenance of ISCs within the organoids grown in MT-PEG-AG73 and MT PEG-RGD, tissues extracted from the Lgr5-EGFP reporter mouse were embedded into the synthetic hydrogels and EGFP (Enhanced green fluorescent protein) expression was monitored. Lgr5-EGFP was expressed in the expected pattern, localized to the crypt-like buds of the organoids (FIG. 3B). The fraction of organoids expressing the marker was significantly higher in MT-PEG-AG73 than those cultured in TG-PEG-AG73, and at least as high as in organoids cultured in Matrigel (FIG. 3C). Notably, a slight, but significant drop in tissue viability was observed as the PEG percentage and, consequently, matrix stiffness increased (FIG. 3D). Staining with phalloidin revealed that F-actin was enriched on the luminal side of the epithelium, confirming the establishment of apicobasal polarity within the tissue (FIG. 3E). Stem cell differentiation into functional cell types was confirmed by immunofluorescence analysis. Staining for lysozyme verified the presence of Paneth cells in the expected locations, interspersed with Lgr5+ stem cells in the characteristic checkerboard pattern (FIG. 3F). The organoids therefore retained the normal characteristics of epithelial cell organoids during culture in the hydrogels.

Example 4: Hydrogels Support Epithelial Cell Growth

Freshly isolated crypts cultured in non-functionalised PEG-RGD hydrogels survive and proceed to form colonies (FIG. 3G-I). Upon dissociation and re-embedding, these cells give rise to secondary colonies (FIG. 3J), indicating that PEG-RGD can be used for the sustained culture of freshly derived ISCs. AG73 and hyaluronic acid lead to a synergistic increase in crypt viability when presented alongside RGD (FIG. 3H and FIG. 3I). Therefore, ISC culture can be initiated in PEG-RGD, thus circumventing a step involving Matrigel.

The expansion of Lgr5+ in these cultures was increased by supplementing the standard intestinal organoid growth medium [69] with CHIR99021, a GSKβ3 inhibitor and hence an activator of the Wnt pathway, and valproic acid, a histone deacetylase (HDAC) inhibitor and agonist of the Notch pathway, as described previously [70]. To address concerns that sustained ISC culture in the presence of a HDAC inhibitor may result in the accumulation of deleterious epigenetic changes, it was found that ISCs could alternatively be successfully cultured in PEG-RGD in the presence of recombinant Wnt3a (FIG. 3K and FIG. 3L). Notably, the stiffness-dependent colony formation profiles and overall colony formation efficiencies were consistent with those observed in CHIR99021 and valproic acid-containing culture (FIG. 3K and FIG. 3L).

Figure 4:
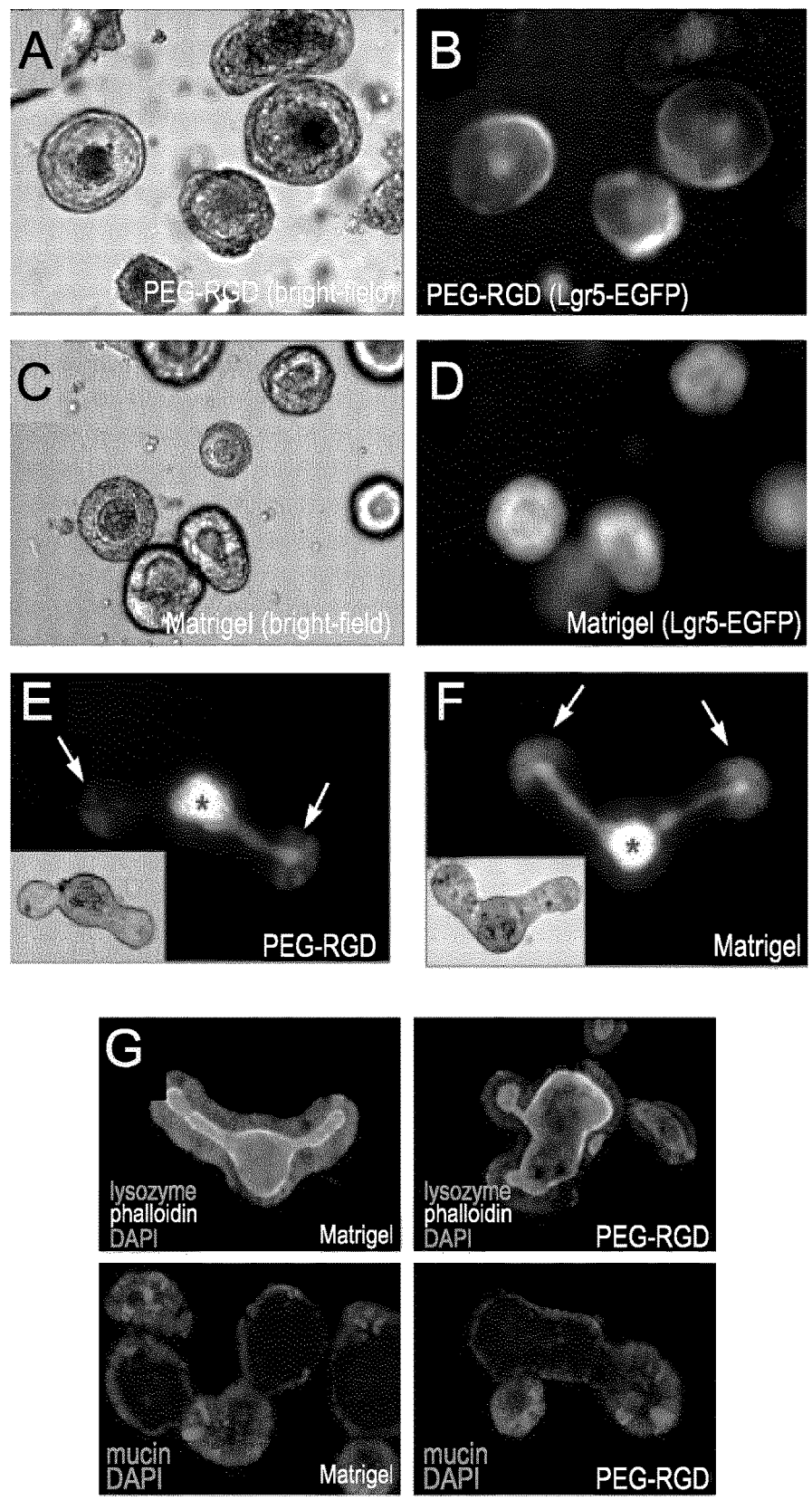
FIG. 4: Fig A-D show ISC colony morphology and Lgr5-EGFP expression in Matrigel and PEG-RGD.
Figure 4:
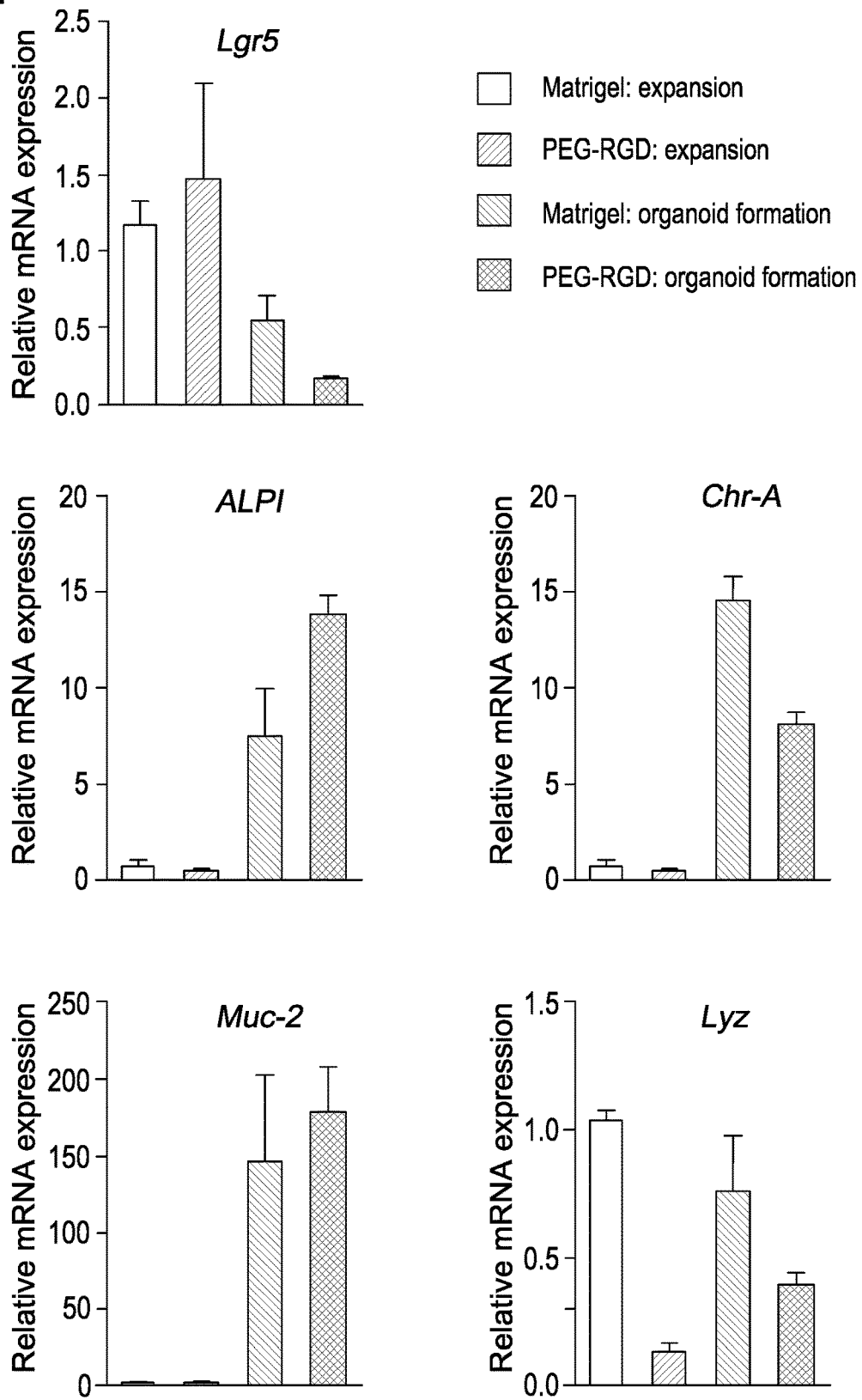
Figure 4:
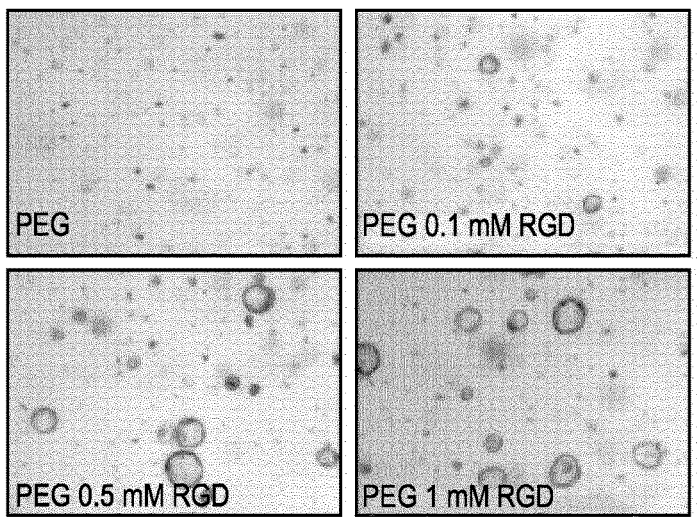
Figure 4:
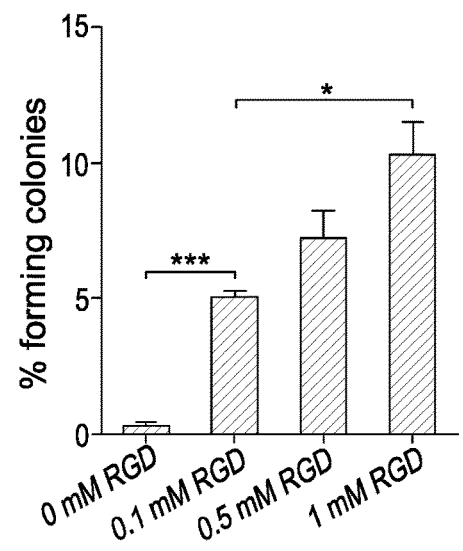
Figure 4:
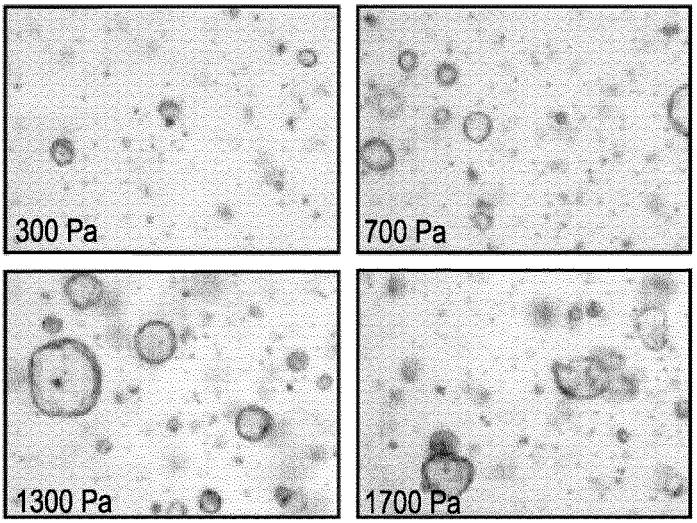
Figure 4:
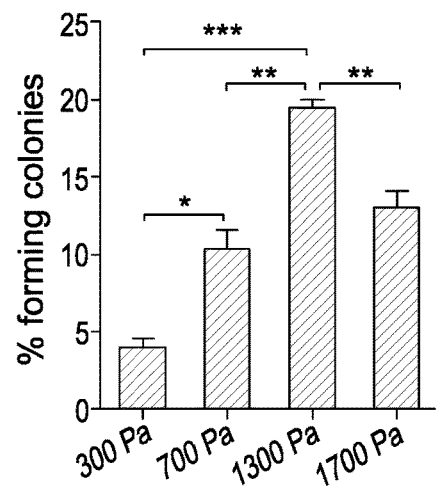

Expanding the ISC colonies grown on PEG-RGD hydrogels in culture conditions suitable for cell expansion (self-renewal conditions), followed by dissociation and re-embedding of the resulting single cells into PEG-RGD hydrogels lead to robust and clonal colony formation (FIG. 4A) comparable with Matrigel (FIG. 4B). Notably, the ISC marker Lgr5 was expressed by colonies cultured within TG-PEG-RGD hydrogels at levels comparable with those of cells cultured in Matrigel (FIG. 4C and FIG. 4D), indicating that bona fide ISCs can be successfully cultured and expanded within TG-PEG-RGD hydrogels.

To confirm that the ISCs retained their multi-lineage differentiation potential and capacity to form organoids, the expanded stem cells were transplanted into Matrigel, where they were further expanded and subsequently differentiated. Within 2 days after switching to differentiation conditions, the spherical colonies, which expressed Lgr5-EGFP uniformly had transformed into organoids containing crypt-like protrusions, with Lgr5-EGFP expression confined to the end regions of the latter (FIG. 4E and FIG. 4F). Immunofluorescence analysis for lysozyme and mucin established the presence of Paneth and goblet cells, respectively (FIG. 4G), confirming that ISCs expanded within synthetic TG-PEG-RGD matrices maintained their multipotency.

ISC maintenance was also confirmed by assessing the expression of key intestinal genes by qPCR (FIG. 4H). Under ISC expansion conditions, Lgr5 was highly expressed in ISC grown on both PEG-RGD and Matrigel, confirming the maintenance of stemness within the expanded cells. As expected, Lgr5 was less abundant in organoids cultured in both PEG and Matrigel. Markers of differentiated intestinal cell types are not expressed under expansion conditions. However, lysozyme appears to be significantly expressed in Matrigel-based expansion culture, indicating that colonies expanded in Matrigel contain a population of differentiated Paneth cells. Hence, PEG-based hydrogels may be more suitable for the maintenance of a purified Lgr5+ ISC population.

Example 5: The Effect of RGD Concentration on Cell Proliferation in Hydrogels

To determine the optimal concentration of adhesion ligands, varying amounts of RGD peptide were covalently linked to non-functionalised biofunctional hydrogels (TG-PEG-RGD). Increasing the concentration of RGD lead to an increase in ISC colony formation efficiency, wherein the latter reached a plateau at a RGD concentration of approximately 500 µM (FIG. 4I and FIG. 4J).

Example 6: The Effect of Matrix Stiffness on Cell Proliferation in Hydrogels

To define the effect of matrix stiffness on ISC expansion, functionalised hydrogels (F-PEG-RGD) were generated with a range of mechanical properties, determined by their PEG polymer content. The behaviour or ISCs cultured in these hydrogels was monitored. Matrix stiffness influenced colony forming efficiency and growth in a significant, yet biphasic manner (FIG. 4K and FIG. 4L), ISC expansion was optimal within matrices of intermediate stiffness (shear modulus of 1.3 kPa). Importantly, cells embedded in soft matrices (shear modulus of 300 Pa) proliferated, but poorly, despite being presented with the optimal (1 mM) concentration of RGD, suggesting that a proper mechanical environment is critical for optimal ISC expansion. Blocking myosin-mediated contractility with blebbistatin abolished the stiffness-induced increase in colony formation efficiency, suggesting that cytoskeletal tension is required for ISC expansion within synthetic matrices.

Example 7: Effect of Biofunctional Compounds on Cell Proliferation

Figure 5:
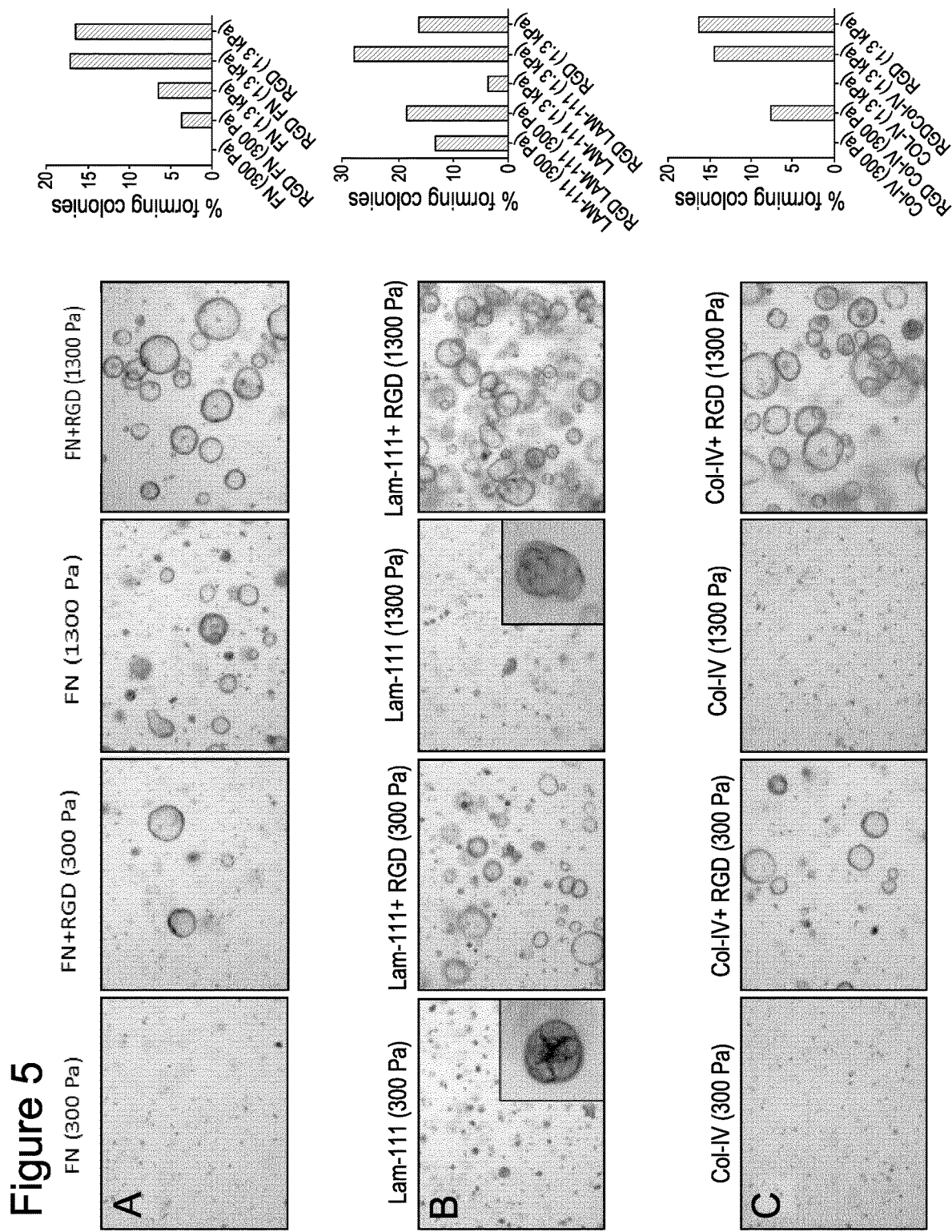
FIG. 5 shows the effect of various ECM components on ISC colony formation in PEG hydrogels. Each ECM component was incorporated in soft (300 Pa) or stiff (1300 Pa) matrices, alone or in combination with RGD. FN: fibronectin, Lam-111: laminin 111, Col-IV: collagen IV, Lam-511: laminin 511, HA: hyaluronic acid, Col-I: collagen I.

Fibronectin phenocopied the effect of RGD on ISC self-renewal (FIG. 5A). Individually, it led to appreciable colony formation only in stiff matrices, and no added effect was observed when fibronectin was co-presented with RGD, suggesting an expectedly redundant effect of these two molecules.

Laminin-111 alone effectively supported colony formation in soft matrices. It also led to increased colony formation efficiency when incorporated alongside RGD, regardless of matrix stiffness (FIG. 5B).

Collagen-IV and laminin-511 had no effect of ISC colony formation, in soft or stiff gels, individually or in combination with RGD (FIG. 5C and FIG. 5D).

Perlecan alone did not alter ISC self-renewal, but starkly increased colony formation efficiency when co-presented with RGD, in stiff matrices (FIG. 5E).

Hyaluronic acid, despite having a positive effect on crypt survival in TG-PEG-RGD gels (FIG. 3I), did not appear to influence the survival and self-renewal of individual ISCs in combination with RGD (FIG. 5E).

Figure 6:
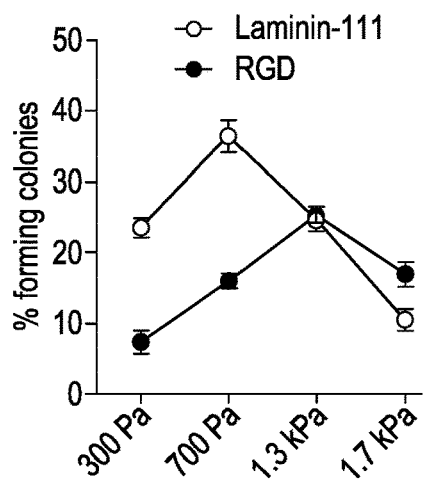
FIG. 6 shows intestinal organoid formation in soft PEG hydrogels.
Figure 6:
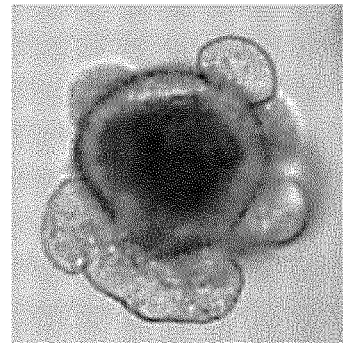
Figure 6:
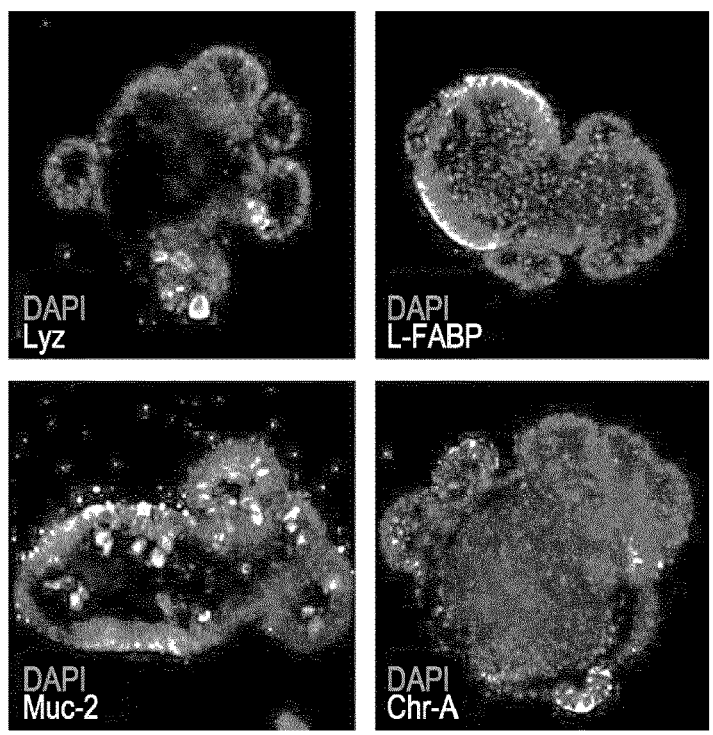
Figure 6:
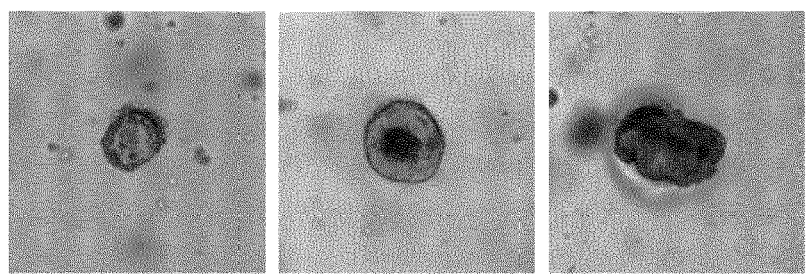

Collagen-I did not have a striking effect on ISC survival or colony formation, but profoundly influenced ISC morphology and fate/self-renewal: ISCs embedded in soft hydrogels in the presence of collagen-I and RGD failed to form the typical lumenized multicellular colonies, but instead adopted a spindle-like morphology, with actin-rich protrusions extending into the surrounding matrix (FIG. 5F). Lumenized colonies were observed in stiff gels containing collagen-I and RGD, but these colonies likewise displayed an aberrant morphology, with constituent cells extending membrane protrusions into the matrix. Notably, viable cells and colonies cultured in the presence of collagen-I were largely devoid of Lgr5-EGFP, indicating a loss of stemness.
Laminin As mentioned above, Laminin alone effectively supported colony formation in soft matrices (FIG. 5B). Indeed, within a soft, 300 Pa hydrogel, laminin-111 is significantly more efficient in inducing ISC colony formation compared with RGD (FIG. 6A). Moreover, ISC colony formation efficiency within laminin-containing gels peaks at a lower stiffness (700 Pa) compared with that in RGD-containing gels (1.3 kPa). It was therefore assessed whether the differential mechanical needs of the expansion and organoid formation stages could be reconciled by using laminin to enhance colony formation within soft (>200 Pa) matrices, which are also suitable for differentiation and organoid formation. Indeed, high (30-50%) ISC colony formation was observed in soft hydrogels containing both RGD and laminin-111. As expected, upon switching to organoid formation conditions, a small portion of the ISC colonies gave rise to intestinal organoids (FIG. 6B), which contained Paneth cells, goblet cells, enterocytes and enteroendocrine cells (FIG. 6C). Of note, single ISCs were found to also give rise to organoids when grown within soft (300 Pa) gels that contained only laminin (FIG. 6D).

Example 8: Cell Proliferation in Degradable Hydrogels

Matrix metalloproteinases (MMPs) are expressed at low levels during normal function of the intestine, and become up-regulated during intestinal disease, during which they contribute to the inflammatory response and the subsequent epithelial damage. Whereas the proteolytic response of the intestinal epithelium as a whole has been investigated, the role and behaviour of ISCs, in particular, during MMP-mediated matrix degradation is unclear.

Figure 7:
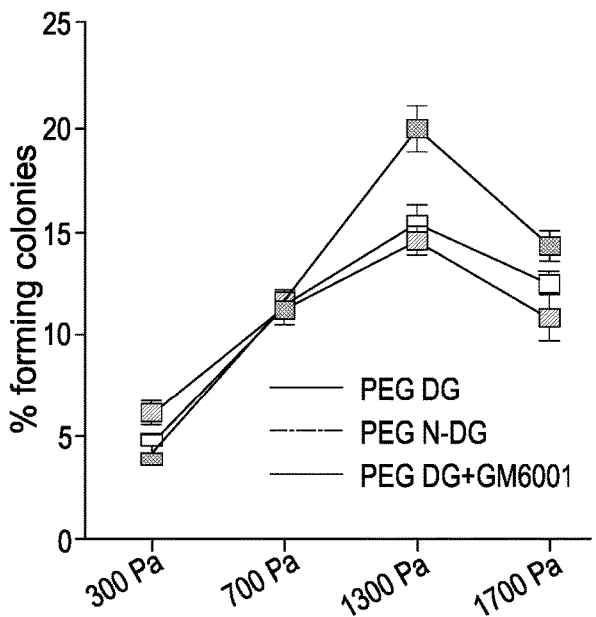
FIG. 7 shows effect of matrix proteolysis on ISC proliferation, morphology and fate.
Figure 7:
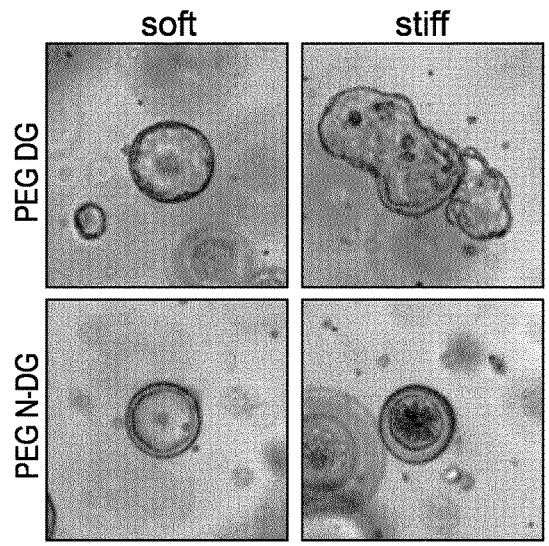
Figure 7:
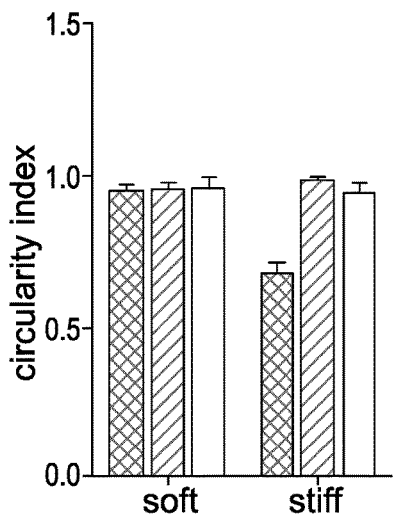
Figure 7:
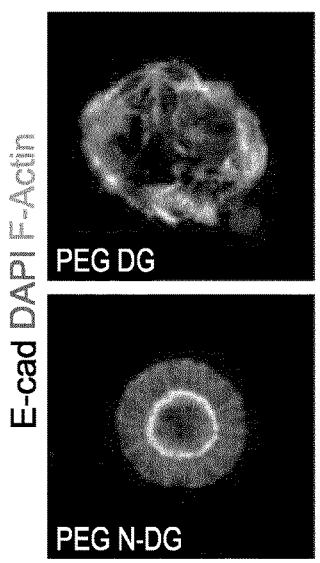
Figure 7:
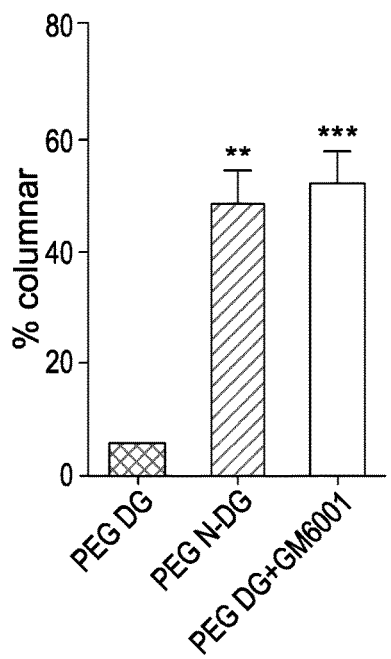
Figure 7:
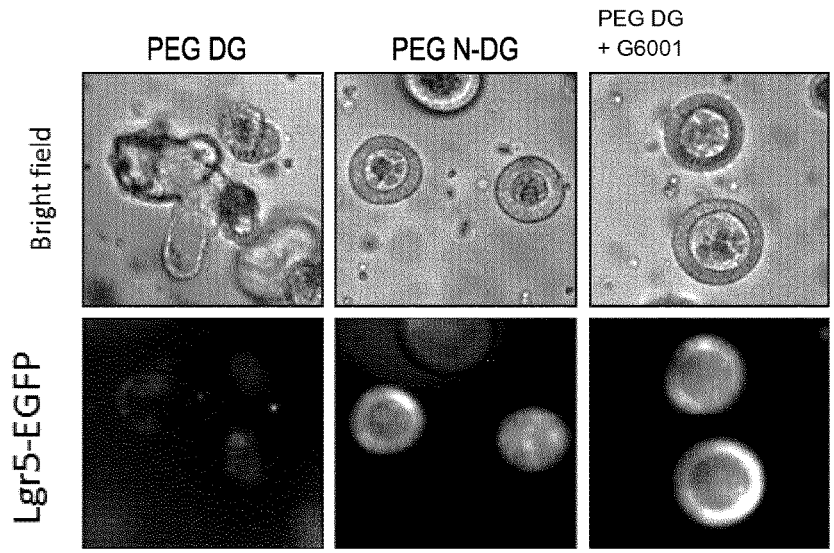
Figure 7:
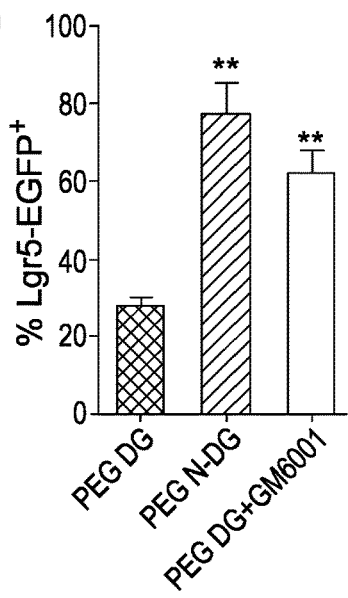
Figure 7:
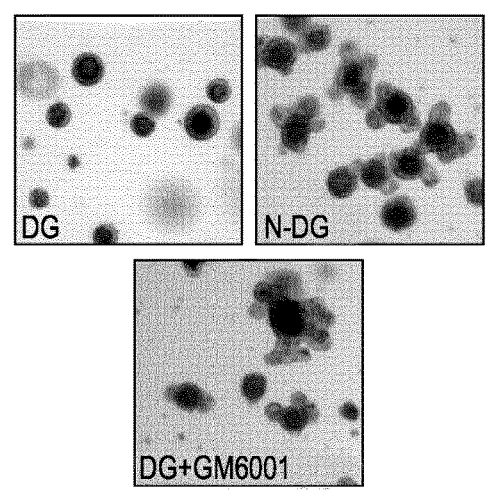
Figure 7:
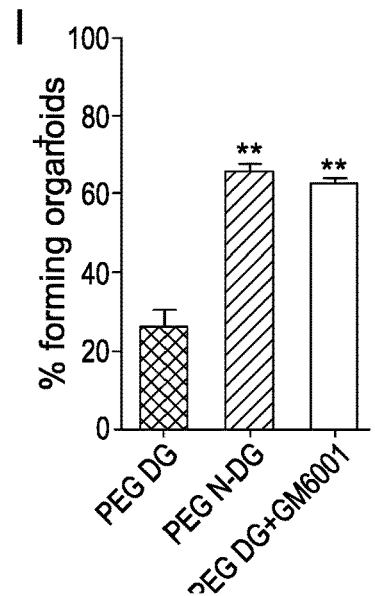

To investigate the effect of matrix proteolysis on cell growth in hydrogels, the latter was embedded in functionalised bioactive hydrogels harbouring a collagen I-derived sequence that can be recognized and cleaved by cell-secreted proteases. Cell behaviour was likewise monitored in hydrogels presenting a modified version of the sequence, which renders them insensitive to proteases. Cells cultured in both degradable and non-degradable hydrogels showed a similar bi-phasic proliferation response to matrix stiffness (FIG. 7A). However, at high mechanical stiffness colony formation efficiency was significantly higher in degradable matrices, compared with their non-degradable counterparts. Blocking MMP activity within non-degradable gels with the broad-spectrum protease inhibitor GM6001 did not alter colony formation efficiency at low matrix stiffness, but reduced it to levels observed in non-degradable gels at high matrix stiffness (FIG. 7A). These results suggest that matrix degradability confers a proliferative advantage at high mechanical stiffness. Aside from colony formation capacity, matrix degradability influences ISC colony shape in a stiffness-dependent manner. Whereas ISC colonies cultured in soft matrices were round and circular irrespective of matrix degradability, those cultured in stiff degradable matrices displayed irregular and eccentric shapes (FIG. 7B and FIG. 7C). Colony morphology was likewise profoundly affected by matrix degradability: non-degradable matrices gave rise to polarized and well-organized columnar epithelial colonies, whereas colonies formed in degradable matrices were incompletely polarized and featured spread cells (FIG. 7D and FIG. 7E).

It was additionally discovered that the change in shape and morphology observed in degradable matrices was associated with a significantly attenuated Lgr5 expression compared with colonies grown in non-degradable matrices (FIG. 7F and FIG. 7G). Unsurprisingly, the loss of Lgr5 translated to a diminished multi-lineage commitment and organoid formation capacity (FIG. 7H and FIG. 7I). Notably, pharmacologic inhibition of protease activity within degradable matrices phenocopied the effects of non-degradable matrices on colony shape, morphology, Lgr5 expression and organoid formation potency (FIG. 7B-I).

Figure 8:
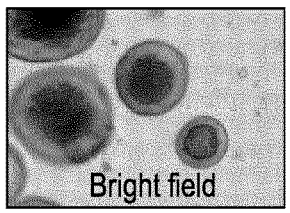
FIG. 8 shows that organoid formation requires a soft matrix.
Figure 8:
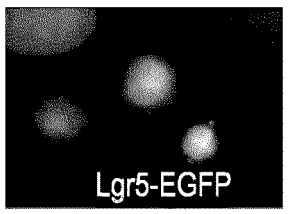
Figure 8:
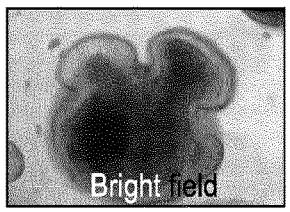
Figure 8:
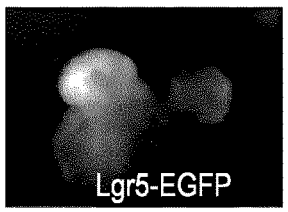
Figure 8:
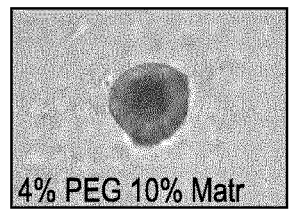
Figure 8:
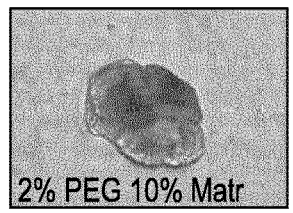
Figure 8:
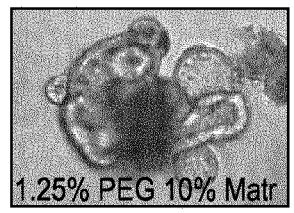
Figure 8:
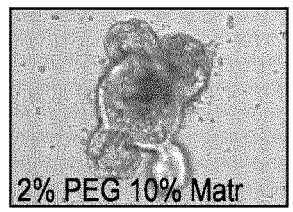
Figure 8:
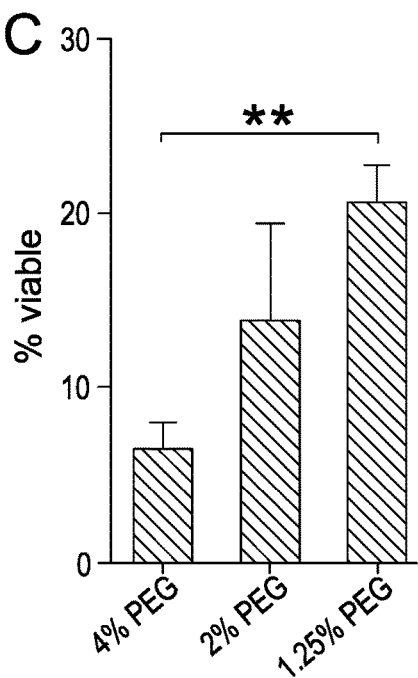
Figure 8:
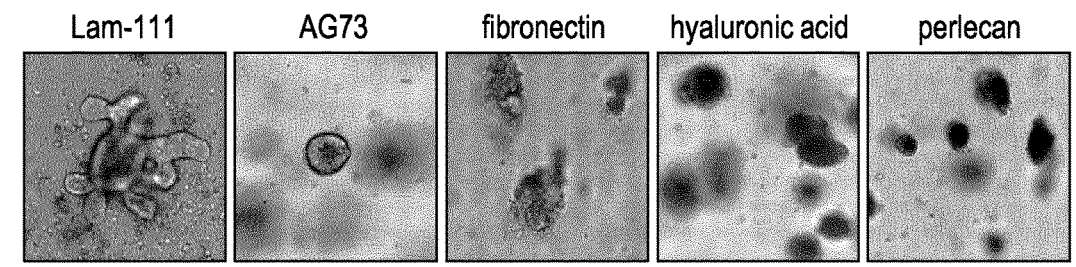
Figure 8:
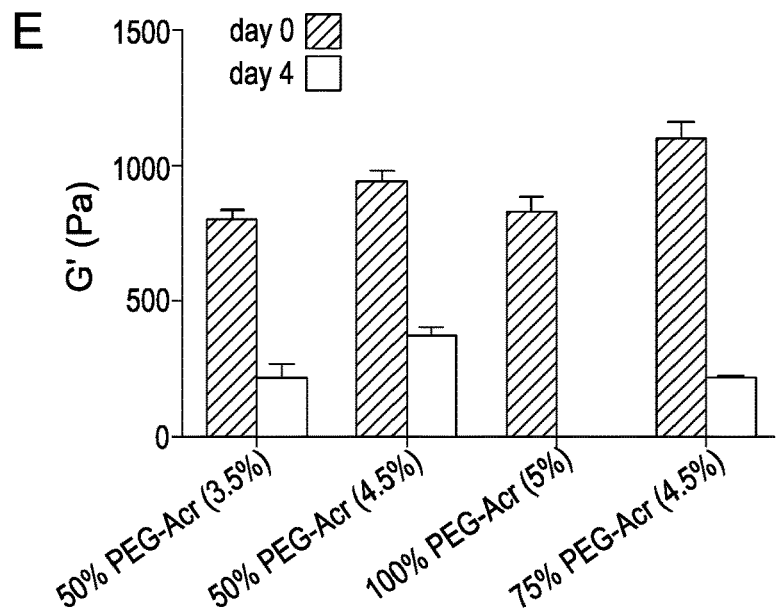
Figure 8:
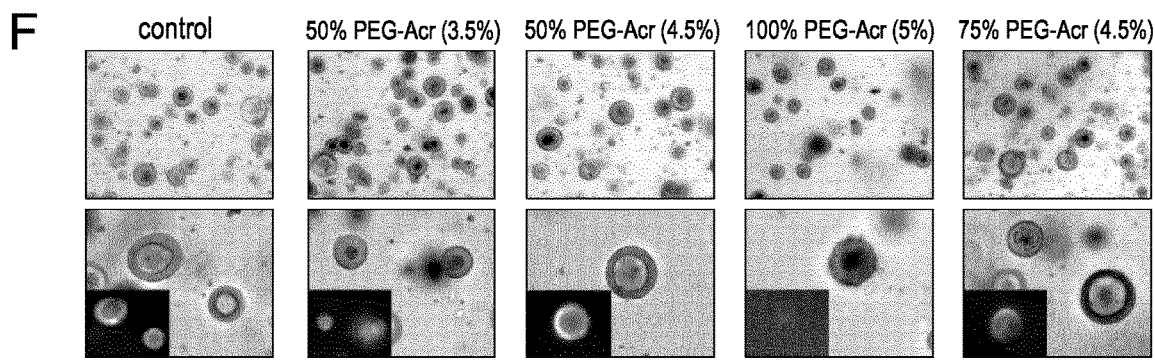
Figure 8:
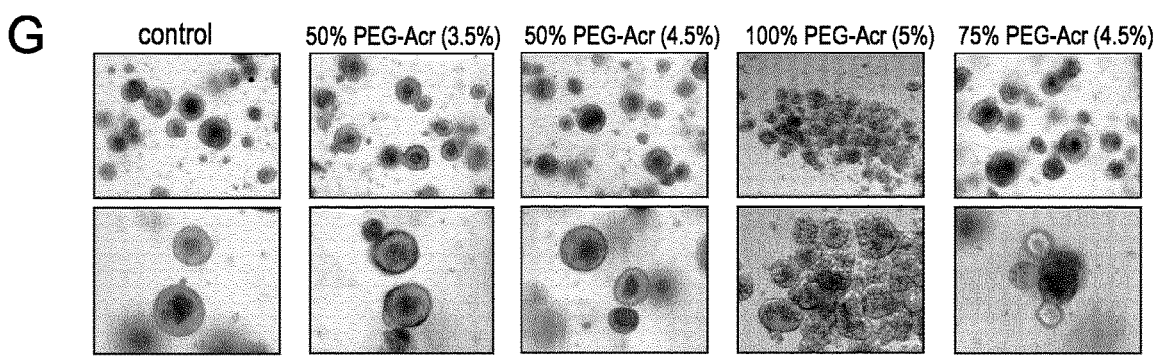
Figure 8:
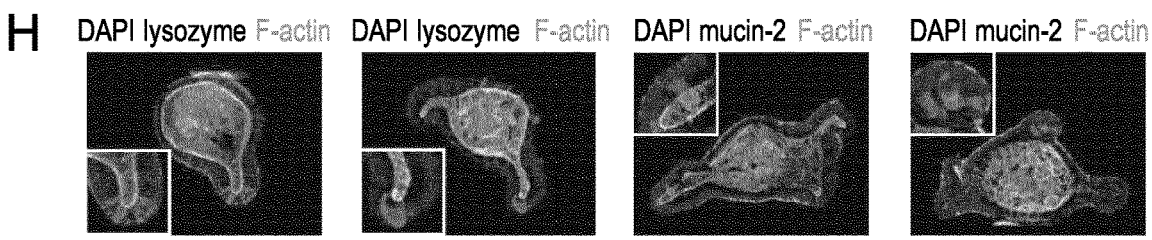

Example 9: Differentiating Epithelial Cells in Hydrogels to Obtain Epithelial Organoids To test whether functionalised hydrogels (e.g. F-PEG-RGD) can support epithelial cell differentiation and morphogenesis into intestinal organoids, cells cultured in stiffer hydrogels, that is, in conditions suitable for epithelial stem cell expansion and proliferation, were switched to differentiation conditions. The switch led to global loss of Lgr5-EGFP and colony destruction (FIG. 8A). Loss of multipotency during proliferation was ruled out as a cause for this effect, given that ISCs expanded in F-PEG-RGD are able to differentiate and give rise to organoids when transplanted into Matrigel.

It was reasoned that the stiffer matrices optimized for cell expansion may be lacking key microenvironmental factors required for differentiation and morphogenesis or may simply be too stiff to promote morphogenesis. Intriguingly, the small portion of colonies expressing EGFP (Enhanced green fluorescent protein) in a localized pattern, reminiscent of that observed in Matrigel, were colonies which had "broken symmetry", i.e. displayed non-spherical, polarized shapes (FIG. 8B). It was postulated that the change in shape and the adoption of non-spherical tissue geometry with bud-like regions is essential for the maintenance of a localized Lgr5 expression, and that such changes in shape may be facilitated by a soft matrix that is readily deformed by the tissue.

To test this hypothesis, Matrigel-PEG composites were created in which a fixed (10%) concentration of Matrigel provided the chemical signalling and adhesion required for cell survival, whereas the mechanical properties of the hydrogel were varied by changing the PEG content of the material. Fragments of organoids previously expanded were embedded in Matrigel and it was observed that, under conditions of identical biochemical and adhesion cues, intestinal morphogenesis was controlled by matrix stiffness: organoid fragments cultured in stiff matrices remained spherical and grew minimally, whereas those cultured in soft matrices underwent robust morphogenesis, adopting the characteristic budding shapes normally observed in Matrigel (FIG. 8C and FIG. 8D). It was concluded that, while high matrix stiffness is required for ISC expansion, stiff matrices impair ISC differentiation and morphogenesis, which is optimal in soft environments.

The mechanical needs of the process of organoid formation seem thus dynamic and stage-dependent, making the stiffer and mechanically static matrices described suboptimal for generating intestinal organoids from single ISCs. It was reasoned that, aside from differential mechanical needs, the self-renewal and organoid formation stages may also display differential biochemical needs.

To test whether soft PEG-RGD matrices were sufficient to drive differentiation and morphogenesis of expanded ISC colonies, colonies were grown in the optimized 1 kPa PEG-RGD matrices, and subsequently transferred into soft (~200 kPa) F-PEG-RGD matrices under differentiation and organoid formation conditions. Aside from RGD, ECM proteins, peptides and sugars, including laminin-111, AG73, fibronectin, perlecan and hyaluronic acid, were supplied to the PEG gels in separate conditions. In this experiment, pronounced morphogenesis and organoid formation were observed only in PEG gels containing both RGD and laminin-111 (FIG. 8D). Notably, the laminin-derived AG73 peptide, which was above shown to be beneficial in maintaining organoid pre-formed in Matrigel, also showed some early signs of differentiation and morphogenesis.

Dynamic Hydrogels

It was then sought to meet the evolving physical needs of the process of organoid formation by designing mechanically dynamic matrices, which would initially afford the higher stiffness beneficial for ISC expansion, but would subsequently soften to permit optimal differentiation and organoid formation. To this end, dynamic functionalised PEG hydrogels were created (DF-PEG-RGD) wherein the stable PEG-vinyl sulfone (PEG-VS) polymer backbones in at least some of the PEG molecules were replaced with a PEG-acrylate (PEG-Acr) backbone. Owing to the presence of an ester bond, PEG-Acr undergoes spontaneous hydrolysis. When PEG-Acr is incorporated into a hydrogel, this leads ultimately to global and sustained gel degradation.

Varying the ratio of PEG-VS and PEG-Acr within the final gels afforded control over their structural and mechanical dynamics, including the extent of softening over time. Varying the overall PEG polymer content facilitated control of the initial gel stiffness. Hydrogels were formed with a shear modulus of ~1 kPa (the optimal value for ISC expansion) and varying extents of softening over time (FIG. 8E). Notably, the softening of the hydrogels comprising PEG-Acr only was so extensive that it precluded mechanical characterization after 4 days.

The capacity of the dynamic hydrogels to support ISC expansion, followed by subsequent differentiation and organoid formation, was then tested. ISC colony formation in all conditions was extensive and comparable to that observed in control matrices (composed of PEG-VS only) (FIG. 8F). Loss of both polarity and Lgr5-EGFP expression was noted in the gels fully composed of PEG-Acr. This behaviour can likely be attributed to the rapid and extensive degradation of these matrices.

Upon switching the colonies of expanded cell into differentiation/organoid formation conditions for two days, it was found that the softening profile of the gels significantly influenced the emergent phenotype (FIG. 8G). PEG-Acr-only gels were fully degraded by day 6; resident colonies became depolarized and sedimented to the bottom of the dish. Colonies cultured in gels containing 50% PEG-Acr and 1 kPa in initial stiffness remained round and failed to form organoids, much like the colonies grown in control (full PEG-VS) hydrogels. Decreasing the initial and the final stiffness of these hydrogels by reducing the overall polymer content gave rise to colonies that displayed deviations from the spherical morphology observed in the control condition, and showed early bud formation. Increasing the PEG-Acr content to 75% increased the drop in stiffness, which proved sufficient for allowing morphogenesis to occur: colonies cultured in these matrices extended buds and formed bona fide organoids. Immunofluorescence analysis for lysozyme and mucin-2 revealed the presence of Paneth and goblet cells, respectively, thus confirming that differentiation occurred concurrently with morphogenesis (FIG. 8H).

Example 10: Growth of Pancreatic Cells to Obtain Organoids

Figure 9:
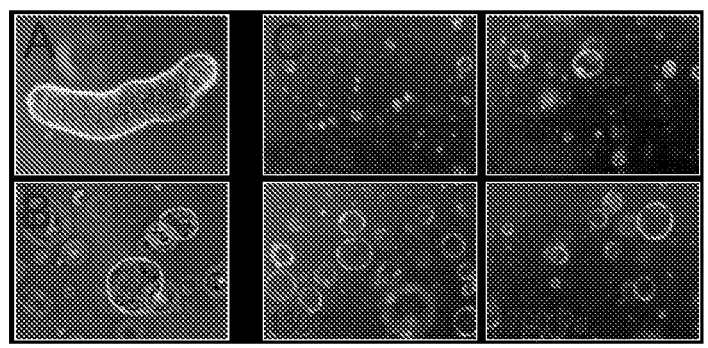
FIG. 9 shows culture and expansion of various mouse and human organoids in PEG-RGD.
Figure 9:
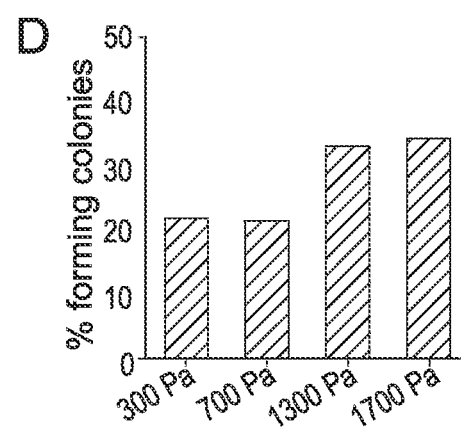

Fragments of adult mouse pancreatic ducts were embedded in F-PEG-RGD, and cultured under conditions described previously. The fragments survived, and within 48 h reorganized into lumenized epithelial structures (FIG. 9A), which were subsequently dissociated and re-embedded in F-PEG-RGD hydrogels of varying stiffness. The single pancreatic cells proceeded to form organoids with an efficiency strongly dependent upon the stiffness of the hydrogel. As in the case the ISCs, a stiffness of 1.3 kPa in shear modulus was required for optimal organoid formation (FIG. 9B and FIG. 9C).

Example 11: Growth of Mouse and Human Tumour Organoids

Figure 10:
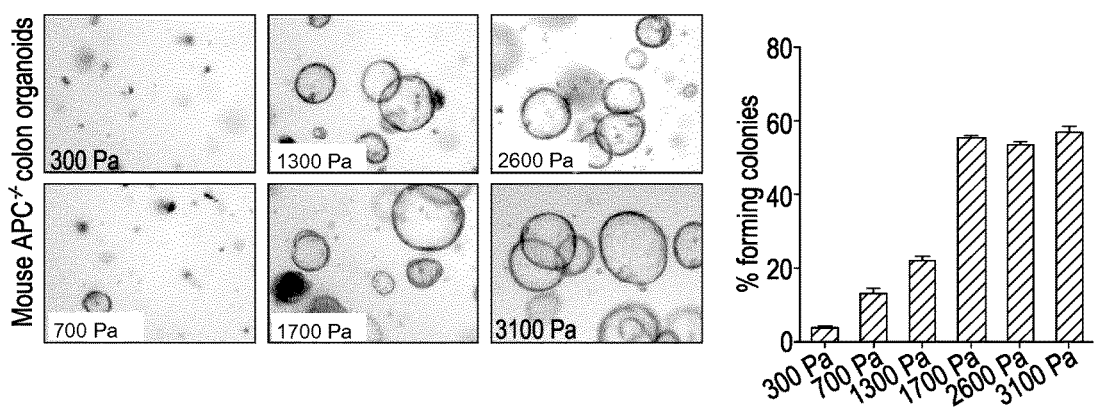
FIG. 10 shows generation of mouse and human tumour organoids in hydrogels of varying shear modulus and with or without RGD.
Figure 10:
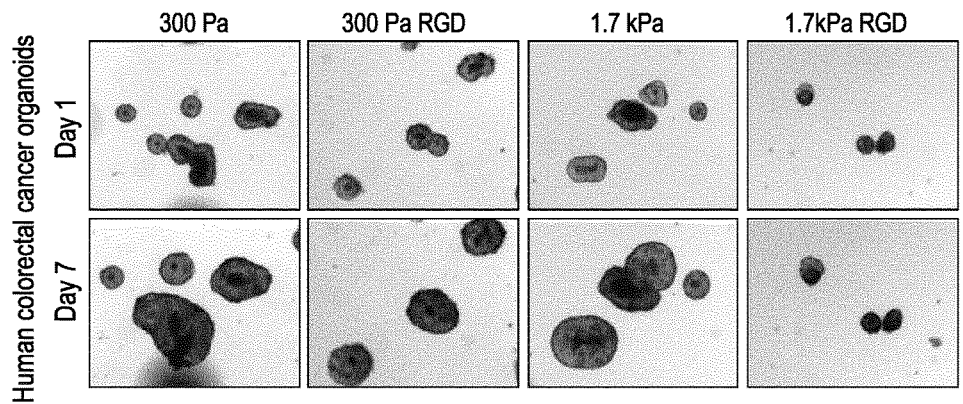

FIG. 10 shows generation of mouse and human tumour organoids in hydrogels of varying shear modulus and with or without RGD. FIG. 10A: Mouse colon adenoma organoids in PEG-RGD matrices of varying stiffness, and quantification of colon adenoma organoid formation efficiency as a function of matrix stiffness. FIG. 10B: Human patient-derived colorectal cancer organoids grow efficiently in soft and stiff matrices, with or without RGD.
Materials and methods
Mice
Intestinal crypts were extracted from 5-10 week old heterozygous Lgr5-EGFP-IRES-CreERT2 mice (Jackson Laboratory), following animal experimentation protocols prescribed by EPFL and FELASA.

Intestinal crypt isolation: Mouse intestine crypts were isolated following procedures known in the art. Briefly, the proximal part of the intestine was harvested, opened longitudinally and washed with ice-cold PBS. The luminal side of the intestine was scraped using a glass slide to remove luminal content and villous structures. After washing with ice-cold PBS again, the intestine was cut into 2-4 mm pieces with scissors. The pieces were transferred to a 50 ml Falcon tube and further washed with cold PBS (5-10 times) with gentle vortexing. Intestinal fragments were then incubated in 20 mM EDTA/PBS for 20 min on ice. EDTA was removed, 10 ml of cold PBS was added and crypts were released by manual shaking of the suspension for 5 min. The supernatant was collected and passed through a 70-.im strainer (BD Biosciences). The remaining tissue fragments were re-suspended in 10 ml cold PBS, triturated 5-10 times and the supernatant was passed through a 70-.im strainer. The previous step was repeated a second time. The three crypt-containing fractions were combined and centrifuged at 800 rpm for 5 min. The pellet was re-suspended in 10 ml cold Advanced DMEM/F12 (Invitrogen) and centrifuged at 700 rpm to remove single cells and tissue debris. The resulting pellet was enriched in crypts, which were subsequently embedded in PEG or in Matrigel (BD Biosciences; growth factor reduced, phenol red-free formulation).
PEG, Peptides and Synthesis of Hydrogels Precursors Vinylsulfone-functionalized 4- and 8-arm PEG (4-arm PEG-VS and 8-arm PEG-VS) with 20 and 40 kDa molecular weight were purchased from NOF. The peptide Ac-GCRE-GPQGIWGQ-ERCG-NH2 (mol wt 1773.1 g/mol) with matrix metalloproteinases (MMPs) sensitive sequence (in italics) was obtained from Biomatik. The adhesion peptide Ac-GRCGRGDSPG-NH2 (mol wt 1002.04 g/mol) was purchased from GL Biochem. To synthesize the modified macromers, multi-arm PEG-VS and peptides (SH/VS=10) were dissolved in triethanolamine (0.3M, pH 8.0), and reacted for 2 h at 37° C. under inert atmosphere. The reaction solution was dialyzed (Snake Skin, MWCO 10K, PIERCE) against ultrapure water (pH<7) for 4 days at 4° C., and the final product was lyophilized. The lyophilized product was dissolved in water to make 10% precursor solutions.

The FXIIIa substrate peptides Ac-0 FKGGGPQGIWGQ-ERCG-NH2 (TG-MMP-Lys) (SEQ ID NO: 3) and H-NQEQVSPL-ERCG-NH2 (TG-Gln) (SEQ ID NO: 4) and the RGD-presenting adhesion peptide H-NQEQVSPL-RGDSPG-NH2 (TG-Gln-RGD) (SEQ ID NO: 5) were purchased from GL Biochem. TG-MMP-Lys and TG-Gln were coupled to the 8-arm PEG-VS or 8-arm PEG-Acr as described in the prior art. Briefly, TG-MMP-Lys and TG-Gln were added to PEG dissolved in triethanolamine (0.3M, pH 8.0), and allowed to react for 2 h at 3TC. The reaction solution was dialyzed (Snake Skin, MWCO 10K, PIERCE) against ultrapure water for 3 days at 4° C., after which the two products (PEG-MMP-Lys and PEG-Gln) were lyophilized. The resulting solid precursors were dissolved in ultrapure water to make 13.33% w/v stock solutions.
Mechanical characterization of PEG hydrogels The shear modulus of the PEG gels was determined by performing small-strain oscillatory shear measurements on a Bohlin CVO 120 rheometer. Briefly, preformed hydrogel discs 1-1.4 mm in thickness were allowed to swell in complete cell culture medium for at least 3 h, and were subsequently sandwiched between the parallel plates of the rheometer. The mechanical response of the gels was recorded by performing frequency sweep (0.1-10 Hz) measurements in constant strain (0.05) mode, at 37° C.

Formation and Dissociation of PEG-Based Hydrogels

Appropriate volumes of 13.33% w/v PEG precursor solutions were mixed in stoichiometrically balanced ratios to generate hydrogel networks of a desired final PEG content. Hydrogel formation was triggered by the addition of thrombin-activated FXIIIa (10 U/mL; Galexis) in the presence of Tris-buffered saline (TBS; 50 mM, pH 7.6). The spare reaction volume was used for the incorporation of intestinal cells or tissues and bioactive molecules, including cell adhesion ligands. Gels were allowed to crosslink by incubating at 37° C. for 30 min. Dissociation and release of colonies grown in PEG for downstream cell processing or re-embedding was accomplished by enzymatic digestion of the gels. Gels were carefully detached from the bottom of the plate using the tip of a metal spatula and transferred to a 15-ml Falcon tube containing 1 ml of TrypLE Express (Life Technologies), supplemented with DNAse I (2000 U/ml; Roche), 0.5 mM N-acetylcysteine (Sigma) and 10 mM Y27632 (Stemgent). Following digestion (10 min, 37° C.), the cell suspension was washed with 10 ml of cold medium, passed through a 40-.m strainer (BD Biosciences) and centrifuged at 1200 rpm for 5 min.

Cell Culture

Freshly isolated crypts or single cells from dissociated colonies were added to the Matrigel or hydrogels precursor solution and cast in 20-μL droplets at the bottom of wells in 24-well plate. After polymerization (20-30 min, 37° C.), the gels were overlaid with 600 μl (500 μl for Matrigel) of ISC expansion medium (Advanced DMEM/F12 containing Glutamax, HEPES, penicillin-streptomycin, B27, N2 (Invitrogen) and 1 μM N-acetylcysteine (Sigma)), supplemented with growth factors, including EGF (50 ng/ml; R&D), Noggin (100 ng/ml; produced in-house) and R-spondin (500 ng/ml; produced in-house), and small molecules, including CHIR99021 (3 μM; Millipore) and valproic acid (1 mM; Sigma). For single cell culture, thiazovivin (2.5 μM; Stemgent) and Jagged-1 peptide (1 mM; Anaspec) was included in the medium during the first two days. Broad spectrum protease inhibitor, GM6001, was added to the medium while embedding the cells in PEG hydrogels. Every two days the growth factors were replenished and the full medium was changed.

To induce stem cell differentiation and organoid formation, the medium was removed, the gels were incubated in PBS (1 hr, 3TC) to remove residual CHIR99021 and valproic acid, and fresh medium containing EGF, Noggin and Respondin was added. In general, growth factors were replenished every two days, with full medium change taking place every four days.

Quantification of ISC Colony Formation Efficiency and Intestinal Tissue Viability To quantify the colony formation efficiency of single embedded ISCs, phase contrast z-stacks spanning the entire thickness of the cell-laden Matrigel or PEG gels were collected (Zeiss Axio Observer Z1) at 5 different locations within the gels. The Cell Counter plugin in ImageJ (NIH) was used to quantify the fraction of cells which had formed colonies at day 4 after seeding. To assess the viability of intestinal tissue fragments embedded in PEG, phase contrast images of the entire gel were collected. The fraction of viable tissues was estimated based upon the epithelial morphology: tissues that featured an epithelial monolayer surrounding a central lumen after 24 h of embedding were deemed viable.

Immunofluorescence Analysis

Intestinal organoids embedded in Matrigel or PEG were fixed with 4% paraformaldehyde (PFA) in PBS (30 min, RT). The fixation process typically led to complete degradation of the Matrigel. Hence, suspended tissues were collected and centrifuged (800 rpm, 5 min) to remove the PFA, washed with ultrapure water and pelleted. Following resuspension in water, the organoids were spread on glass slides and allowed to attach by drying. Attached organoids were rehydrated by adding PBS. Following fixation, organoids embedded in PEG or spread on glass were permeabilized with 0.2% Triton X-100 in PBS (1 h, RT) and blocked (10% goat serum in PBS containing 0.01% Triton X-100) for at least 2 h. Samples were subsequently incubated with blocking buffer-dissolved phalloidin-Alexa 546 (Invitrogen) and primary antibodies against lysozyme (1:50; Thermo Scientific) or mucin-2 (1:25; Santa Cruz) (overnight, 4° C.). After washing with PBS for 3 h (during which PBS was replaced every hour), samples were incubated with secondary antibody (Alexa 647) organoids were imaged in epifluorescence (Zeiss Axio Observer Z1) or confocal (Zeiss LSM 710) mode.

Further aspects of the invention are defined in the following numbered clauses:

1. A three-dimensional hydrogel for culturing adult epithelial stem cells comprising a cross-linked hydrophilic polymer functionalized with an RGD-containing peptide, wherein the concentration of the RGD-containing peptide is of at least 0.05% w/v, and wherein the hydrogel has a shear modulus of 0.5 to 5 kPa.
2. The three-dimensional hydrogel of clause 1, wherein the shear modulus is 0.5 to 2.5 kPa.
3. The three-dimensional hydrogel of clause 1 or 2, wherein the RGD-containing peptide is a peptide containing RGD binding motif selected from the group comprising fibronectin, fibronectin analogue or a fibronectin-derived fragment.
4. The three-dimensional hydrogel of any one of clauses 1-3, wherein the fibronectin derived fragment or fibronectin analogue is a peptide selected from the group comprising RGD, RGDS (SEQ ID NO:11), RGDSP (SEQ ID NO:2), RGDSPK (SEQ ID NO:3), RGDTP (SEQ ID NO:4), RGDSPASSKP (SEQ ID NO:5), Cyclo(RGDSP) (SEQ ID NO:2), Cyclo(RGDFK) (SEQ ID NO:6), Cyclo(RGDYK) (SEQ ID NO:7), Cyclo(RGDFC) (SEQ ID NO:8), or a fragment selected from the group comprising III1-C fragment, FNIII9-10 fragment, and FNIII12-14 fragment.
5. The three-dimensional hydrogel of any one of clauses 1-4, wherein the hydrophilic polymer is selected from the group comprising poly(ethylene glycol), polyoxazoline, polyaliphatic polyurethanes, polyether polyurethanes, polyester polyurethanes, polyethylene copolymers, polyamides, polyvinyl alcohols, poly(ethylene oxide), polypropylene oxide, polypropylene glycol, polytetramethylene oxide, polyvinyl pyrrolidone, polyacrylamide, poly (hydroxy ethyl acrylate), poly(hydroxyethyl methacrylate), or mixtures or co-polymers thereof.
6. The three-dimensional hydrogel of any one of clauses 1-5, wherein hydrophilic polymer content is within a range of 2.0-4.0% w/v, wherein the concentration of the RGD-containing peptide is within a range of 0.05%-1.0% w/v, and wherein the shear modulus is 0.5 to 2.5 kPa.
7. The three-dimensional hydrogel of any one of clauses 1-6, wherein the shear modulus is 1.3 kPa and the RGD-containing peptide concentration is 0.1% w/v.
8. The three-dimensional hydrogel of any one of clauses 1-5 further comprising laminin111, laminin-111 analogue or laminin-111 fragment at concentration of 5 .g/ml to 250

.g/ml, and wherein the hydrogel has an initial shear modulus of 0.5 to 2.5 kPa and a final shear modulus of 50-200 Pa.
9. The three-dimensional hydrogel of clause 8, wherein the initial shear modulus is 1.0-2.0 kPa and the final shear modulus is 80-150 Pa after 4 days of cell culture.
10. The three-dimensional hydrogel of any one of clauses 1-5 further comprising laminin111, laminin-111 analogue or laminin-111 fragment at concentration of 5 .g/ml to 250 .g/ml, and wherein the hydrophilic polymer is poly(ethylene glycol) (PEG) that consists of PEG-vinyl sulfone (PEG-VS)/PEG-acrylate (PEG-Acr) hybrid at ratio 1:3, and wherein the hydrogel has an initial shear modulus of 0.5 to 2.5 kPa and a final shear modulus of 80-150 Pa after 4 days of cell culture.
11. A method for expanding adult epithelial stem cells, the method comprising encapsulating single cells or multicellular clusters in the three-dimensional hydrogel of any one of clauses 1-10 and culturing the cells under suitable stem cell expansion conditions.
12. The method from clause 11, wherein the cells are intestinal, colonic, gastric, hepatic, pancreatic, rectal, mammary or lung stem cells.
13. A method for culturing and expanding normal epithelial organoids, the method comprising: i) encapsulating fragments of epithelial organoids in the three-dimensional hydrogel of any one of clauses 1-10, and culturing the organoids under suitable organoid formation conditions, or ii) encapsulating single or clusters of epithelial stem cells in the three-dimensional hydrogel of any one of clauses 1-10, expanding the cells under suitable stem cell expansion conditions and subsequently switching to suitable organoid formation conditions.
14. The method of clause 13, wherein the epithelial organoids are intestinal, colonic, gastric, hepatic, pancreatic, rectal, mammary or lung-derived.
15. A method for culturing and expanding epithelial tumor-derived organoids, the method comprising encapsulating tumor-derived single cells or multicellular clusters in the three-dimensional hydrogel of any one of clauses 1-10, expanding the cells under suitable cell expansion conditions and subsequently switching to suitable organoid formation conditions.
16. The method of clause 15, wherein the tumor-derived cells are derived from colorectal, gastric, hepatic, pancreatic, mammary or lung tumors.
17. A method for epithelial tissue regeneration comprising a) encapsulating and expanding of patient-derived epithelial stem cells or organoids in the three-dimensional hydrogel of any one of clauses 1-10 under suitable stem cell expansion conditions or suitable organoid formation conditions, and b) transplanting the expanded stem cells or organoids back into the patient.
18. A method for studying intestinal stem cell self-renewal and colony formation, the method comprising encapsulating intestinal stem cells in the three-dimensional hydrogel of any one of clauses 1-10 and culturing the cells under suitable stem cell expansion conditions.
19. A method for studying intestinal stem cell differentiation, intestinal tissue polarization and morphogenesis, the method comprising: i) encapsulating fragments of intestinal organoids in the three-dimensional hydrogel of any one of clauses 1-10, and culturing the organoids under suitable organoid formation conditions, or i) encapsulating single or clusters of intestinal stem cells in the three-dimensional hydrogel of any one of clauses 1-10, expanding the cells under suitable self-renewal conditions and subsequently switching to suitable organoid formation conditions.
20. A method for screening of libraries of pharmacologic compounds, biomolecules or evaluating cell-based therapies for efficacy in inducing tumor cell death or growth arrest, the method comprising i) encapsulating tumor cells or organoids in the three-dimensional hydrogel of any one of clauses 1-10 and culturing the cells or organoids under suitable conditions in the presence of the pharmacologic compounds, biomolecules or cells to be tested, and ii) monitoring cell death and/or growth arrest.
21. A method for screening of libraries of pharmacologic compounds or biomolecules for efficacy in treating intestinal diseases, the method comprising i) providing intestinal biopsy sample from a patient, ii) encapsulating and growing the intestinal biopsy sample in the three-dimensional hydrogel of any one of clauses 1-10 and culturing the biopsy sample under suitable conditions in the presence of the pharmacologic compounds or biomolecules to be tested, and iii) in the case of cystic fibrosis, assessing the successful function restoration of the cystic fibrosis transmembrane conductance regulator (CFTR) by means of monitoring Forskolin-induced organoid swelling; or iii) in the case of inflammatory bowel disease, monitoring the successful reduction in inflammation, cell damage or death, or restoration of epithelial junction integrity.
22. The method of clause 21, wherein intestinal diseases are selected from the group comprising cystic fibrosis and inflammatory bowel disease.
23. A kit of parts for making discrete volumes of the three-dimensional hydrogel according to any one of clauses 1 to 10, comprising the following components a) one or more hydrophilic precursor polymers; b) fibronectin, a fibronectin analogue or a fibronectin-derived fragment; c) a crosslinking agent for the precursor polymers a); and d) laminin-111, laminin-111 analogue or laminin-111 fragment.
24. The kit of parts according to clause 23, wherein the hydrophilic polymers comprise multiarm poly(ethylene glycol) molecules, and wherein the fibronectin-derived fragment is 10 RGDSPG peptide.
25. The kit of parts according to clause 23 or 24, wherein the components are provided pre-supplied in a container, preferably in wells of a multi-well plate or in a tube, in substantially unreacted form, preferably in dried form.

REFERENCES

[1] T. Ueno and M. Fukuzawa, 'Current status of intestinal transplantation', Surg. Today, vol. 40, no. 12, pp. 1112-1122, December 2010.
[2] R. E. Hynds and A. Giangreco, 'The relevance of human stem cell-derived organoid models for epithelial translational medicine', Stem Cells Dayt. Ohio, vol. 31, no. 3, pp. 417-422, March 2013.
[3] T. Sato, D. E. Stange, M. Ferrante, R. G. J. Vries, J. H. Van Es, S. Van den Brink, W. J. Van Houdt, A. Pronk, J. Van Gorp, P. D. Siersema, and H. Clevers, tong-term expansion of epithelial organoids from human colon, adenoma, adenocarcinoma, and Barrett's epithelium', Gastroenterology, vol. 141, no. 5, pp. 1762-1772, November 2011.
[4] M. Fukuda, T. Mizutani, W. Mochizuki, T. Matsumoto, K. Nozaki, Y. Sakamaki, S. Ichinose, Y. Okada, T. Tanaka, M. Watanabe, and T. Nakamura, 'Small intestinal stem cell identity is maintained with functional Paneth cells in heterotopically grafted epithelium onto the colon', *Genes Dev.*, vol. 28, no. 16, pp. 1752-1757, August 2014.

[5] C. S. Hughes, L. M. Postovit, and G. A. Lajoie, 'Matrigel: a complex protein mixture required for optimal growth of cell culture', *Proteomics*, vol. 10, no. 9, pp. 1886-1890, May 2010.

[6] M. Pierzchalska, M. Grabacka, M. Michalik, K. Zyla, and P. Pierzchalski, 'Prostaglandin E2 supports growth of chicken embryo intestinal organoids in Matrigel matrix', *BioTechniques*, vol. 52, no. 5, pp. 307-315, May 2012.

[7] M. Eiraku, N. Takata, H. Ishibashi, M. Kawada, E. Sakakura, S. Okuda, K. Sekiguchi, T. Adachi, and Y. Sasai, 'Self-organizing optic-cup morphogenesis in three-dimensional culture', *Nature*, vol. 472, no. 7341, pp. 51-56, April 2011.

[8] A. Lowe, R. Harris, P. Bhansali, A. Cvekl, and W. Liu, 'Intercellular Adhesion-Dependent Cell Survival and ROCK-Regulated Actomyosin-Driven Forces Mediate Self-Formation of a Retinal Organoid', *Stem Cell Rep.*, vol. 6, no. 5, pp. 743-756, May 2016.

[9] C. Velagapudi, R.-P. Nilsson, M. J. Lee, H. S. Burns, J. M. Ricono, M. Arar, V. L. Barnes, H. E. Abboud, and J. L. Barnes, 'Reciprocal induction of simple organogenesis by mouse kidney progenitor cells in three-dimensional co-culture', *Am. J. Pathol.*, vol. 180, no. 2, pp. 819-830, Feburary 2012.

[10] S. D. Ramachandran, K. Schirmer, B. Münst, S. Heinz, S. Ghafoory, S. Wölfl, K. Simon-Keller, A. Marx, C. I. ie, M. P. Ebert, H. Walles, J. Braspenning, and K. Breitkopf-Heinlein, 'In Vitro Generation of Functional Liver Organoid-Like Structures Using Adult Human Cells', *PLoS ONE*, vol. 10, no. 10, October 2015.

[11] M. A. Schumacher, E. Aihara, R. Feng, A. Engevik, N. F. Shroyer, K. M. Ottemann, R. T. Worrell, M. H. Montrose, R. A. Shivdasani, and Y. Zavros, 'The use of murine-derived fundic organoids in studies of gastric physiology', *J. Physiol.*, vol. 593, no. Pt 8, pp. 1809-1827, April 2015.

[12] E. L. Calderon-Gierszal and G. S. Prins, 'Directed Differentiation of Human Embryonic Stem Cells into Prostate Organoids In Vitro and its Perturbation by Low-Dose Bisphenol A Exposure', *PloS One*, vol. 10, no. 7, p. e0133238, 2015.

[13] A. J. Ewald, 'Isolation of mouse mammary organoids for long-term time-lapse imaging', *Cold Spring Harb. Protoc.*, vol. 2013, no. 2, pp. 130-133, February 2013.

[14] K.-V. Nguyen-Ngoc, E. R. Shamir, R. J. Huebner, J. N. Beck, K. J. Cheung, and A. J. Ewald, '3D Culture Assays of Murine Mammary Branching Morphogenesis and Epithelial Invasion', *Methods Mol. Biol. Clifton N.J.*, vol. 1189, pp. 135-162, 2015.

[15] C. C. Chang, W. Sun, A. Cruz, M. Saitoh, M. H. Tai, and J. E. Trosko, 'A human breast epithelial cell type with stem cell characteristics as target cells for carcinogenesis', *Radiat. Res.*, vol. 155, no. 1 Pt 2, pp. 201-207, January 2001.

[16] E. Longworth-Mills, K. R. Koehler, and E. Hashino, 'Generating Inner Ear Organoids from Mouse Embryonic Stem Cells', *Methods Mol. Biol. Clifton N.J.*, vol. 1341, pp. 391-406, 2016.

[17] L. L. Y. Chiu, R. K. Iyer, J.-P. King, and M. Radisic, 'Biphasic electrical field stimulation aids in tissue engineering of multicell-type cardiac organoids', *Tissue Eng. Part A*, vol. 17, no. 11-12, pp. 1465-1477, June 2011.

[18] A. Soto-Gutierrez, N. Navarro-Alvarez, H. Yagi, Y. Nahmias, M. L. Yarmush, and N. Kobayashi, 'Engineering of an hepatic organoid to develop liver assist devices', *Cell Transplant*, vol. 19, no. 6, pp. 815-822, 2010.

[19] S. F. Boj, C.-I. Hwang, L. A. Baker, I. I. C. Chio, D. D. Engle, V. Corbo, M. Jager, M. Ponz-Sarvise, H. Tiriac, M. S. Spector, A. Gracanin, T. Oni, K. H. Yu, R. van Boxtel, M. Huch, K. D. Rivera, J. P. Wilson, M. E. Feigin, D. Ohlund, A. Handly-Santana, C. M. Ardito-Abraham, M. Ludwig, E. Elyada, B. Alagesan, G. Biffi, G. N. Yordanov, B. Delcuze, B. Creighton, K. Wright, Y. Park, F. H. M. Morsink, I. Q. Molenaar, I. H. Borel Rinkes, E. Cuppen, Y. Hao, Y. Jin, I. J. Nijman, C. Iacobuzio-Donahue, S. D. Leach, D. J. Pappin, M. Hammell, D. S. Klimstra, O. Basturk, R. H. Hruban, G. J. Offerhaus, R. G. J. Vries, H. Clevers, and D. A. Tuveson, 'Organoid Models of Human and Mouse Ductal Pancreatic Cancer', *Cell*, vol. 160, no. 0, pp. 324-338, January 2015.

[20] M. Kessler, K. Hoffmann, V. Brinkmann, O. Thieck, S. Jackisch, B. Toelle, H. Berger, H.-J. Mollenkopf, M. Mangler, J. Sehouli, C. Fotopoulou, and T. F. Meyer, 'The Notch and Wnt pathways regulate stemness and differentiation in human fallopian tube organoids', *Nat. Commun.*, vol. 6, December 2015.

[21] M. A. Lancaster, M. Renner, C.-A. Martin, D. Wenzel, L. S. Bicknell, M. E. Hurles, T. Homfray, J. M. Penninger, A. P. Jackson, and J. A. Knoblich, 'Cerebral organoids model human brain development and microcephaly', *Nature*, vol. 501, no. 7467, September 2013.

[22] N. D. Kim, K. J. Paik, and K. H. Clifton, 'Inhibitory effects of retinoids on development of squamous metaplasia in rat mammary epithelial organoids cultured in Matrigel', *Cancer Lett.*, vol. 110, no. 1-2, pp. 217-223, December 1996.

[23] N. Gjorevski and M. Lutolf, 'Biomaterials approaches in stem cell mechanobiology', *Prog. Mol. Biol. Transl. Sci.*, vol. 126, pp. 257-278, 2014.

[24] M. P. Lutolf, J. L. Lauer-Fields, H. G. Schmoekel, A. T. Metters, F. E. Weber, G. B. Fields, and J. A. Hubbell, 'Synthetic matrix metalloproteinase-sensitive hydrogels for the conduction of tissue regeneration: Engineering cell-invasion characteristics', *Proc. Natl. Acad. Sci.*, vol. 100, no. 9, pp. 5413-5418, April 2003.

[25] M. P. Lutolf, P. M. Gilbert, and H. M. Blau, 'Designing materials to direct stem-cell fate', *Nature*, vol. 462, no. 7272, pp. 433-441, November 2009.

[26] S. Halstenberg, A. Panitch, S. Rizzi, H. Hall, and J. A. Hubbell, 'Biologically engineered protein-graft-poly(ethylene glycol) hydrogels: a cell adhesive and plasmin-degradable biosynthetic material for tissue repair', *Biomacromolecules*, vol. 3, no. 4, pp. 710-723, August 2002.

[27] M. Luetolf, J. Schense, A. Jen, and J. Hubbell, 'Synthetic Matrix for Controlled Cell Ingrowth and Tissue Regeneration', WO03040235 (A1), 15-May-2003.

[28] S. C. Rizzi, M. Ehrbar, S. Halstenberg, G. P. Raeber, H. G. Schmoekel, H. Hagenmüller, R. Muller, F. E. Weber, and J. A. Hubbell, 'Recombinant protein-co-PEG networks as cell-adhesive and proteolytically degradable hydrogel matrixes. Part II: biofunctional characteristics', *Biomacromolecules*, vol. 7, no. 11, pp. 3019-3029, November 2006.

[29] K. Bott, Z. Upton, K. Schrobback, M. Ehrbar, J. A. Hubbell, M. P. Lutolf, and S. C. Rizzi, The effect of matrix characteristics on fibroblast proliferation in 3D gels', *Biomaterials*, vol. 31, no. 32, pp. 8454-8464, November 2010.

[30] D. Loessner, K. S. Stok, M. P. Lutolf, D. W. Hutmacher, J. A. Clements, and S. C. Rizzi, 'Bioengineered 3D

[31] platform to explore cell-ECM interactions and drug resistance of epithelial ovarian cancer cells', *Biomaterials*, vol. 31, no. 32, pp. 8494-8506, November 2010.

[31] W. Murphy, N. Le, M. Schwartz, E. Nguyen, S. Zorn, H. Ardalani, M. Zanotelli, M. Parlato, D. Belair, and W. Daly, 'Hydrogel Compositions for Use in Promoting Tubulogenesis', WO2015157732 (A1), 15-Oct.-2015.

[32] A. Raza, C. S. Ki, and C.-C. Lin, 'The influence of matrix properties on growth and morphogenesis of human pancreatic ductal epithelial cells in 3D', *Biomaterials*, vol. 34, no. 21, pp. 5117-5127, July 2013.

[33] N. O. Enemchukwu, 'Bioartifical matricies to modulate epithelial morphogenesis', Georgia Institute of Technology, 2013.

[34] S. Levison, N. Skop, F. Calderon, C. Cho, and C. Gandhi, 'Growth Matrices for Stem Cell Propagation in Vitro and in Tissue Regeneration', WO2014117146 (A1), 31-Jul.-2014.

[35] A. Fadeev, J. Gehman, Z. Melkoumian, D. Weber, Y. Zhou, and R. Brandenberger, 'Synthetic Surfaces for Culturing Cells in Chemically Defined Media', WO2009099555 (A2), 13-Aug.-2009.

[36] X. Yin, B. E. Mead, H. Safaee, R. Langer, J. M. Karp, and O. Levy, 'Engineering Stem Cell Organoids', *Cell Stem Cell*, vol. 18, no. 1, pp. 25-38, January 2016.

[37] B. D. Mather, K. Viswanathan, K. M. Miller, and T. E. Long, 'Michael addition reactions in macromolecular design for emerging technologies', *Prog. Polym. Sci.*, vol. 31, no. 5, pp. 487-531, May 2006.

[38] P. van de Wetering, A. T. Metters, R. G. Schoenmakers, and J. A. Hubbell, 'Poly(ethylene glycol) hydrogels formed by conjugate addition with controllable swelling, degradation, and release of pharmaceutically active proteins', *J. Control. Release Off. J. Control. Release Soc.*, vol. 102, no. 3, pp. 619-627, February 2005.

[39] D. L. Elbert and J. A. Hubbell, 'Conjugate addition reactions combined with free-radical cross-linking for the design of materials for tissue engineering', *Biomacromolecules*, vol. 2, no. 2, pp. 430-441, 2001.

[40] S. C. Rizzi and J. A. Hubbell, 'Recombinant protein-co-PEG networks as cell-adhesive and proteolytically degradable hydrogel matrixes. Part I: Development and physicochemical characteristics', *Biomacromolecules*, vol. 6, no. 3, pp. 1226-1238, June 2005.

[41] C. D. Pritchard, T. M. O'Shea, D. J. Siegwart, E. Calo, D. G. Anderson, F. M. Reynolds, J. A. Thomas, J. R. Slotkin, E. J. Woodard, and R. Langer, 'An injectable thiol-acrylate poly(ethylene glycol) hydrogel for sustained release of methylprednisolone sodium succinate', *Biomaterials*, vol. 32, no. 2, pp. 587-597, January 2011.

[42] A. Metters and J. Hubbell, 'Network formation and degradation behavior of hydrogels formed by Michael-type addition reactions', *Biomacromolecules*, vol. 6, no. 1, pp. 290-301, February 2005.

[43] M. p. Lutolf, G. p. Raeber, A. h. Zisch, N. Tirelli, and J. a. Hubbell, 'Cell-Responsive Synthetic Hydrogels', *Adv. Mater.*, vol. 15, no. 11, pp. 888-892, June 2003.

[44] A. B. Pratt, F. E. Weber, H. G. Schmoekel, R. Muller, and J. A. Hubbell, 'Synthetic extracellular matrices for in situ tissue engineering', *Biotechnol. Bioeng.*, vol. 86, no. 1, pp. 27-36, April 2004.

[45] E. A. Phelps, N. O. Enemchukwu, V. F. Fiore, J. C. Sy, N. Murthy, T. A. Sulchek, T. H. Barker, and A. J. Garcia, 'Maleimide cross-linked bioactive PEG hydrogel exhibits improved reaction kinetics and cross-linking for cell encapsulation and in situ delivery', *Adv. Mater. Deerfield Beach Fla*, vol. 24, no. 1, pp. 64-70, 2, January 2012.

[46] A. J. Garcia, 'PEG-Maleimide Hydrogels for Protein and Cell Delivery in Regenerative Medicine', *Ann. Biomed. Eng.*, vol. 42, no. 2, pp. 312-322, February 2014.

[47] Y. Fu and W. J. Kao, 'In situ forming poly(ethylene glycol)-based hydrogels via thiol-maleimide Michael-type addition', *J. Biomed. Mater. Res. A*, vol. 98, no. 2, pp. 201-211, August 2011.

[48] H. Zhou, J. Woo, A. M. Cok, M. Wang, B. D. Olsen, and J. A. Johnson, 'Counting primary loops in polymer gels', *Proc. Natl. Acad. Sci.*, vol. 109, no. 47, pp. 19119-19124, November 2012.

[49] A. Shikanov, R. M. Smith, M. Xu, T. K. Woodruff, and L. D. Shea, 'Hydrogel network design using multifunctional macromers to coordinate tissue maturation in ovarian follicle culture', *Biomaterials*, vol. 32, no. 10, pp. 2524-2531, April 2011.

[50] J. Kim, Y. P. Kong, S. M. Niedzielski, R. K. Singh, A. J. Putnam, and A. Shikanov, 'Characterization of the crosslinking kinetics of multi-arm poly(ethylene glycol) hydrogels formed via Michael-type addition', *Soft Matter*, vol. 12, no. 7, pp. 2076-2085, February 2016.

[51] U. Hersel, C. Dahmen, and H. Kessler, 'RGD modified polymers: biomaterials for stimulated cell adhesion and beyond', *Biomaterials*, vol. 24, no. 24, pp. 4385-4415, November 2003.

[52] G. P. Raeber, M. P. Lutolf, and J. A. Hubbell, 'Molecularly Engineered PEG Hydrogels: A Novel Model System for Proteolytically Mediated Cell Migration', *Biophys. J.*, vol. 89, no. 2, pp. 1374-1388, August 2005.

[53] M. H. Fittkau, P. Zilla, D. Bezuidenhout, M. P. Lutolf, P. Human, J. A. Hubbell, and N. Davies, 'The selective modulation of endothelial cell mobility on RGD peptide containing surfaces by YIGSR peptides', *Biomaterials*, vol. 26, no. 2, pp. 167-174, January 2005.

[54] M. P. Lutolf and J. A. Hubbell, 'Synthesis and physicochemical characterization of end-linked poly(ethylene glycol)-co-peptide hydrogels formed by Michael-type addition', *Biomacromolecules*, vol. 4, no. 3, pp. 713-722, June 2003.

[55] W. H. Kim, M. Nomizu, S. Y. Song, K. Tanaka, Y. Kuratomi, H. K. Kleinman, and Y. Yamada, 'Laminin-alpha1-chain sequence Leu-Gln-Val-Gln-Leu-Ser-Ile-Arg (LQVQLSIR) enhances murine melanoma cell metastases', *Int. J. Cancer*, vol. 77, no. 4, pp. 632-639, August 1998.

[56] A. Woods, J. B. McCarthy, L. T. Furcht, and J. R. Couchman, 'A synthetic peptide from the COOH-terminal heparin-binding domain of fibronectin promotes focal adhesion formation', *Mol. Biol. Cell*, vol. 4, no. 6, pp. 605-613, June 1993.

[57] S. L. Drake, J. Varnum, K. H. Mayo, P. C. Letourneau, L. T. Furcht, and J. B. McCarthy, 'Structural features of fibronectin synthetic peptide FN-C/H II, responsible for cell adhesion, neurite extension, and heparan sulfate binding', *J. Biol. Chem.*, vol. 268, no. 21, pp. 15859-15867, July 1993.

[58] S. P. Massia and J. A. Hubbell, 'Vascular endothelial cell adhesion and spreading promoted by the peptide REDV of the IIICS region of plasma fibronectin is mediated by integrin alpha 4 beta 1', *J. Biol. Chem.*, vol. 267, no. 20, pp. 14019-14026, July 1992.

[59] M. Herten, R. E. Jung, D. Ferrari, D. Rothamel, V. Golubovic, A. Molenberg, C. H. F. Hammerle, J. Becker, and F. Schwarz, 'Biodegradation of different synthetic hydrogels made of polyethylene glycol hydrogel/RGD-peptide modifications: an immunohistochemical study in rats', *Clin. Oral Implants Res.*, vol. 20, no. 2, pp. 116-125, February 2009.

[60] J. R. Klim, L. Li, P. J. Wrighton, M. S. Piekarczyk, and L. L. Kiessling, 'A defined glycosaminoglycan-binding substratum for human pluripotent stem cells', *Nat. Methods*, vol. 7, no. 12, pp. 989-994, December 2010.

[61] L. Y. Santiago, R. W. Nowak, J. Peter Rubin, and K. G. Marra, 'Peptide-surface modification of poly(caprolactone) with laminin-derived sequences for adipose-derived stem cell applications', *Biomaterials*, vol. 27, no. 15, pp. 2962-2969, May 2006.

[62] M. Nomizu, B. S. Weeks, C. A. Weston, W. H. Kim, H. K. Kleinman, and Y. Yamada, 'Structure-activity study of a laminin alpha 1 chain active peptide segment Ile-Lys-Val-Ala-Val (IKVAV)', *FEBS Lett.*, vol. 365, no. 2-3, pp. 227-231, May 1995.

[63] C. Renner, B. Sacca, and L. Moroder, 'Synthetic heterotrimeric collagen peptides as mimics of cell adhesion sites of the basement membrane', *Biopolymers*, vol. 76, no. 1, pp. 34-47, 2004.

[64] J. Zhu and R. E. Marchant, 'Design properties of hydrogel tissue-engineering scaffolds', *Expert Rev. Med. Devices*, vol. 8, no. 5, pp. 607-626, September 2011.

[65] S. Randell and L. Fulcher, *Methods in Molecular Biology: Epithelial cell culture protocols*, vol. 945.2013.

[66] M. A. Lancaster and J. A. Knoblich, 'Organogenesis in a dish: modeling development and disease using organoid technologies', *Science*, vol. 345, no. 6194, p. 1247125, July 2014.

[67] O. Kovbasnjuk, N. C. Zachos, J. In, J. Foulke-Abel, K. Ettayebi, J. M. Hyser, J. R. Broughman, X.-L. Zeng, S. Middendorp, H. R. de Jonge, M. K. Estes, and M. Donowitz, 'Human enteroids: preclinical models of non-inflammatory diarrhea', *Stem Cell Res. Ther.*, vol. 4, no. Suppl 1, p. S3, December 2013.

[68] Y. Wang, A. A. Ahmad, P. K. Shah, C. E. Sims, S. T. Magness, and N. L. Allbritton, 'Capture and 3D culture of colonic crypts and colonoids in a microarray platform', *Lab. Chip*, vol. 13, no. 23, pp. 4625-4634, December 2013.

[69] T. Sato, R. G. Vries, H. J. Snippert, M. van de Wetering, N. Barker, D. E. Stange, J. H. van Es, A. Abo, P. Kujala, P. J. Peters, and H. Clevers, 'Single Lgr5 stem cells build crypt—villus structures in vitro without a mesenchymal niche', *Nature*, vol. 459, no. 7244, pp. 262-265, May 2009.

[70] X. Yin, H. F. Farin, J. H. van Es, H. Clevers, R. Langer, and J. M. Karp, 'Niche-independent high-purity cultures of Lgr5+ intestinal stem cells and their progeny', *Nat. Methods*, vol. 11, no. 1, pp. 106-112, January 2014.

The invention claimed is:

1. A method for obtaining an epithelial cell organoid, comprising culturing epithelial stem cells in a biofunctional 3D synthetic hydrogel, wherein:
   a) the epithelial stem cells comprise isolated tissue or organoid fragments and wherein the epithelial stem cells are cultured in conditions suitable for organoid formation wherein said conditions suitable for organoid formation comprise providing the epithelial stem cells with medium comprising a component selected from the group consisting of EGF, Noggin, and R-spondin or combinations thereof; or
   b) the epithelial stem cells comprise single or clusters of stem cells, and wherein the epithelial stem cells are first cultured in conditions suitable for cell expansion and subsequently cultured in conditions suitable for organoid formation wherein said conditions suitable for organoid formation comprise providing the epithelial stem cells with medium comprising a component selected from the group consisting of EGF, Noggin, and R-spondin or combinations thereof, wherein the synthetic hydrogel comprises a crosslinked synthetic hydrophilic polymer and a bioactive molecule, wherein the bioactive molecule is laminin-111 or a functional fragment thereof, and wherein the synthetic hydrogel has an initial shear modulus, prior to the culturing step in conditions suitable for organoid formation, of between 0.05-1.5 kPa.

2. The method of claim 1, step b) wherein the shear modulus of the hydrogel decreases over time.

3. The method of claim 2, wherein the shear modulus of the hydrogel at the start of the method is between 0.5-1.5 kPa and the shear modulus of the hydrogel during the culturing step in conditions suitable for organoid formation is 50 to 500 Pa.

4. The method of claim 2, wherein the decrease in the shear modulus of the hydrogel is achieved through degradation of the hydrogel network.

5. The method of claim 4, wherein the hydrogel comprises multiarm poly(ethylene glycol) (PEG) molecules and ester bonds are derived from reactive groups on said multiarm PEG molecules, and wherein said degradation of the hydrogel network is achieved by hydrolysis of said ester bonds.

6. The method of claim 5, wherein the multiarm PEG molecules comprise an average of 3 to 12 arms.

7. The method of claim 5, wherein the multiarm PEG molecules comprise 70-80% of the entire hydrogel network.

8. The method of claim 4, wherein the hydrogel is insensitive to degradation by cell-secreted proteases.

9. The method of claim 2, wherein the decrease in the shear modulus of the hydrogel is achieved through a biocompatible active mechanism.

10. The method of claim 9, wherein the active mechanism is selective for only one component of the hydrogel.

11. The method of claim 9, wherein the active mechanism comprises cleavage of specific target sites in the hydrogel by a proteolytic enzyme.

12. The method of claim 1, wherein the laminin-111 or a functional variant thereof is at a concentration of at least 5 µg/ml.

13. The method of claim 1, wherein the hydrogel comprises a further bioactive molecule.

14. The method of claim 13 wherein the further bioactive molecule is selected from the group consisting of an oligopeptide, a small molecule, a protein, an oligo- or polysaccharide, or and an oligo- or poly-nucleotide.

15. The method of claim 13, wherein the further bioactive molecule comprises an RGD-containing ligand.

16. The method of claim 15, wherein the RGD-containing ligand is fibronectin or a functional variant thereof.

17. The method of claim 15 wherein the RGD containing ligand is selected from the group consisting of: RGD, RGDS (SEQ ID NO: 11), RGDSP (SEQ ID NO: 2), RGDSPK (SEQ ID NO: 3), RGDTP (SEQ ID NO: 4), and RGDSPASSKP (SEQ ID NO: 5).

18. The method of claim 16, wherein the functional variant of fibronectin is a branched or cyclic peptide.

19. The method of claim 16, wherein the functional variant thereof is selected from the group consisting of: III1-C fragment, FNIII9-10 fragment, and FNIII12-14 fragment.

20. The method of claim 1, wherein the synthetic hydrophilic polymer is selected from the group consisting of: polyethylene glycol, polyethylene oxide, polyoxazoline, polyaliphatic polyurethanes, polyether polyurethanes, polyester polyurethanes, polyethylene copolymers, polyamides, polyvinyl alcohols, polypropylene oxide, polypropylene glycol, polytetramethylene oxide, polyvinyl pyrrolidone, polyacrylamide, polyhydroxy ethyl acrylate, polyhydroxyethyl methacrylate, and mixtures and co-polymers thereof.

21. The method of claim 1, wherein the epithelial stem cells are selected from the group consisting of intestinal, colonic, gastric, hepatic, pancreatic, rectal, mammary, kidney, corneal, epidermal, hair follicle, prostate, eye and lung epithelial cells.

22. The method of claim 1, wherein the epithelial stem cells are tumour cells.

23. The method of claim 1, wherein the biofunctional 3D synthetic hydrogel is biocompatible.

24. A method for quantifying epithelial stem cell organoid formation and maintenance, the method comprising
 a) obtaining an organoid using the method of claim 1, and
 b) monitoring, by quantitative high-content approaches, the self-organization of the cells into organoids.

* * * * *

SEQUENCE LISTING

```
<160> NUMBER OF SEQ ID NOS: 26

<210> SEQ ID NO 1
<211> LENGTH: 12
<212> TYPE: PRT
<213> ORGANISM: Artificial Sequence
<220> FEATURE:
<223> OTHER INFORMATION: AG73

<400> SEQUENCE: 1

Arg Lys Arg Leu Gln Val Gln Leu Ser Ile Arg Thr
1               5                   10

<210> SEQ ID NO 2
<211> LENGTH: 5
<212> TYPE: PRT
<213> ORGANISM: Artificial Sequence
<220> FEATURE:
<223> OTHER INFORMATION: fibronectin-derived RGD-containing peptide

<400> SEQUENCE: 2

Arg Gly Asp Ser Pro
1               5

<210> SEQ ID NO 3
<211> LENGTH: 6
<212> TYPE: PRT
<213> ORGANISM: Artificial Sequence
<220> FEATURE:
<223> OTHER INFORMATION: fibronectin-derived RGD peptide

<400> SEQUENCE: 3

Arg Gly Asp Ser Pro Lys
1               5

<210> SEQ ID NO 4
<211> LENGTH: 5
<212> TYPE: PRT
<213> ORGANISM: Artificial Sequence
```

```
<220> FEATURE:
<223> OTHER INFORMATION: fibronectin-derived RGD peptide

<400> SEQUENCE: 4

Arg Gly Asp Thr Pro
1               5

<210> SEQ ID NO 5
<211> LENGTH: 10
<212> TYPE: PRT
<213> ORGANISM: Artificial Sequence
<220> FEATURE:
<223> OTHER INFORMATION: fibronectin-derived RGD peptide

<400> SEQUENCE: 5

Arg Gly Asp Ser Pro Ala Ser Ser Lys Pro
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Cyclo fibronectin-derived RGD peptide

<400> SEQUENCE: 6

Arg Gly Asp Phe Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Cyclo fibronectin-derived RGD peptide

<400> SEQUENCE: 7

Arg Gly Asp Tyr Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Cyclo fibronectin-derived RGD peptide

<400> SEQUENCE: 8

Arg Gly Asp Phe Cys
1               5

<210> SEQ ID NO 9
<211> LENGTH: 7
<212> TYPE: PRT
<213> ORGANISM: Artificial Sequence
<220> FEATURE:
<223> OTHER INFORMATION: Cleavage site

<400> SEQUENCE: 9

Glu Asn Leu Tyr Phe Gln Gly
1               5

<210> SEQ ID NO 10
<211> LENGTH: 7
<212> TYPE: PRT
<213> ORGANISM: Artificial Sequence
<220> FEATURE:
```

```
<223> OTHER INFORMATION: Cleavage site

<400> SEQUENCE: 10

Glu Asn Leu Tyr Phe Gln Ser
1               5

<210> SEQ ID NO 11
<211> LENGTH: 4
<212> TYPE: PRT
<213> ORGANISM: Artificial Sequence
<220> FEATURE:
<223> OTHER INFORMATION: Fibronectin-derived RGD peptide

<400> SEQUENCE: 11

Arg Gly Asp Ser
1

<210> SEQ ID NO 12
<211> LENGTH: 16
<212> TYPE: PRT
<213> ORGANISM: Artificial Sequence
<220> FEATURE:
<223> OTHER INFORMATION: FXIIIa substrate peptide

<400> SEQUENCE: 12

Phe Lys Gly Gly Gly Pro Gln Gly Ile Trp Gly Gln Glu Arg Cys Gly
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: FXIIIa substrate peptides

<400> SEQUENCE: 13

Asn Gln Glu Gln Val Ser Pro Leu Glu Arg Cys Gly
1               5                   10

<210> SEQ ID NO 14
<211> LENGTH: 14
<212> TYPE: PRT
<213> ORGANISM: Artificial Sequence
<220> FEATURE:
<223> OTHER INFORMATION: FXIIIa substrate peptide

<400> SEQUENCE: 14

Asn Gln Glu Gln Val Ser Pro Leu Arg Gly Asp Ser Pro Gly
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Fibronectin-derived RGD peptide

<400> SEQUENCE: 15

Lys Gln Ala Gly Asp Val
1               5

<210> SEQ ID NO 16
<211> LENGTH: 4
<212> TYPE: PRT
<213> ORGANISM: Artificial Sequence
<220> FEATURE:
<223> OTHER INFORMATION: Fibronectin-derived RGD peptide
```

```
<400> SEQUENCE: 16

Arg Glu Asp Val
1

<210> SEQ ID NO 17
<211> LENGTH: 5
<212> TYPE: PRT
<213> ORGANISM: Artificial Sequence
<220> FEATURE:
<223> OTHER INFORMATION: Fibronectin-derived RGD peptide

<400> SEQUENCE: 17

Pro His Ser Arg Asn
1               5

<210> SEQ ID NO 18
<211> LENGTH: 5
<212> TYPE: PRT
<213> ORGANISM: Artificial Sequence
<220> FEATURE:
<223> OTHER INFORMATION: Laminin-derived RGD peptide

<400> SEQUENCE: 18

Tyr Ile Gly Ser Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Laminin-derived RGD peptide

<400> SEQUENCE: 19

Leu Gly Thr Ile Pro Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Laminin-derived RGD peptide

<400> SEQUENCE: 20

Ile Lys Val Ala Val
1               5

<210> SEQ ID NO 21
<211> LENGTH: 5
<212> TYPE: PRT
<213> ORGANISM: Artificial Sequence
<220> FEATURE:
<223> OTHER INFORMATION: Laminin-derived RGD peptide

<400> SEQUENCE: 21

Pro Asp Gly Ser Arg
1               5

<210> SEQ ID NO 22
<211> LENGTH: 5
<212> TYPE: PRT
<213> ORGANISM: Artificial Sequence
<220> FEATURE:
<223> OTHER INFORMATION: Laminin-derived RGD peptide
```

```
<400> SEQUENCE: 22

Leu Arg Gly Asp Asn
1               5

<210> SEQ ID NO 23
<211> LENGTH: 5
<212> TYPE: PRT
<213> ORGANISM: Artificial Sequence
<220> FEATURE:
<223> OTHER INFORMATION: Laminin-derived RGD peptide

<400> SEQUENCE: 23

Ile Lys Leu Leu Ile
1               5

<210> SEQ ID NO 24
<211> LENGTH: 4
<212> TYPE: PRT
<213> ORGANISM: Artificial Sequence
<220> FEATURE:
<223> OTHER INFORMATION: Collagen-derived RGD peptide

<400> SEQUENCE: 24

Asp Gly Glu Ala
1

<210> SEQ ID NO 25
<211> LENGTH: 6
<212> TYPE: PRT
<213> ORGANISM: Artificial Sequence
<220> FEATURE:
<223> OTHER INFORMATION: Laminin-derived peptide sequence
<220> FEATURE:
<221> NAME/KEY: X
<222> LOCATION: (3)..(3)
<223> OTHER INFORMATION: X = pyrolysine

<400> SEQUENCE: 25

Gly Phe Xaa Gly Glu Arg
1               5

<210> SEQ ID NO 26
<211> LENGTH: 4
<212> TYPE: PRT
<213> ORGANISM: Artificial Sequence
<220> FEATURE:
<223> OTHER INFORMATION: Elastin-derived RGD peptide

<400> SEQUENCE: 26

Val Ala Pro Gly
1
```